(12) United States Patent
Zelphati et al.

(10) Patent No.: US 9,107,931 B2
(45) Date of Patent: Aug. 18, 2015

(54) CLASS OF CATIONIC LIPIDS FOR TRANSPORTING ACTIVE AGENTS INTO CELLS

(75) Inventors: Olivier Zelphati, Roquefort la Bédoule (FR); Stéphane Moutard, Marseilles (FR)

(73) Assignee: OZ BIOSCIENCES, Marseilles (FR)

( * ) Notice: Subject to any disclaimer, the term of this patent is extended or adjusted under 35 U.S.C. 154(b) by 832 days.

(21) Appl. No.: 13/028,940

(22) Filed: Feb. 16, 2011

(65) Prior Publication Data
US 2012/0015865 A1    Jan. 19, 2012

Related U.S. Application Data

(63) Continuation of application No. 12/809,820, filed as application No. PCT/FR2008/001755 on Dec. 16, 2008, now abandoned.

(30) Foreign Application Priority Data

Dec. 19, 2007 (FR) ...................... 07 08861

(51) Int. Cl.
*C12N 15/11* (2006.01)
*C12N 15/88* (2006.01)
*A61K 48/00* (2006.01)
(Continued)

(52) U.S. Cl.
CPC ........... *A61K 31/7052* (2013.01); *A61K 8/0291* (2013.01); *A61K 8/14* (2013.01); *A61K 8/46* (2013.01); *A61K 8/64* (2013.01); *A61K 9/0019* (2013.01); *A61K 9/127* (2013.01); *A61K 31/715* (2013.01); *A61K 47/48046* (2013.01); *A61Q 19/00* (2013.01); *C07C 69/58* (2013.01);
(Continued)

(58) Field of Classification Search
CPC ... A61K 38/00; A61K 48/00; A61K 2039/53; A61K 9/1272; A61K 47/48315; C12N 2310/315; C12N 15/113; C12N 2310/321; C12N 2310/14; C12N 15/88; C12N 15/87; C10G 33/04; C11C 3/00; C07C 335/32; C07C 317/44; A61M 1/3472; C07F 3/02; C07F 1/02; C07F 1/04; C07F 7/24
USPC .............. 252/182.3; 435/458, 375; 514/44 R, 514/44 A, 784, 54; 554/85
See application file for complete search history.

(56) References Cited

U.S. PATENT DOCUMENTS

| 5,100,655 A * | 3/1992 | Takano et al. .................... 424/63 |
| 5,719,131 A | 2/1998 | Harris et al. |
| 2005/0043534 A1* | 2/2005 | Bielawska et al. ............ 546/102 |

FOREIGN PATENT DOCUMENTS

| EP | 320976 A1 * | 6/1989 |
| EP | 775751 A | 5/1997 |

(Continued)

OTHER PUBLICATIONS

Nakamiya et al., "Antibactrial activity of lauryl ester of DL-lysine", vol. 54, No. 6, pp. 369-373.*

(Continued)

*Primary Examiner* — Deborah D Carr
(74) *Attorney, Agent, or Firm* — Browdy and Neimark, PLLC

(57) ABSTRACT

A subject of the present invention is the development of a novel family of cationic lipids and their use as vectors for in vitro, ex vivo and in 5 vivo delivery of biologically active agents.

33 Claims, 11 Drawing Sheets

Figure 1:
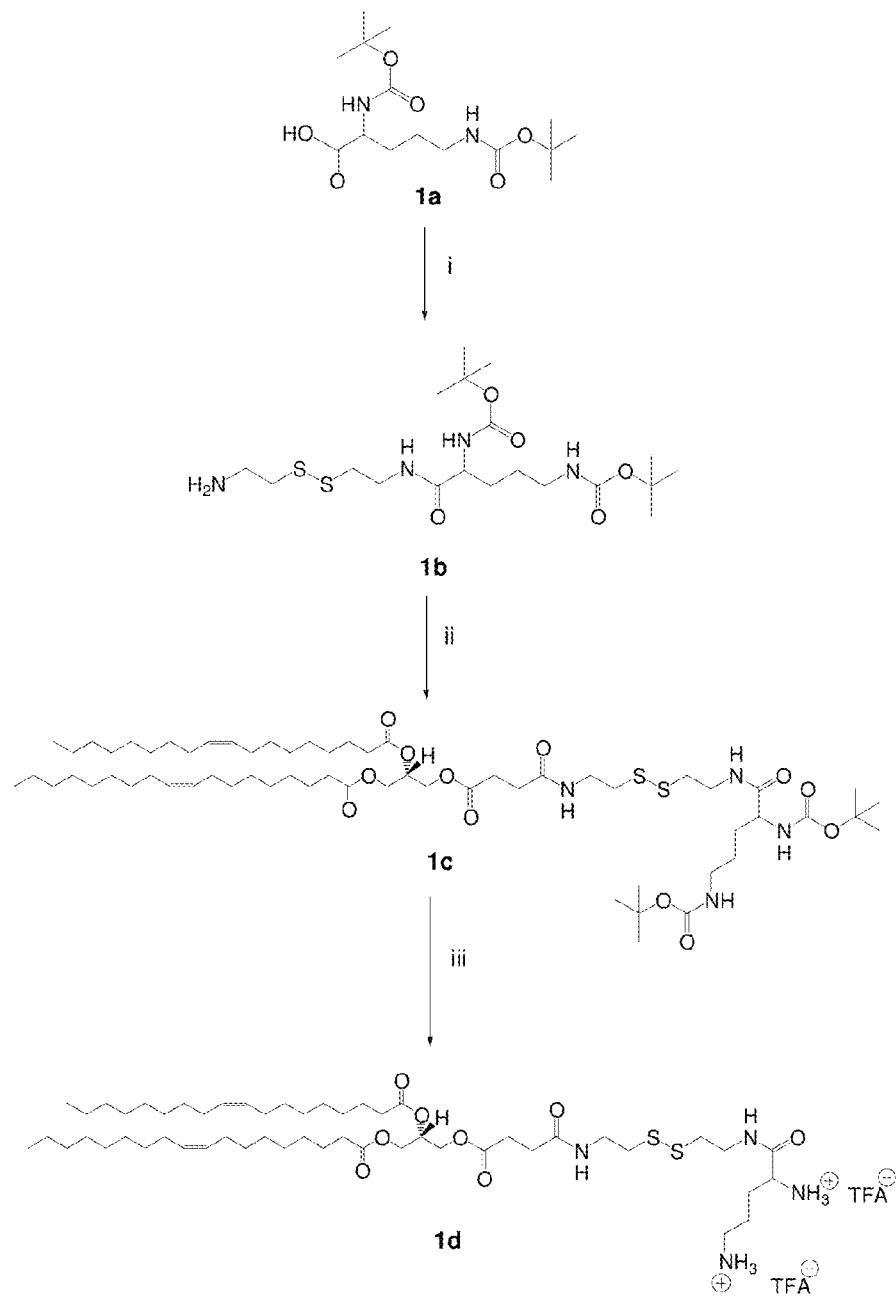

(51) Int. Cl.

| | |
|---|---|
| C07C 33/00 | (2006.01) |
| C08H 3/00 | (2006.01) |
| C11D 1/28 | (2006.01) |
| C09K 3/00 | (2006.01) |
| A61K 31/7052 | (2006.01) |
| A61K 8/02 | (2006.01) |
| A61K 8/14 | (2006.01) |
| A61K 8/46 | (2006.01) |
| A61K 8/64 | (2006.01) |
| A61K 9/00 | (2006.01) |
| A61K 9/127 | (2006.01) |
| A61K 31/715 | (2006.01) |
| A61K 47/48 | (2006.01) |
| A61Q 19/00 | (2006.01) |
| C07C 69/58 | (2006.01) |
| C07C 237/08 | (2006.01) |
| C07C 323/41 | (2006.01) |
| A61K 38/00 | (2006.01) |

(52) U.S. Cl.
CPC ............ *C07C237/08* (2013.01); *C07C 323/41* (2013.01); *C12N 15/88* (2013.01); *A61K 38/00* (2013.01)

(56) References Cited

FOREIGN PATENT DOCUMENTS

| | | | |
|---|---|---|---|
| EP | 784984 A | | 7/1997 |
| FR | 1351368 | * | 2/1964 |
| JP | 58134197 A | * | 8/1983 |
| NL | 6411149 | * | 4/1965 |
| WO | WO 8702367 A2 | * | 4/1987 |
| WO | 9518146 A | | 7/1995 |

OTHER PUBLICATIONS

De Souza et al., A Chiral Benzoquinolizine-2-carboxylic acid Arginine salt active against Vancomycin-Resistant *Staphylococcus aureus*, J. Med. Chem., 2005, 48, 5232-5242.*

Tang et al., "Synthesis of a single-tailed cationic lipid and inverstigation of its transfection", Journal of Controlled Release, vol. 62 (1999), pp. 345-358.*

STN description of Tang et al. showing compounds of interest.*

* cited by examiner

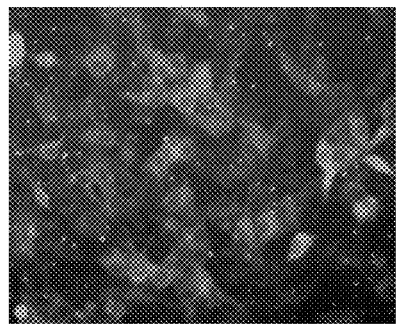
Figure 8A
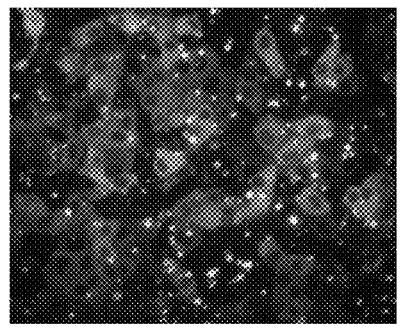
Figure 8B
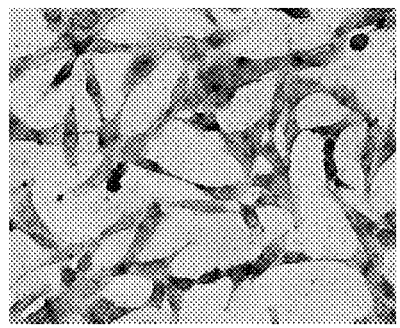
Figure 8C
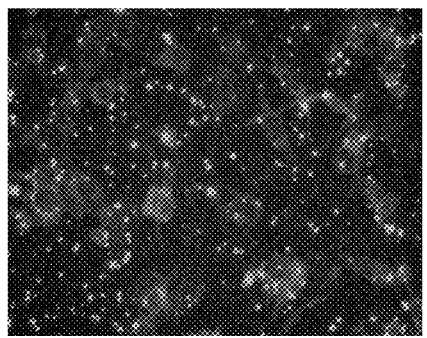
Figure 8D
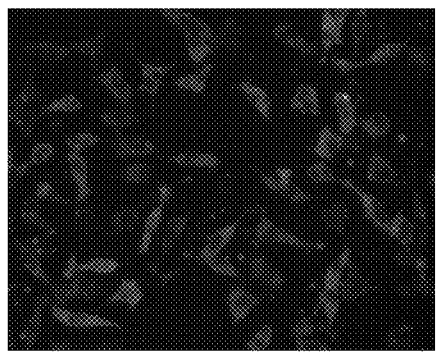
Figure 8E
Figures 8

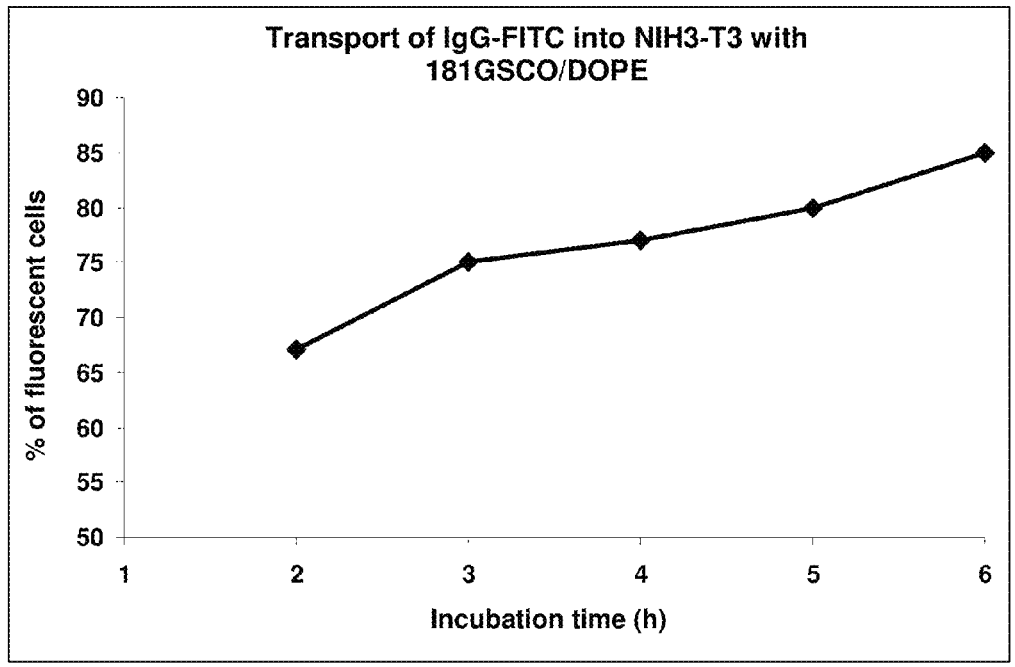
Figure 9A
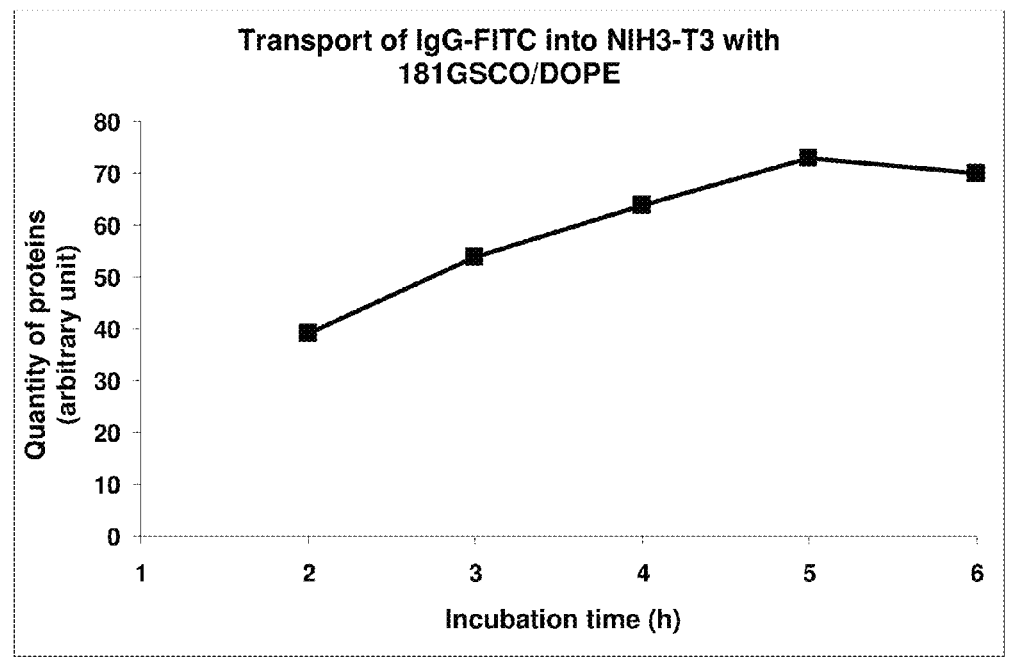
Figure 9B
Figure 9

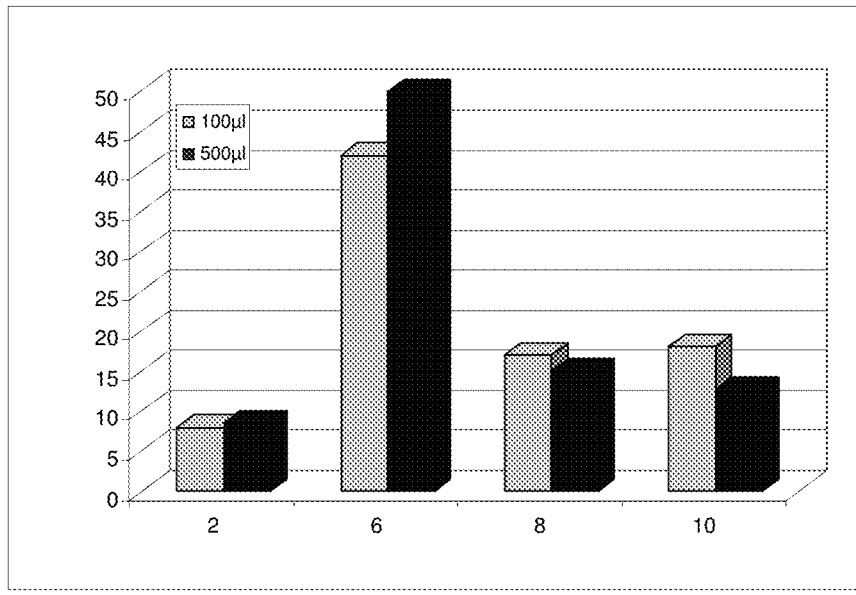
Figure 10A
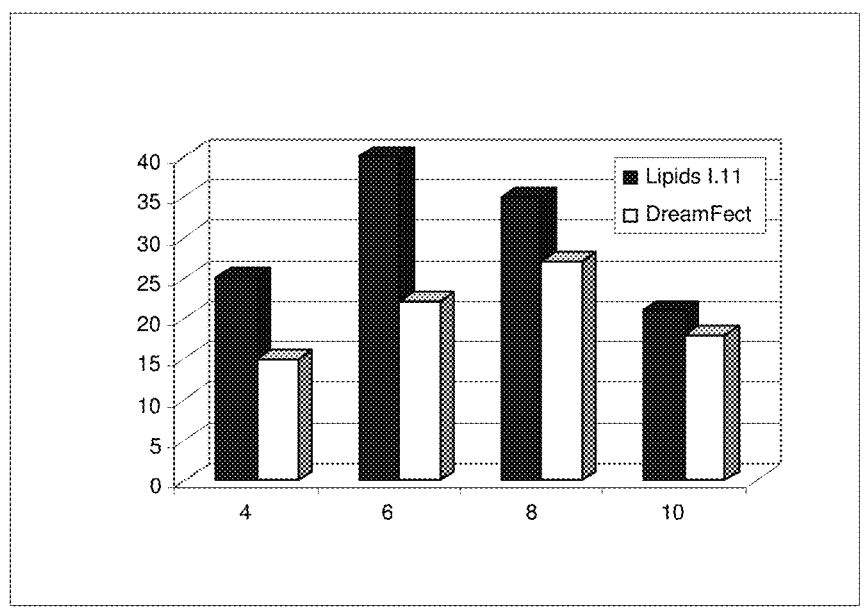
Figure 10B
Figure 10

CLASS OF CATIONIC LIPIDS FOR TRANSPORTING ACTIVE AGENTS INTO CELLS

A subject of the present invention is a novel family of cationic lipids and their use as vectors for in vitro, ex vivo and in vivo delivery of biologically active agents, in particular of nucleic acids, peptides, proteins, polysaccharides and lipids into living cells, in the tissues, organs and/or organisms which are human, animal and/or plant.

The intracellular delivery of biologically active agents finds applications in numerous fields ranging from biology to medicine. In biology, the introduction into the cells of nucleic acids (transfection) (genes or plasmids, linear coding DNA, artificial chromosomes, messenger RNA, interfering RNAs, double-stranded RNA such as shRNAs), antisense oligonucleotides, ribozymes can be used in particular for studying the regulation of the expression of genes or for clarifying their function. Similarly, the intracellular transport of peptides, proteins, polysaccharides, lipids and any other biologically active molecule makes it possible to comprehend and study the fundamental biological mechanisms. In medicine, these techniques have been developed for the delivery of peptides or therapeutic proteins, antisense oligonucleotides and ribozymes (antisense therapies), siRNA and genes (gene therapy) in order to remedy inter alia a metabolic deficiency, a genetic disorder or an infection.

Numerous methods for introducing nucleic acids into cells exist, which can be classified in three categories: physical, biochemical and biological. The biological methods make use of infectious organisms such as viruses or bacteria. The physical approaches include in particular electroporation, microinjection, sonoporation or magnetofection. Finally, the biochemical methods of transfection combine chemical reagents with nucleic acids (Conwell, C. G. et al. (2005) *Adv. Genet.* 53, 1-18). On the one hand, calcium phosphate or DEAE dextran are used in co-precipitation methods, on the other hand cationic polymers substituted or not substituted by ligands, cationic lipids in the form of systems which are organized or not (liposomes, unilamellar or multilamellar vesicles, hexagonal phases, micelles) and/or a mixture of these different entities, form complexes (polyplexes, lipoplexes or lipopolyplexes) with nucleic acids via electrostatic interactions and allow them to pass through the cell membranes.

Among the main known cationic lipids, the following can in particular be mentioned, in a non-exhaustive manner and by way of examples:

monovalent cationic lipids in the form of quaternary ammonium salts, such as DOTMA (N-[1-(2,3-dioleyloxy)propyl]-N,N,N-trimethylammonium chloride) (Feigner, P. L. et al. (1987) *Proc. Natl. Acad. Sci. USA* 84 (21), 7413-7417) marketed in combination with a neutral lipid, DOPE (dioleoylphosphatidylethanolamine), under the name of Lipofectin™; metabolizable DOTMA analogues such as DOTAP (1,2-dioleoy-3-trimethylammonium propane) (Leventis, R. and Silvius, J. R. (1990) *Biochim. Biophys. Acta* 1023, 124-132); DMRIE (Feigner, J. H. et al. (1994), *J. Biol. Chem.* 269(4), 2550-2561); or also DDAB (dioctadecyldimethyl ammonium bromide), marketed in combination with a neutral lipid under the name of TransfectACE™;

monovalent cationic lipids in the form of pyridinium salts such as SAINT-2 (N-methyl-4-(dioleyl)methylpyridinium chloride) (Ruiters, M. H. J., PCT WO2006/043809);

multivalent cationic lipids in the form of lipospermines such as DOGS (5-carboxyspermylglycine-dioctadecylamine) (Behr, J.-P. et al. (1989) *Proc. Natl. Acad. Sci. USA* 86 (18), 6982-6986) and DOSPA (2,3-dioleyloxy-N-[2(sperminecarboxamido)ethyl]-N,N-dimethyl-propanammonium trifluoroacetate), supplied under the respective trade names of Transfectam™ and Lipofectamine™;

multivalent cationic lipids in the form of lipopolylysines (Zhou, X. et al. (1991) *Biochem. Biophys Acta.* 1065, 8-14);

cholesterol cationic derivatives such as DC-Chol (3β[N—(N'—N',-dimethylaminomethane)-carbamoyl]cholesterol) (Gao, X. & Huang, L. (1991) *Biochem. Biophys. Res. Commun.* 179 (1), 280-285).

The delivery of nucleic acids by formulated cationic lipids (lipofection) has numerous advantages as they are not immunogenic, unlike viral agents, are simple to use, make it possible to deliver nucleic acids without a size limit, and can be produced in large quantities. Furthermore, lipofection is the method most used in research laboratories for transfecting cells in vitro due to its ease of use, its efficacy in the presence or absence of serum for a large variety of cell types, in particular adherent cells and its versatility for the delivery of nucleic acids.

However, these synthetic vectors are poorly or not at all effective for the transfection of certain cell types, in particular cells in suspension such as lymphocytes, stem cells, primary cells (non-dividing) etc. The reduced efficacy of the cationic lipids in transfecting certain cells such as cell lines in suspension is explained by a poor ability of the lipoplexes to become attached to the surface of these cells. In fact, unlike adherent cells, the latter possess very few polyanionic transmembrane proteins such as Heparan Sulphate Proteoglycans (HSPGs) which are the main points for anchoring the lipoplexes onto the plasmic membranes (Kopatz, I. et al. (2004) *J. Gene Med.* 6, 769-776; Wiethoff, C. M. et al. (2001) *J. Biol. Chem.* 276, 32806-32813; Mislick K. A. et al. (1996) *Proc. Natl. Acad. Sci. USA* 93, 12349-12354). Nevertheless, various approaches using specific ligands such as transferrin (Kursa, M. (2003) *Bioconjugate Chem.* 14, 222-231; Kakudo, T. et al. (2004) *Biochemistry* 43, 5618-5628), epidermal growth factor (EGF), monoclonal antibodies (Guillem, V. M. et al. (2002) *J Controlled Released* 83, 133-146; Guillem, V. M. et al. (2002) *J. Gene Med.* 4, 170-182; Puls, R. L. et al. (1999) *Gene Ther.* 6, 1774-1778; Thurnher, M. et al. (1994) *Glycobiology* 4 (4), 429-435) or peptides (Wagner, E. (1999) *Adv. Drug Deliv. Rev.* 38 (3), 279-289; Uduehi A. et al. (2003) *Biotechnol. Appl. Biochem.* 38, 201-209), coupled or combined with a cationic polymer or a co-lipid formulated with cationic lipids, have been successfully tested. Quiescent cells are also very difficult to transfect using lipofection, as in the absence of means for targeting the nucleus such as nuclear localization sequences, the complexes present in the cytosol have difficulty in passing through the pores of the nuclear membrane and thus being transcribed. Several approaches using ternary complexes (lipoplexes: cationic lipids and nucleic acids plus a nuclear targeting element) based on histones, peptide nuclear localization sequences, have been studied in order to get round this problem (Khalil I. A. (2006) *Pharmacol. Rev.* 58, 32-45; Medina-Kauwe, L. K. (2005) *Gene Ther.* 12, 1734-1751; Escriou, V. et al. (2003) *Adv. Drug Deliv. Rev.* 55 (2), 295-306; Ma, H. et al. (2001) *Curr. Pharm. Biotechnol.* 2 (1), 1-17; Hagstrom, J. E. (1996) *Biochim. Biophys. Acta* 1284 (1), 47-55).

However, the addition of these targeting elements to the cationic lipids makes the formulation and preparation of the complexes difficult and their use is thus very limited. Furthermore, their efficacy in vitro and in vivo remains uncertain.

As a result, the development of new cationic lipids incorporating the nucleic acid complexing and targeting functions in the same molecule would make it possible to dispense with the use of additional targeting elements (membrane and nucleus) and would provide a solution to these major obstacles.

Moreover, the in vivo efficacy of lipofection remains too low (Evans, C. H. et al. (2006) *Adv. Drug Deliv. Rev.* 58, 243-258) and new more efficient lipids are necessary. Their in vivo application is limited by the enzymatic degradation of the complexes, their pharmacology and by the presence of proteins and polysaccharides in the body fluids and mucus, which strongly inhibit transfection. The main parameters which affect lipoplex transfection efficacy have been widely studied (Solodin, I. et al. (1995) *Biochemistry* 34 (41), 13537-13544; Templeton, N. S. et al. (1997) *Nat. Biotech.* 15 (7), 647-652; Thierry, A. R. et al. (1995) *Proc. Natl. Acad. Sci. USA* 92 (21), 9742-9746; Li, S. et al. (1997) *Gene Ther.* 4 (9), 891-900; Liu, Y. et al. (1997) *Nat. Biotechnol.* 15 (2), 167-173; Liu, F. et al. (1997) *Gene Ther.* 4 (6), 517-523; Song, Y. K. et al. (1997) *Hum. Gene Ther.* 8 (13), 1585-1594; Hong, et al. (1997) *FEBS Letters* 400 (2), 233-237). These studies have shown that the best levels of in vivo gene expression were obtained using relatively high lipid/nucleic acid ratios.

Nevertheless, the use of a large excess of cationic lipids or lipoplexes is often accompanied by significant toxicity.

Thus, the cytotoxicity of the cationic lipids remains one of the major drawbacks of this method, both in vitro and in vivo. It is chiefly due to poor biodegradability of the cationic lipids which are not naturally present in the cells. Numerous efforts have been made to address this. Thus, Scherman's team developed lipids having a bond sensitive to the reducing medium in the fatty chains in order to facilitate their metabolism (WO 9938821). On the other hand, Boomer et al. incorporated a vinyl ether group, which is sensitive to the pH, and more particularly to the acid medium, in the spacer arm of their cationic lipid in order to induce rapid cleavage of the lipid in the acid medium of the endosomes. This cleavage leads to a destabilization of the structure of the lipoplexes which are embedded in the membrane of the endosomes and allows early release of the DNA from the endosomes towards the cytosol before the latter is degraded by the nucleases (Boomer, J. A. (2002) *Gene Transfer Pharm. Res.* 19 (9), 1292-1301). With the same aim, Szoka's team constructed a family of cationic lipids provided with a spacer arm containing a linear or cyclic orthoester group, which is stable at physiological pH, and which is hydrolyzed at acid pH (Chen, H. et al. (2007), *J. Med. Chem.* 50 (18), 4269-4278). Finally, the presence of ester groups in the cationic lipids allows a better biodegradability of the latter in the cells, as the ester groups are easily cleaved by the endogenous esterases. There are numerous examples of cationic lipids containing ester groups among which there can be mentioned the DMTM (Gly) and DOTM(Gly) tetraesters synthesized by Nantz's team, the influence of which on the reduction of cytotoxicity has been studied (Aberle, A. M. et al. (1998) *Biochemistry* 37 (18), 6533-6540).

All these lipids have shown better biodegradability in intracellular medium, inducing very low cytotoxicity. Nevertheless, these entities have not incorporated the targeting elements described previously and thus have a reduced efficacy on non-mitotic cells in suspension. This is why it is necessary to design novel lipids which are completely biodegradable in cells and which contain the abovementioned targeting elements.

At present there are a large number of commercial cationic lipids (transfection reagents) developed specifically for transporting nucleic acids. The transfection procedures using these reagents are commonly used in most biomedical laboratories. Curiously, far less progress has been made in the design of reagents dedicated to the transport of other biomolecules such as peptides and proteins, despite considerable resources devoted to the isolation and evaluation of peptides, antibodies, antigens and recombinant proteins. In fact, all the recombinant proteins and monoclonal antibodies currently used for clinical purposes are directed towards an extracellular, not intracellular target (Krejsa, C. et al. (2006) *Nat Rev Drug Discov* 5, 507-521). If there were an effective method for delivering peptides, proteins or any other biomolecules inside cells, it would not be necessary to restrict potential candidates for therapeutic treatment to secreted or membrane molecules. The direct introduction of peptides and/or proteins into the cells can be useful in various fields such as cell cycle regulation, apoptosis control, immunology and transcription regulation. This approach can thus allow researchers to study the function of the transported molecules, to block or induce an intracellular function in living cells, to develop their potential therapeutic use against a large number of diseases as diverse as cancer, inflammations and infections as well as to develop new vaccines. For example, the transport of monoclonal antibodies into cells can be used to specifically block an intracellular target. This approach has already been demonstrated via the transfection of DNA coding for antibodies ("Intrabodies") (Mhashilkar, A. M. et al. (1997) *J Virol* 71, 6486-6494; Chen, S. Y. et al. (1994) *Hum Gene Ther* 5, 595-601; Shaki-Loewenstein, S. et al. (2005) *J Immunol Methods* 303, 19-39; Williams, B. R. et al. (2006) *Curr Med Chem* 13, 1473-1480). However, this strategy is time-consuming and labour-intensive, and the direct transport of recombinant antibodies may prove to be a much more attractive method as these antibodies are in particular very easy to produce in large quantities.

Several approaches for transporting peptides, proteins and other functional biomolecules into cells have been studied. Microinjection and electroporation have been used to introduce functional proteins inside cells with varying degrees of success (Marrero, M. B. et al. (1998) *J. Biol. Chem.* 270, 15734-15738; Fenton, M. et al. (1998) *J. Immunol. Methods* 212, 41-48; Abarzua, P. et al. (1995) *Cancer Res.* 55, 3490-3494). The most studied approach for transporting macromolecules, peptides or proteins into cells uses a special class of peptides and/or proteins having the ability to pass through the cell membranes by a so-called transduction mechanism. (Schwarze, S. R. et al. (2000) *Trends Cell Biol.* 10, 290-295; Murriel, C. L. et al. (2006) *Expert Opin Drug Deliv* 3, 739-746). This is in fact a short peptide sequence rich in basic residues (essentially lysines and arginines) called PTD ("Protein Transduction Domain") or CPP ("Cell-Penetrating Peptides") which confers upon these proteins the property of translocating through the cell walls and also reaching the cell nuclei. The main three examples of PTDs are the HIV-1 TTA (Trans-activating transcriptional activator) proteins: (Green, M. et al. (1988) *Cell* 55, 1179-1188; Frankel, A. D. et al. (1988) *Cell* 55, 1189-1193), HSV-1 VP22 (Herpes Simple Virus Type I VP 22 Transcription Factor) (Elliott, G. et al. (1997) *Cell* 88, 223-233) and Antp (Drosophila Antennapedia Homeotic Transcription Factor) (Joliot, A. et al. (1991) *Proc. Natl. Acad. Sci. USA* 88, 1864-1868).

However, one of the main limitations of the use of PTDs is the need to form a covalent bond, either by chemical route, or by cloning, between the PTD sequence and the molecule of interest, which is not without consequences on the biological activity of the latter. For example, it can lead to a modification of the conformation of the protein or also interfere with its function by steric hindrance.

Furthermore, the efficacy of these systems is highly dependent on the structure and size of the molecule to be transported. They are very effective in the case of peptides or small soluble proteins exhibiting structural versatility, but limited in the case of complex and multimeric systems.

Thus, the PTDs are not effective for transporting DNA, unlike the cationic lipids. Therefore, scientists currently have to use methods which are sophisticated, time-consuming and limited in their application for the intracellular transport of biologically active molecules. At present, the indirect method consisting of transfecting a DNA coding for a protein remains the most used method for obtaining this protein in cells.

There is therefore a crucial need to develop a simple and robust system of transport, similar to the transfection agents, for the intracellular delivery of peptides, proteins, antibodies and other biomolecules.

In fact, a lipidic formulation making it possible to combine proteins and other molecules rapidly and non-covalently, to protect the latter from the biological environment and to transport them inside the cells without a size limit or without altering their function would provide an undeniable benefit in all aspects of cell biology, genomics, functional genomics and proteomics. Now, the majority of the cationic lipids used in transfection prove to be completely ineffective for transporting other biomolecules inside the cells. Nevertheless, a few examples have been reported on the use of cationic lipids for transporting proteins into the cells (Debs, R. J. et al. (1990), *J. Biol. Chem.* 265, 10189-10192; Baubonis, W. et al. (1993) *Nucleic Acids Res* 21, 2025-2029; Huang, L. et al. *Biochem. Biophys. Res. Commun.* 217, 761-768; Farhood, H. et al. (1995) *Anal. Biochem.* 225, 89-93; Guillaume, C. et al. (2000), *J. Pharm. Sci.* 89, 639-645; Sells, M. A. et al. (1995) *BioTechniques* 19, 72-78; Walker, C. et al. (1992) *Natl. Acad. Sci. USA* 89, 7915-7918; Zelphati, O. et al. (2001) *J Biol Chem* 276, 35103-35110; Dalkara, D. et al. (2004) *Mol Ther* 9, 964-969). Lipofectin, DC-Chol and TransACE have been used for co-transporting DNA combined with proteins (Baubonis et al. (1993); Debs et al. (1990); Farhood et al. (1995)). However, their efficacy remains very low, and has required the addition of lysosomotropic agent (Debs et al. (1990)). Furthermore, the role of these cationic lipids remains questionable, the proteins used being able to enter cells by themselves (Farhood et al. (1995); Huang et al. (1995)). Walker et al. have also used a cationic lipid (DOTAP) to transport an antigen into cells, but it is difficult to distinguish between the presentation of the antigen inside or outside the cells and the functionality of the transported protein is not demonstrated (Walker et al. (1992)). Phosphonocationic lipids (GLB73 and GLB43) have also been used in vitro and in vivo for transporting β-galactosidase, but without demonstrating the influence of the lipids on the number of β-galactosidase-positive cells, no other functional protein having been tested moreover (Guillaume et al. (2000)). In most of the abovementioned examples, the efficacy of transport was evaluated after fixation and permeabilization of the cells, which complicates the interpretation of the results. More recently, Zelphati et al. have developed a trifluoroacetylated cationic lipid for the intracellular vectorization of proteins (Zelphati et al. (2001)). The latter has made it possible to transport a certain number of biologically active proteins into living cells and proved more effective than numerous commercial cationic lipids. Similar studies were then carried out with the lipids DOGS and Chol-Sper (Dalkara, D. et al. (2006) *J Control Release* 116, 353-359; Dalkara et al. (2004)). Up to the present, the use of cationic lipids seems less well-suited to the transport of proteins than to the transport of nucleic acids, inter alia because there is still no known lipidic system which allows the delivery of proteins in the presence of serum.

Thus, the intracellular vectorization of proteins, peptides and other molecules, apart from the nucleic acids, remains an extremely isolated and limited approach.

Although there are a certain number of commercial products based on cationic lipids, which are effective for the delivery of nucleic acids into cells in culture, and a few more especially developed for transporting proteins, none of these is suitable for transporting all the types of biomolecules in the presence of serum. Moreover, these transfection agents are relatively ineffective on primary cells in suspension and are often accompanied by high toxicity which limits their action in vivo.

A subject of the present invention is to provide a novel universal family of cationic lipids, which are compatible with the presence of serum and are non-toxic, allowing an effective in vitro, ex vivo and in vivo delivery of all types of biomolecules such as nucleic acids, peptides, proteins, polysaccharides and lipids into living cells.

In fact, the innovative structure of these new cationic lipids makes it possible to combine:

1. the amphiphilic properties of the cationic lipids in order to form organized structures (liposomes, micelles etc.) allowing the transport and vectorization of active molecules towards their target, their properties of forming non-covalent complexes with negatively charged nucleic acids (lipoplexes), and their properties of destabilizing the cell membranes.

2. the properties of the cationic head, constituted by basic amino acids present in the PTDs, known for their ability to become attached to cells and pass through the transmembrane barriers including the nuclear barrier. Moreover, these sequences of basic amino acids naturally interact with several types of biomolecules including nucleic acids, peptides and proteins and are completely non-toxic. Moreover, these new compounds are capable of transfecting cells with a great efficacy in the presence of serum due to their low capacity for interacting with the components of the serous medium.

3. the ability to degrade rapidly in intracellular medium due to the presence of a spacer arm between the lipophilic part and the cationic head provided with a functional group incorporating a bond sensitive to its environment (pH, oxidation-reduction, enzymes etc.) which can be cleaved in cytosolic medium. The compounds originating from the resultant degradation are natural molecules (fatty acids, natural amino acids) which are easily metabolized by the cell. The biodegradable character of these molecules makes them non-cytotoxic as a result.

In order to achieve this aim, a subject of the invention is a cationic amphipathic compound of formula (I):

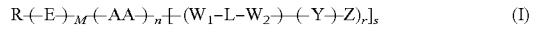

(I)

in which:

R represents a lipophilic region which can comprise
  one or more branched or linear, unsaturated or saturated, optionally fluorinated alkyl chains, comprising 6 to 24 carbon atoms, preferentially between 10 and 18 carbon atoms; or
  one or more cyclic or polycyclic groups known to be lipophilic such as a steroid group (for example a cholesterol derivative), a polyaromatic group (for example a naphthalene, dansyl or anthracene derivative), or an alkaloid derivative group; or
  a natural or synthetic lipid.

Optionally, R can be constituted by a combination of these different groups. R can comprise one or more heteroatoms.

E represents a linear or branched hydrocarbon group, which can comprise from 1 to 15 carbon atoms, preferentially from 1 to 8, and which can optionally comprise one or more heteroatoms;

m is an integer equal to 0 or 1;

AA represents an amino acid radical;

n is an integer equal to 0 or 1;

$W_1$ and $W_2$, identical or different, represent a linear or branched hydrocarbon group which can comprise from 1 to 15 carbon atoms, preferentially from 1 to 6, which can optionally comprise one or more heteroatoms;

L represents a functional group which can incorporate at least one bond which is sensitive to its environment, which is stable in extracellular medium and rapidly cleaved in the intracellular medium as it is sensitive to stimuli such as pH reduction (for example vinyl ether or acylhydrazone groups sensitive to acid medium) or a change in the oxidation-reduction potential (for example a disulphide bond, cleaved in reducing medium), to enzymes (for example an ester bond, cleaved by endogenous esterases); or also to light radiation (bearing photosensitive groups for example);

p is an integer equal to 0 or 1;

Y is a branched hydrocarbon group which can comprise from 1 to 20 carbon atoms, preferentially from 1 to 12, and/or one or more heteroatoms, and which can optionally be covalently coupled with the $W_2$ or AA or E or R group on the one hand, and to at least two Y and/or Z groups on the other hand;

q is an integer comprised between 0 and 8, preferably between 0 and 3;

Z represents a basic amino acid or serine;

r is an integer comprised between 1 and 16, preferably between 1 and 8, it being understood that if q is equal to 1 then r is at least equal to 2 and that if r is greater than 1, then the Z groups can be identical or different;

s is an integer equal to 1 or 2;

and its physiologically acceptable addition salts

In the above and hereafter, unless otherwise indicated, by "heteroatom" is meant an atom chosen from nitrogen, oxygen, sulphur and halogens such as for example bromine, iodine, chlorine and fluorine.

Concerning $W_1$ and $W_2$, when identical or different, they represent a linear or branched hydrocarbon group which can comprise from 1 to 15 carbon atoms, preferentially from 1 to 6, comprising one or more heteroatoms, the heteroatom or heteroatoms can be chosen from nitrogen, oxygen, sulphur and the halogens such as for example bromine, iodine, chlorine and fluorine, preferentially from nitrogen, sulphur and the halogens such as for example bromine, iodine, chlorine and fluorine.

Similarly, by "amino acid radical" is meant, the group of atoms which consists of this amino acid when the latter is covalently bonded, on the one hand to the E or R group, and on the other hand to one or more $W_1$ or Y or Z groups.

Similarly also, by "hydrocarbon group" is meant any group comprising one or more carbon atoms, optionally bonded to one or more hydrogen atom(s).

According to a first preferred provision of the invention, in formula (I), R preferably corresponds to formula (II):

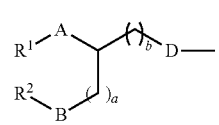

(II)

in which:

$R^1$ and $R^2$, identical or different, represent a linear, branched and/or cyclic, saturated or unsaturated, hydrocarbon group comprising from 6 to 24 carbon atoms, preferentially from 10 to 18.

A and B, identical or different, represent a —C(O)—O—; —O—C(O)—; —CO—NH—; —NH—CO—; —NH— or —O— group.

a is an integer comprised between 1 and 6, preferably a is an integer equal to 1 or 2.

b is an integer comprised between 0 and 6, preferably b is an integer equal to 0 or 1.

D represents an —NH—, —CO—, —O— or —S— group.

Among the structures corresponding to formula (II), R preferentially corresponds to formula (III) (Example I.1 below):

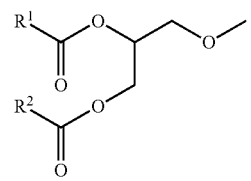

(II)

or also to formula (IV) (Example I.8 below):

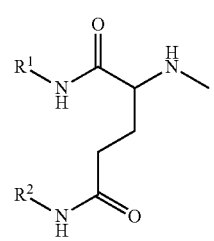

(IV)

in which $R^1$ and $R^2$ have the same meaning as previously.

In formulae (III) and (IV), $R^1$ and $R^2$ preferably represent a $C_{12}$ to $C_{18}$ alkyl, alkenyl or alkynyl chain.

According to another preferred provision of the invention, in formula (I), E can be absent or E can serve as a spacer arm and then corresponds to formula (V): -$G_1$-$X_1$-$G_1$-, in which $X_1$ represents a bridging alkylene group which can comprise from 1 to 8 carbon atoms, preferentially from 1 to 4, whilst $G_1$ can represent a —CO— or —NH— group.

Among the compounds according to the invention, E preferably corresponds to the formula CO—$X_1$—CO in which $X_1$ has the same meaning as previously and is connected by an amide bond to the lipophilic region R on the one hand, and either to the AA radical, or directly to the $W_1$ or Y or Z group on the other hand.

According to the invention, the amino acid, the radical of which is denoted AA in formula (I), can preferably be chosen from the twenty amino acids which make up proteins, namely aspartic acid, glutamic acid, alanine, arginine, asparagine, cysteine, glutamine, glycine, histidine, isoleucine, leucine, lysine, methionine, phenylalanine, proline, serine, threonine, tyrosine, tryptophan and valine. In particular, AA can be chosen from aspartic acid, glutamic acid, isoleucine, leucine, lysine and phenylalanine, aspartic acid (Example I.14), glutamic acid (Example I.15) and lysine (Example I.12) being particularly preferred. However, this amino acid can also be chosen from rarer amino acids such as for example, β-alanine, γ-aminobutyric acid, α-aminoadipic acid, hydroxyproline, hydroxylysine, phenylserine, α,ε-diaminopimelic acid, ornithine and any other modified amino acids, any amino acid being suitable since it comprises, by definition, two functional groups, one being carboxylic acid, the other amine, allowing it to bind covalently, on the one hand to the spacer arm E or to R and, on the other hand, to at least one $W_1$ or Y or Z group. The choice of the amino acid depends in particular on the value that it is desired to give to s in formula (I), to the extent that it must comprise at least three functional groups for s to be able to be equal to 2, whilst it is sufficient for it to comprise only two functional groups to have s equal to 1. According to the invention, it is preferred that AA is an amino acid radical belonging to the L series. However, it is also possible that AA is an amino acid radical of the D series.

According to another preferred provision of the invention, in formula (I), $W_1$ can correspond to formula (VI): $-G_2-X_2-$ and $W_2$ can correspond to formula (VII): $—X_3-G_3-$ in which $X_2$ and $X_3$, identical or different, can represent a bridging alkylene group which can comprise from 1 to 8 carbon atoms, preferentially from 1 to 4, whilst $G_2$ and $G_3$, identical or different, can represent a —CO—, —NH— or —O— group. $W_1$ forms a covalent bond with an AA, E or R group on the one hand, and with the L group on the other hand, whilst $W_2$ forms a covalent bond with an L group on the one hand, and with a Y or Z group on the other hand.

According to another preferred provision of the invention, in formula (I), L can represent an ester (—CO—O—), disulphide (—S—S—), vinyl ether (—O—C=C—), acylhydrazone (—CO—NR—N=CR'R") group, the ester (Example I.1) and disulphide groups (Example I.6) being particularly preferred. These groups form a covalent bond with the $W_1$ group on the one hand and the $W_2$ group on the other hand.

According to another preferred provision of the invention, in formula (I), Y preferably corresponds to formula (VIII): —CO—$X_4$—NH—$X_5$—N—[$X_6$—NH]$_2$— or (IX): —NH—$X_5$—N—[$X_6$—NH]$_2$—, in which $X_4$, $X_5$ and $X_6$, identical or different, can represent a bridging alkylene group which can comprise from 1 to 8 carbon atoms, preferentially from 1 to 4. In formulae (VIII) and (IX), $X_4$ preferably represents a methylene, whilst $X_5$ and $X_6$ can preferably represent a bridging alkylene group comprising from 1 to 4 carbon atoms and, better still, 2 carbon atoms. Y therefore possesses three functional groups making it possible for it to form a covalent bond with optionally $W_2$ or AA or E or R on the one hand, and at least two Y and/or Z groups on the other hand.

According to another preferred provision of the invention, in formula (I), Z represents a basic amino acid preferably chosen from lysine (Example I.1), ornithine (Example I.6), arginine (Example I.7), histidine (Example I.4). The amino acid Z possesses a carboxylic acid function which allows it to form a covalent bond optionally with Y or $W_2$ or AA or E or R on the one hand, and one or two basic reactive functions (amine, alcohol etc.) making it possible to form a covalent bond optionally with one or two other Z groups on the other hand. According to the invention, it is preferable for the basic amino acid to belong to the L series. However, it is also possible or it to belong to the D series.

According to the invention the cationic amphipathic compound of formula (I) can be in solution in the form of salt; the counter-ion can then be a physiologically acceptable organic or inorganic anion, advantageously chosen from organic anions such as $CF_3COO^-$ and $CH_3CO^-$ or inorganic anions such as $Br^-$, $Cl^-$, $I^-$ and $F^-$.

Among the compounds of formula (I) which are suitable for the purposes of the invention, there can be mentioned, non-exhaustively, the compounds the formulae of which are as follows:

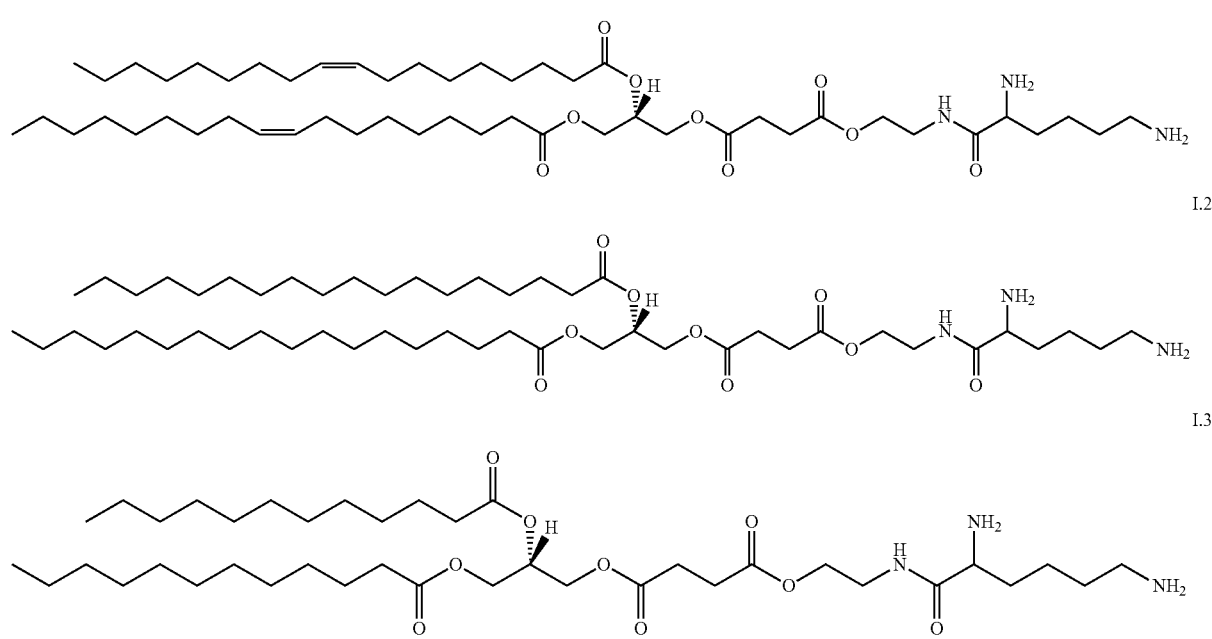

-continued
I.4
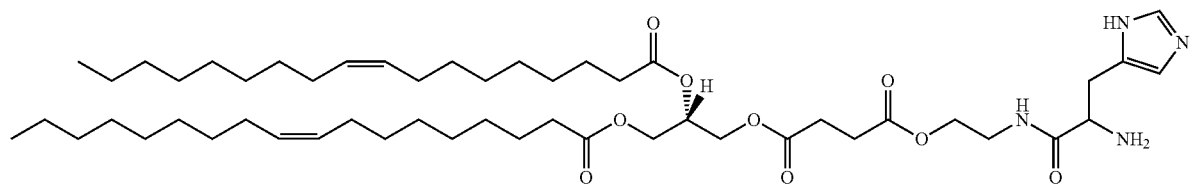
I.5
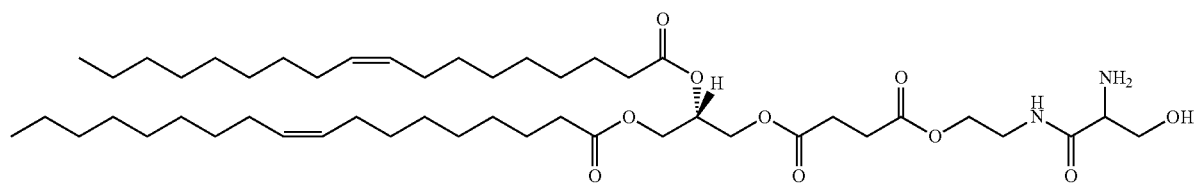
I.6
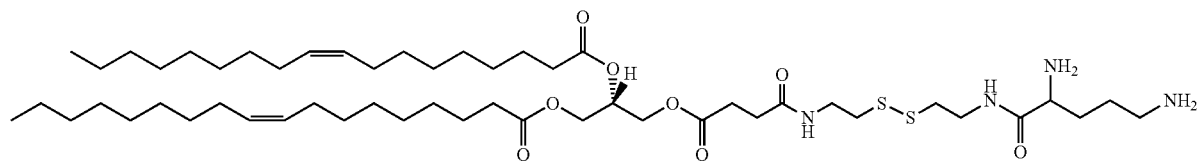
I.7
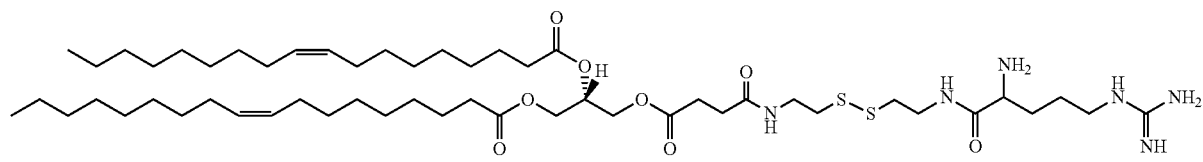
I.8
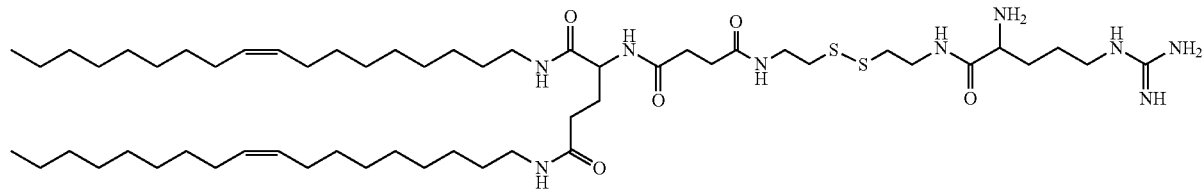
I.9
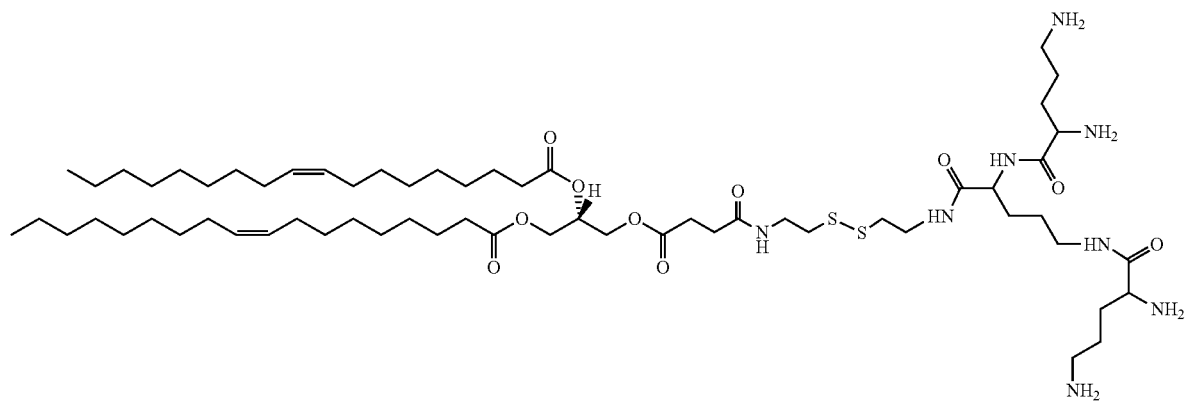

I.10
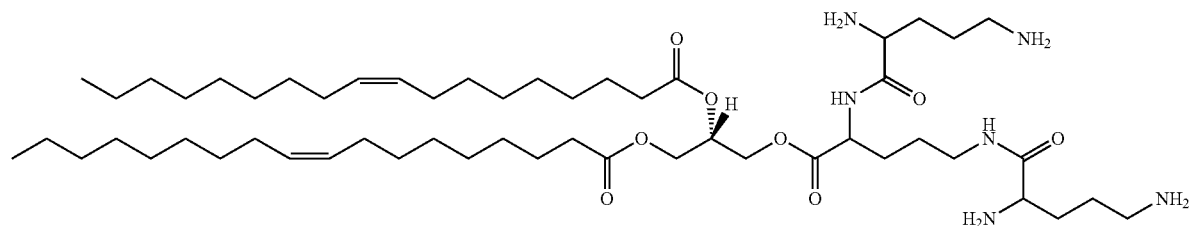
I.11
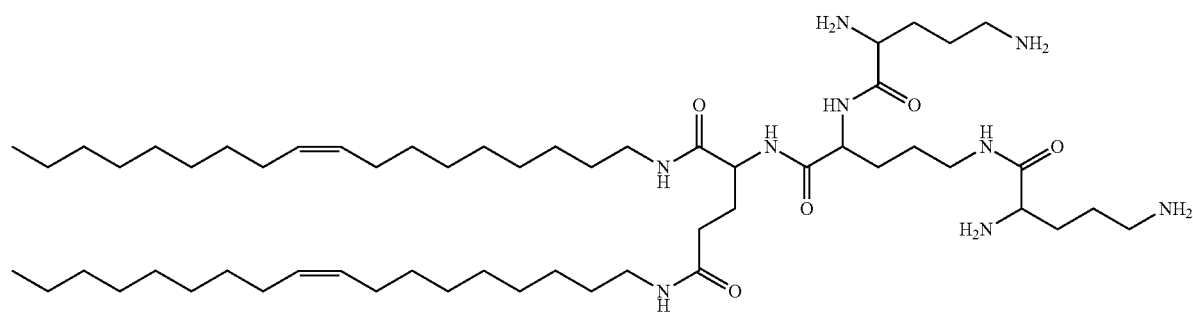
I.12
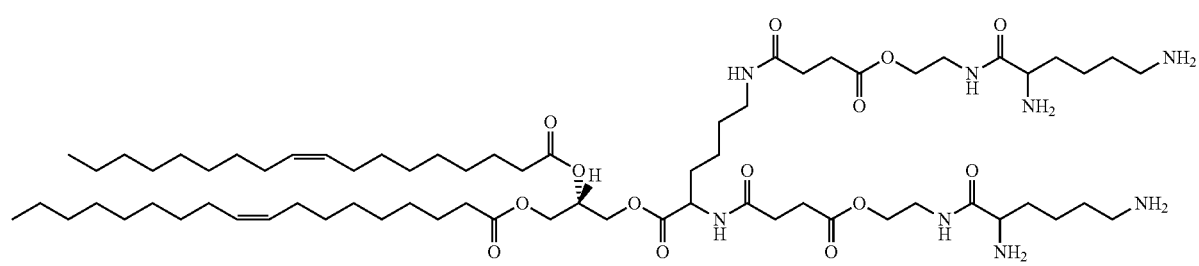
I.13
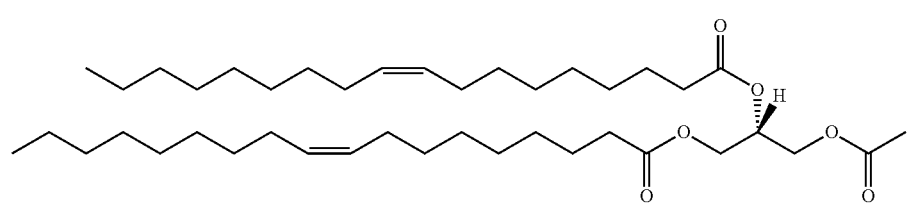

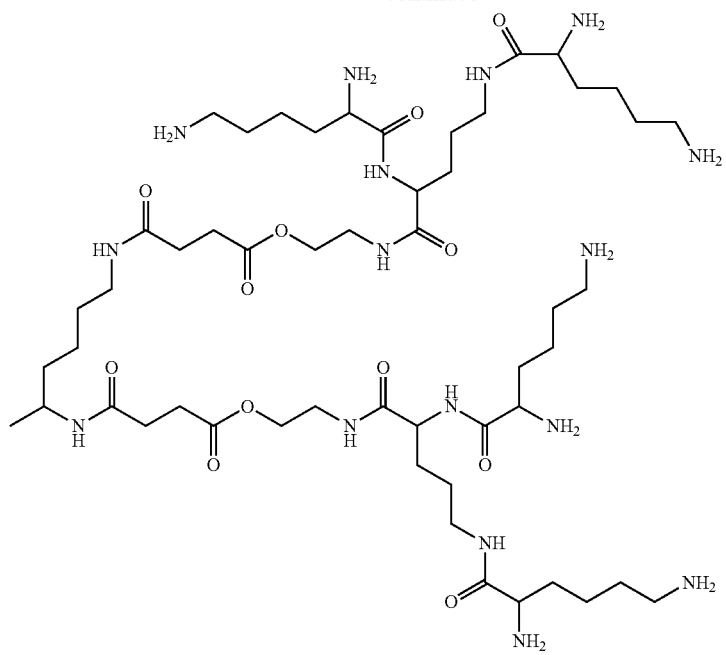
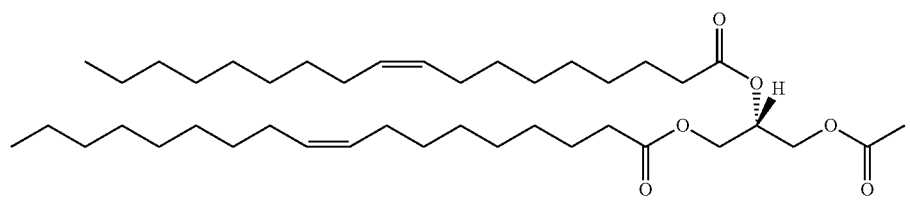
I.14
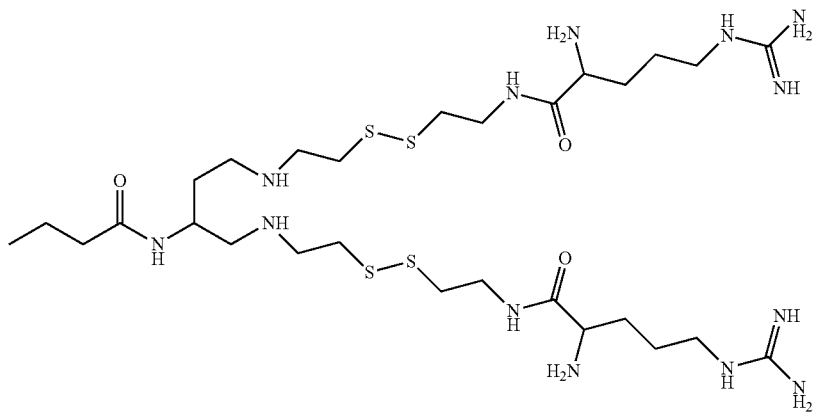
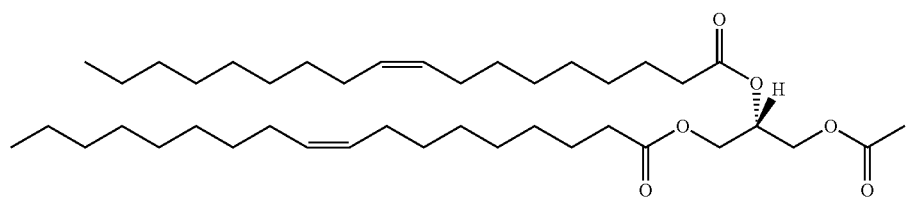
I.15

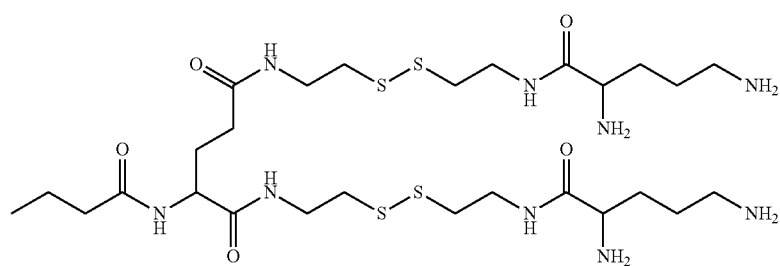
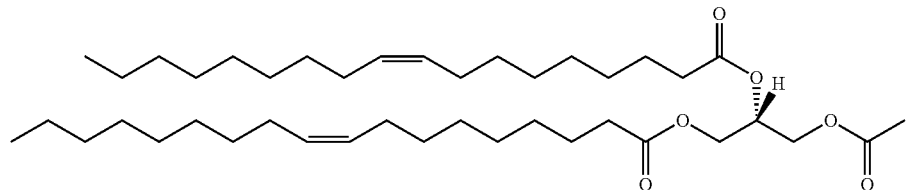
I.16
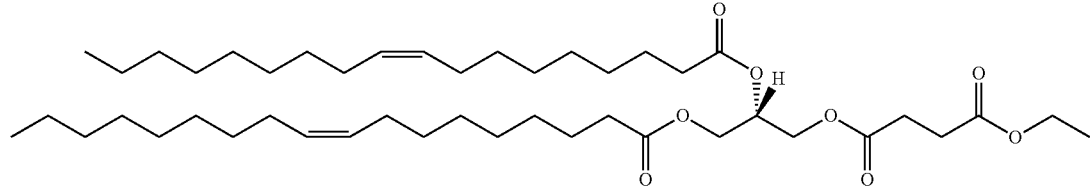
I.17
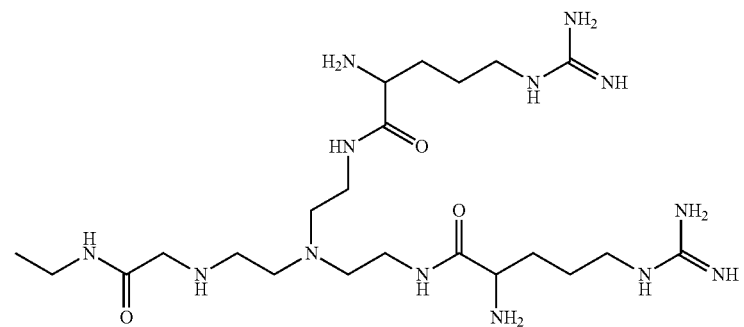
I.18
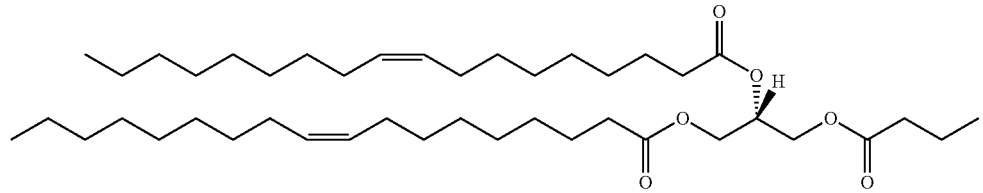

-continued
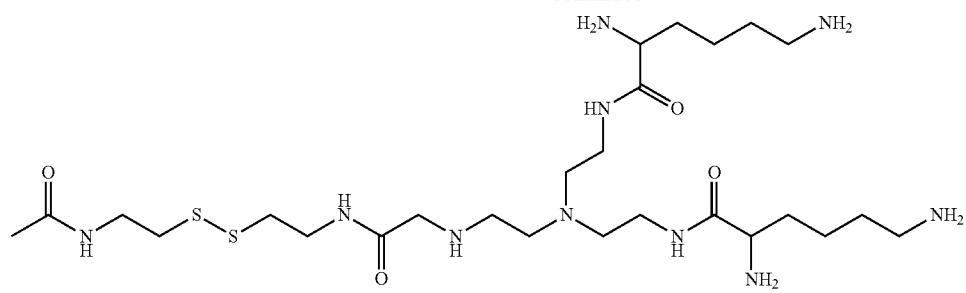
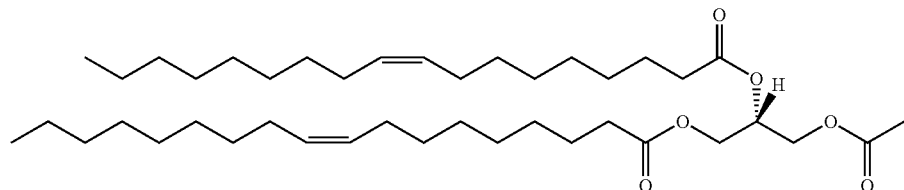
I.19
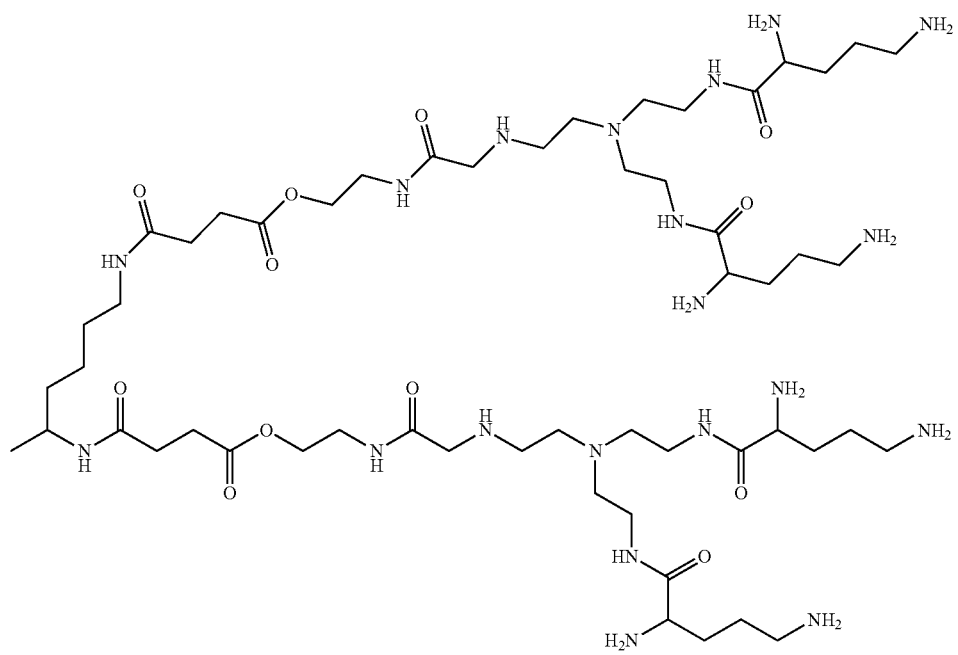
I.20
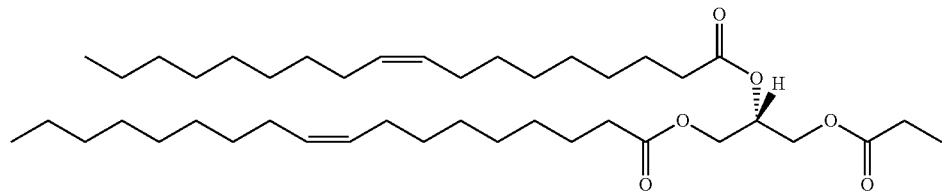

-continued

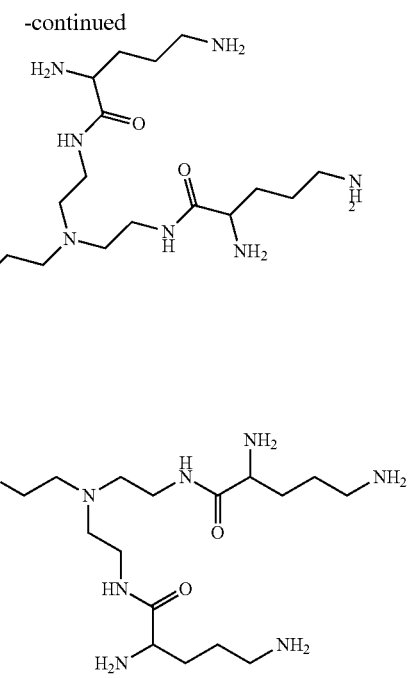

Figure 2:
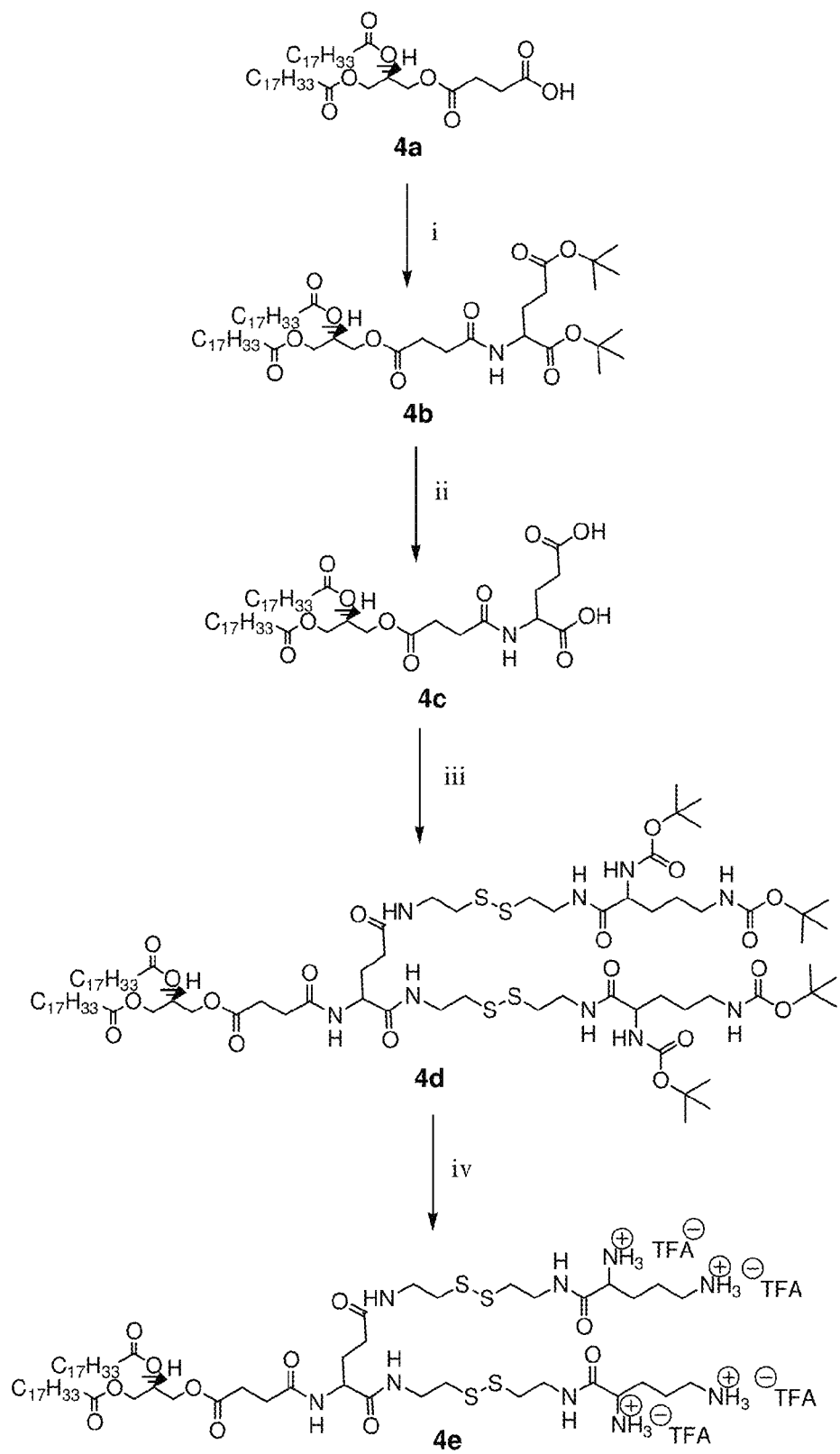
Figure 3:
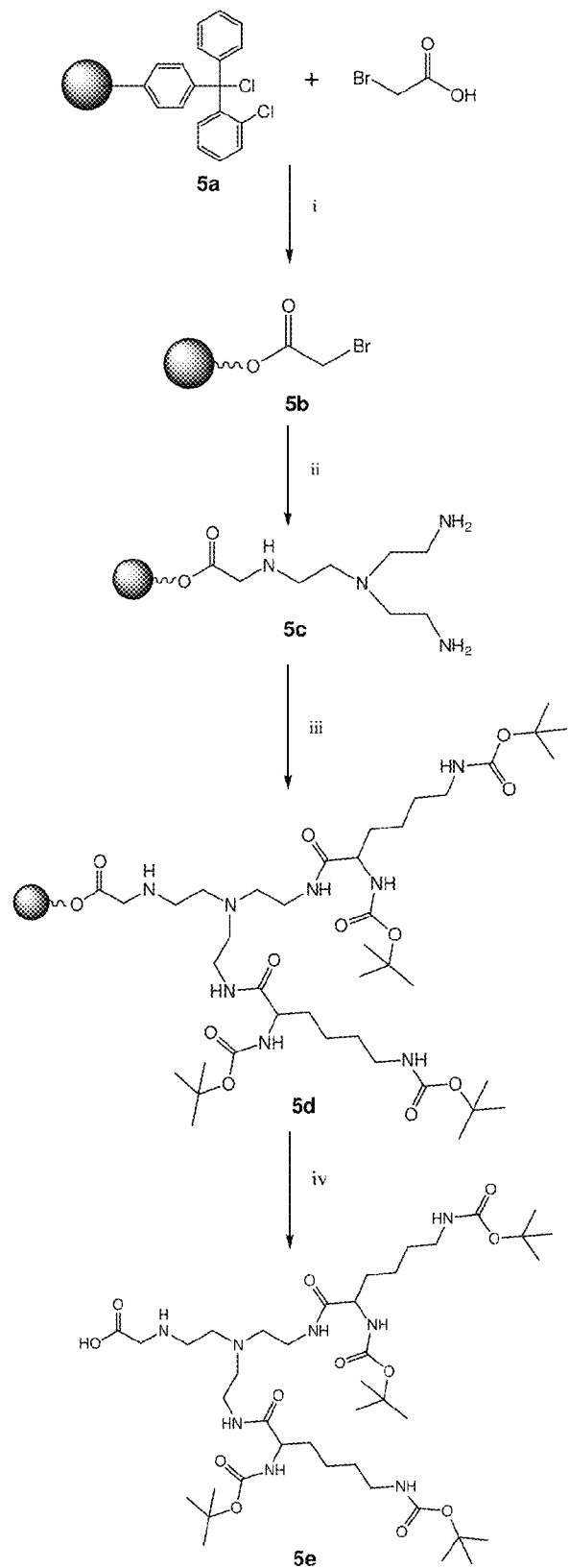

The compounds according to the invention can be prepared from starting materials which can easily be obtained commercially, using synthesis and purification methods well known to a person skilled in the art. The reaction diagrams for the preparation of certain preferred compounds of the present invention are illustrated in FIGS. 1 to 3 and the preparation methods of these compounds are described in detail in the examples below. Moreover, a synthesis method on a solid support (Byk G. et al. (1997) *Tetrahedron Lett.* 38 (18), 3219-3222) has been used for the preparation of certain basic amino polyacids as synthesis intermediates for the preparation of compounds of the invention. This method is described in detail in one of the examples below and the reaction diagram is illustrated in FIG. 3.

The compounds suitable for the purposes of the invention are obtained in the form of salts which can be prepared by standard techniques, as illustrated for example in the reaction diagrams in FIGS. 1 and 2. In these examples, the stage of formation of trifluoroacetate salts also correspond to a stage of deprotection of the amine and/or guanidine functions of the basic amino acids borne by the compounds of the invention.

Another subject of the invention relates to compositions comprising at least one compound corresponding to formula (I), particularly cosmetic and/or pharmaceutical compositions, or also laboratory reagents.

Yet another subject of the invention relates to a composition comprising a compound corresponding to formula (I) as defined previously, also called a transfer agent, and at least one nucleic acid or a polynucleotide. Preferentially, the transfer agent and the nucleic acid can be present in quantities such that the ratio of positive charges of the agent to the negative charges of the nucleic acid can be comprised between 0.1 and 50, preferentially between 0.5 and 20. This ratio can be easily adjusted by a person skilled in the art depending on the agent used, the nucleic acid and the type of cells to be transfected. Advantageously, according to the invention, the composition can comprise a quantity of transfer agent comprised between 1 and 12 nanomoles per μg of nucleic acid, and preferably between 1 and 9 nanomoles of transfer agent per μg of nucleic acid.

For the purposes of the present invention, the nucleic acid can be a deoxyribonucleic acid (DNA) or a ribonucleotide acid (RNA) or a modified nucleic acid such as a peptide nucleic acid (PNA), morpholino oligonucleotides or aptamers. Its origin is not significant: natural or artificial. It can be of animal, human, plant, bacterial or viral origin. Its function as a therapeutic agent can be a gene coding for a polypeptide and/or a protein of interest in a host cell or can be an antisense function controlling the expression of a gene, its transcription to RNA or its translation to protein. It can also act as a ribozyme or interfering RNA (sRNA or shRNA or miRNA) with the expression of a gene.

In a particular aspect the nucleic acid encodes in an effective manner for a polypeptide of pharmaceutical interest which, during its expression in the host cell, makes it possible to remedy a malfunction of the receiving organism. As a result a composition according to the invention is useful in in vitro and in vivo research and development or in in vivo and ex vivo gene therapy. The nucleic acid can also encode in an effective manner for a polypeptide capable of producing an immune response against it in humans or animals or of inducing an immune response. As a result, a composition according to the invention finds a particular application in gene therapy, the field of vaccines, and of immunotherapy, in particular for treating or preventing cancers or bacterial or viral infections.

For use in the fields of gene therapy, vaccines and immunotherapy, the nucleic acid is advantageously DNA and preferably comprises an expression cassette constituted by one or more sequences of DNA encoding the polypeptide of interest under the control of one or more promoters and a transcriptional terminator which are active in the target cells. It can be also an RNA of siRNA type or antisense oligonucleotidese.

Another subject of the invention relates to a composition comprising a transfer agent corresponding to formula (I) as defined previously, and at least one polypeptide or protein. Preferentially, the transfer agent and the polypeptide or the protein can be present in a quantity such that the quantity of transfer agent (compound of formula (I)) can be comprised between 1 and 10 nanomoles of transfer agent according to the invention per μg of polypeptide, and preferably between 1 and 3 nanomoles of agent per μg of polypeptide. For the purposes of the present invention, the polypeptide can be a peptide or a protein of pharmaceutical interest. The delivery of polypeptides into the cells represents an alternative to gene therapy for developing novel therapeutic approaches directed against numerous diseases such as cancer, inflammatory and genetic disorders, infections and metabolic deficiencies such as diabetes. Among these peptides and these proteins of interest, there may be mentioned for example antibodies, antigens, lymphokines, interleukins, necrosis and apoptosis factors, interferons, growth factors, tissue plasminogen activators, factor VIII:c, erythropoietin, insulin, calcitocin, thimidine kinase, etc. Such a composition according to the invention also opens up new fields of proteomic investigations for the clarification of complex molecular mechanisms. For example, the delivery of proteins involved in the apoptosis phenomena into the cells can help to clarify programmed cell death mechanisms.

Another subject of the invention relates to a composition comprising a transfer agent corresponding to formula (I) as defined previously, and at least one biologically active molecule other than a nucleic acid or a polypeptide. This can be an active ingredient, a polysaccharide, a lipid, a peptoid, etc. For example, the peptoids can be successfully used as analogues of the peptides of therapeutic interest.

The compositions can also comprise adjuvants capable of combining with the compound corresponding to formula (I), with the biologically active molecules or with the transfer agent/biologically active molecules complex and of improving the transfecting power and pharmacology thereof. Thus, the compositions according to the invention can comprise as adjuvants one or more neutral (zwitterionic or free of ionic charges), anionic or cationic lipids. Preferentially, the lipids used are neutral lipids with two fatty chains, cholesterol or cholesterol derivatives. They can be chosen more particularly from dioleoylphosphatidylethanolamine (DOPE) (Farhood H. et al., *Biochim Biophys. Acta* (1985), 1235-1289), oleoylpalmitoylphosphatidylethanolamine (POPE), distearoyl-, dipalmitoyl-, dimyristoyl-, dilauroylphosphatidylethanolamines (DSPE, DPPE, DMPE, DLPE), as well as their once to three times N-methylated derivatives (DOPC, DPPC, DMPC), phosphatidylglycerols, glycosyldiacylglycerols, cerebrosides (such as in particular the galactocerebrosides), sphingolipids (such as in particular the sphingomyelines), asialogangliosides (such as in particular asialoGM1 and GM2), or also lipid ethers. Lipids comprising a single fatty chain can also be used, including the lysophosphatides, lysophosphatidylcholines, lysophosphatidylethanolamines, lysophosphatidylglycerols, lysophosphatidylserines or also lysophosphatidic acids. These different lipids can be natural or synthetic.

The adjuvants which can be included in the composition according to the invention can also be one or more natural or synthetic polymers, co-polymers and/or dendrimers. These polymers can be cationic such as polyamines, including polyethylenimine, polylysine, polyornithine, or also polybrene and chitosan. The polymers can also be anionic such as polyglutamic acid, polypropylacrylic acid, hyaluronic acid and polylactic-co-glycolic acid (PGLA), or neutral such as polyethylene glycol (PEG) or also certain polysaccharides such as galactomannans.

The compositions according to the invention can also comprise, as adjuvants, nanoparticles, in particular magnetic particles, particles based on organic or inorganic compounds. The adjuvants can also be polypeptides, proteins, monosaccharides, glycerol, cyclodextrins, histones, deoxycholic acid and any other "activator" ("enhancer") which improves the efficacy of delivery and the pharmacology.

The compositions can also comprise adjuvants capable of specifically targeting a determinant at the surface and/or inside the cells. These targeting elements can be covalently or non-covalently attached to the compound corresponding to formula (I) or to any other molecules contained in the composition comprising the compound of formula (I). These targeting elements can be ligands of receptors expressed at the surface of the target cells, for example a sugar, a folate, transferrin, insulin, a hormone, a peptide, an antibody, a metabolite, vitamins or any other molecule which can recognize an extracellular receptor. They can also be an intracellular vectorization element for targeting specific compartments such as the mitochondria, nucleus or cytoplasm, such as for example a nuclear or mitochondrial localization signal. Generally, the targeting element can be a sugar, a peptide, a protein, an antibody, an antibody fragment, a ligand or a ligand fragment. The adjuvant can also be a fluorophore such as rhodamine, fluorescein or biotin.

The compositions according to the invention can also comprise viruses, for example lentiviruses, retroviruses, adenoviruses, herpes viruses, baculoviruses, and/or unicellular organisms, for example bacteria, yeasts, fungi or parasites.

Preferentially, the compositions according to the invention have an adjuvant/transfer agent molar ratio comprised between 0 and 20, and more preferentially between 0.5 and 3.

The invention also extends to any composition as defined above and also comprising one or more other agents known to transfect nucleic acids, polypeptides or any other biologically active molecule.

Another subject of the present invention relates to the use of a transfer agent as defined previously for the transfer of nucleic acids, polypeptides or any other biologically active molecule into cells. This use can be in any field where the transport of a molecule of biological interest is necessary. This applies in particular to the cosmetic and/or pharmaceutical fields, or also laboratory reagents.

The invention also relates to the use of a compound of formula (I) for the preparation of a composition intended for the transfer of nucleic acids, polypeptides or any other biologically active molecule into cells.

The invention also relates to the use of a composition comprising at least one compound of formula (I) for the transfer of nucleic acids, polypeptides or any other biologically active molecule into cells.

The compositions comprising the transfer agent according to the invention can be formulated for administration by topical, cutaneous, oral, rectal, vaginal, parenteral, intranasal, intravenous, intramuscular, sub-cutaneous, intraocular, transdermal, intratracheal, intraperitoneal route, etc.

Preferably, the pharmaceutical compositions of the invention contain a pharmaceutically acceptable vehicle for an injectable formulation, in particular for a direct injection into the desired organ or for administration by topical route. They can be in particular sterile, isotonic solutions or dry, in particular lyophilized, compositions which, by adding sterilized water or physiological serum depending on the case, allow the constitution of injectable solutions. The doses of nucleic acid, polypeptide or any other biologically active molecule, used for the injection as well as the number of administrations can be adapted as a function of different parameters, and in particular as a function of the administration method used, the pathology concerned, the gene to be expressed, or also the sought duration of the treatment. As regards more particularly the administration method, this can be either a direct injection into the tissues or the circulatory routes, or a treatment of cells in culture followed by their reimplantation by injection or graft.

The invention also relates to a method of transfer of a molecule of biological interest into cells, comprising the following stages:

1. bringing the molecule of biological interest into contact with a transfer agent corresponding to formula (I) as defined above, or with a composition as defined previously in order to form an active molecule/transfer agent complex,
2. bringing the cells into contact with the complex formed in 1.

According to the invention, in stage 2, the order of addition of the cells and/or the complexes does not matter.

Preferentially, this method is used in vitro and/or in experiments carried out with previously isolated cells and/or in vivo.

In the case of a composition comprising one or more other transfection agents and/or one or more adjuvants, the method according to the invention can also comprise one or more stages of bringing the transfer agent according to the invention into contact with different transfection agents and/or with the adjuvant or adjuvants. Advantageously according to the invention, stage 1 can be preceded by a stage of bringing the compound of formula (I) into contact with other transfection agents and/or with the adjuvant or adjuvants.

The transfer agent according to the invention/biologically active molecule complexes are formed by mixing two solutions, one containing the composition based on the transfer agent according to the invention, in the presence or absence of one or more adjuvants and/or of one or more other transfection agents, and the other containing the biologically active molecule to be delivered in the presence or absence of one or more adjuvants and/or of one or more other transfection agents. The complexes are formed in a few seconds and can be charged negatively, positively, or be neutral, depending on the quantity of lipid added to the molecule to be transported.

The bringing of the cells into contact with the complex can be carried out by incubation of the cells with said complex (in vitro or ex vivo use), or by injection of the complex into an organism (in vivo use). The incubation is carried out preferably in the presence for example of 0.01 to 1000 µg of molecule of biological interest per $10^6$ cells. For in vivo administration, doses of active molecules ranging from 0.01 to 10 mg can be used.

The transfer agents according to the invention are particularly useful for their use in the transfer of biologically active molecules into primary cells or established lines. They can be eukaryotic cells such as endothelial, epithelial, fibroblastic, hepatic, hematopoietic (lymphocytes, monocytes, macrophages, dendritic cells, etc.), muscle, nerve cells (neurones, glial cells, astrocytes), etc. They can also be prokaryotic (bacteria) and plant cells, insect, yeast or parasite cells. They can be presented in differentiated or pluripotent form.

A subject of the invention is also kits for the transfer of biological material comprising at least one compound of formula (I) or at least one composition comprising at least one compound of formula (I), and optionally other solutions which are useful in carrying out a transfer of biological material.

The useful properties of the compounds according to the invention make it possible to envisage numerous other uses such as in particular use as adjuvants in a composition, particularly in a vaccine.

The following definitions are provided in order to facilitate the understanding of certain frequently-used terms in this disclosure:

By "biologically active molecule" or "active molecule" or "biologically active agent" or "molecule of biological interest" or "active ingredient", is meant any molecule or macromolecule having a specific activity in cells and used in numerous fields ranging from cell biology to medicine. These can be nucleic acids (DNA, RNA etc.), polypeptides, proteins, active ingredients, polysaccharides, peptoids, etc.

By "polypeptide" is meant any amino acid chain irrespective of its size. Thus, this term covers peptides and proteins in particular.

Apart from the above provisions, the present invention also comprises other characteristics and advantages shown by the following examples and figures, which must be considered as illustrating the invention without limiting its scope.

In particular, the applicant proposes non-limitatively various operating protocols as well as reaction intermediates which can be used for preparing the transfer agents according to the invention. It is of course within the scope of a person skilled in the art to be guided by these protocols or intermediate products for developing analogous methods for producing these same compounds.

FIGURES

FIG. 1: Reaction diagram for the synthesis of 181GSCO 1d (compound of formula I.6) in which in each stage the reagents and conditions used are:
i) Successively
a. N,N'-Dicyclohexylcarbodiimide (DCC), N-Hydroxysuccinimide (NHS), Dichloromethane/N,N'-Dimethylformamide ($CH_2Cl_2$/DMF), Ambient temperature (AT) (approximately 25° C.);
b. Cystamine dichloride, Triethylamine (TEA), DMF, AT;
ii) Successively
a. Dioleoylglycerosuccinate (DOGS), DCC, NHS, $CH_2Cl_2$/DMF, AT;
b. TEA, $CH_2Cl_2$, AT;
iii) Trifluoroacetic acid ($CF_3COOH$), $CH_2Cl_2$, AT.

FIG. 2: Reaction diagram for the synthesis of 181GSGlu $(CO)_2$ 4e (compound of formula I.15) in which in each stage the reagents and conditions used are:
i) Successively
a. N,N'-Diisopropylcarbodiimide (DIC), Hydroxybenzotriazole (HOBt), $CH_2Cl_2$/DMF, AT;
b. Di-tert butyl L-Glutamate (H-Glu(OtBu)-OtBu), $CH_2Cl_2$, AT;
ii) $CF_3COOH$, $CH_2Cl2$), AT.
iii) Successively
a. DIC, HOBt, $CH_2Cl_2$/DMF, AT;
b. Boc-Orn(Boc)-NH—$(CH_2)_2$—S—S—$(CH_2)_2$—$NH_2$ 1b, TEA, $CH_2Cl_2$, AT;
iv) $CF_3COOH$, $CH_2Cl2$), AT.

FIG. 3: Reaction diagram for the synthesis on a solid support of bis-lysine 5e, used then as a synthesis intermediate for the preparation of 181GSCL$_2$ 5f (compound of formula I.18) in which, in each stage, the reagents and conditions used are:
i) Diisopropylethylamine (DIPEA), $CH_2Cl_2$, AT;
ii) Tris-(2-aminoethyl)amine, $CH_2Cl_2$, AT;
iv) Nα,Nε-di-tert-butyloxycarbonyl-L-Lysine (Boc-Lys (Boc)-OH), DIC, HOBt, $CH_2Cl_2$, AT;
v) $CF_3CH_2OH$, $CH_2Cl_2$, AT.

FIG. 4A: histogram representing the in vitro transfer activity of the lipid formulation 181 GSCO (compound of formula I.6)/DOPE for transporting DNA (pCMV-EGFP) into several cell lines (Vero, NiH3-T3, A549, PC-12).

Figure 4:
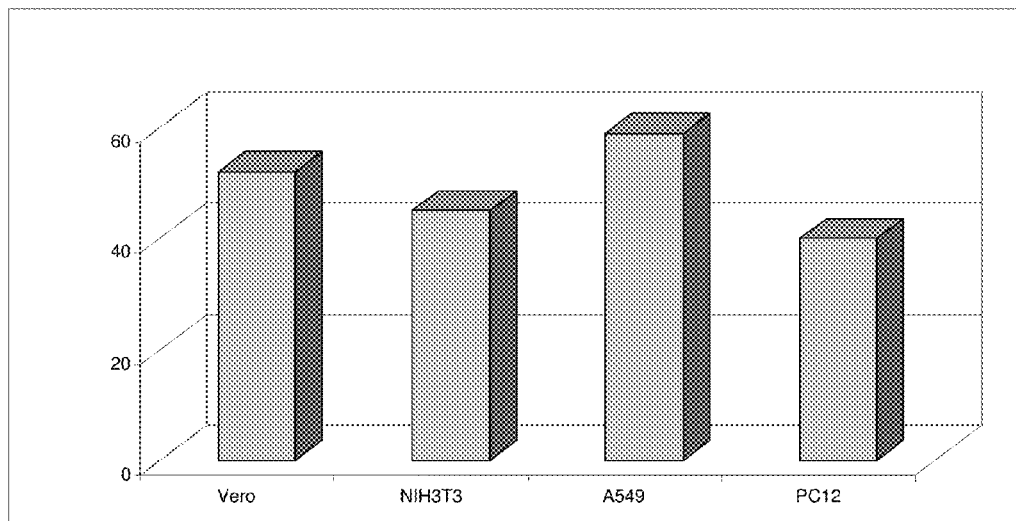
Figure 4B:
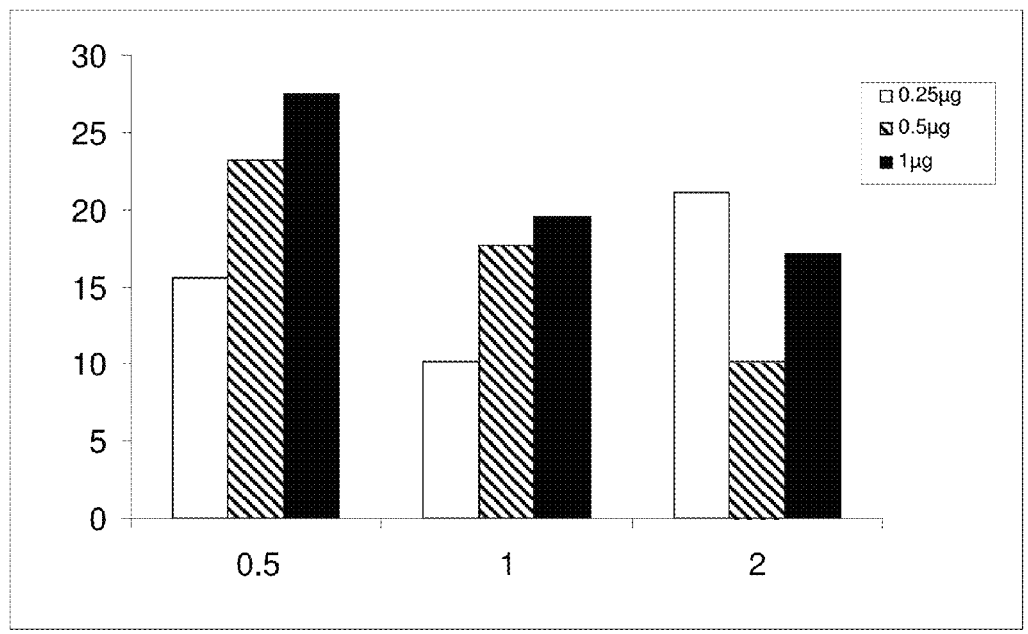

FIG. 4B: histogram representing the in vitro transfer activity of the lipid formulation 181GSCO (compound of formula I.6)/DOPE for transporting DNA (pCMV-LacZ) into Vero cells (quantity of β-galactosidase), as a function of the quantity of DNA (μg) and of the quantity of formulated lipid (0.5, 1, 2 μl).

Figure 5:
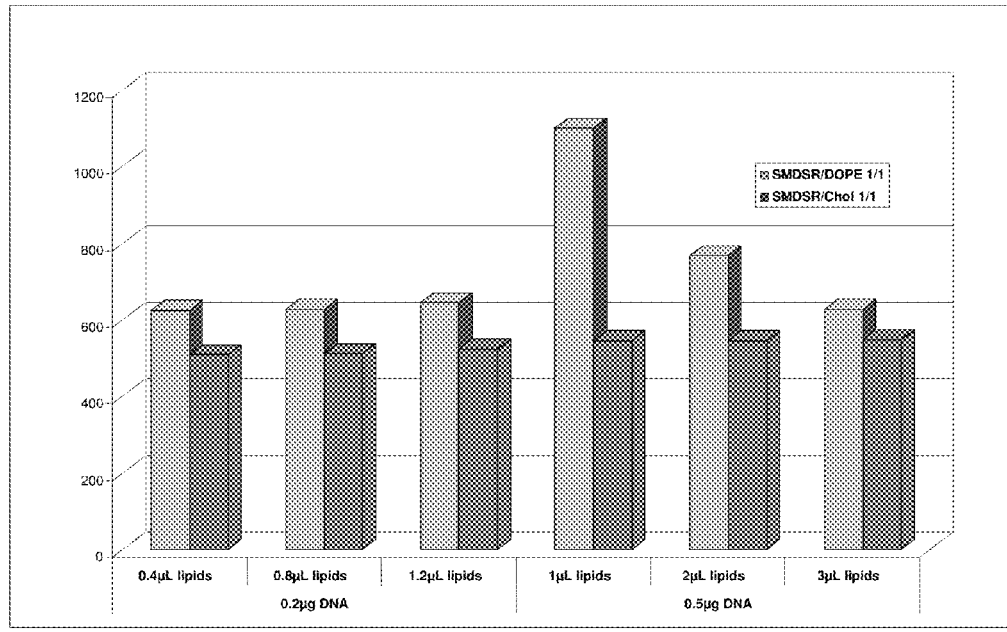

FIG. 5: Histogram representing the in vitro transfer activity (fluorescence intensity) of 181GSCR (compound of formula I.7), formulated with DOPE or cholesterol, for transporting DNA (pCMV-EGFP) into NiH3-T3 cells, as a function of the quantity of DNA and of the quantity of lipid formulated.

Figure 6:
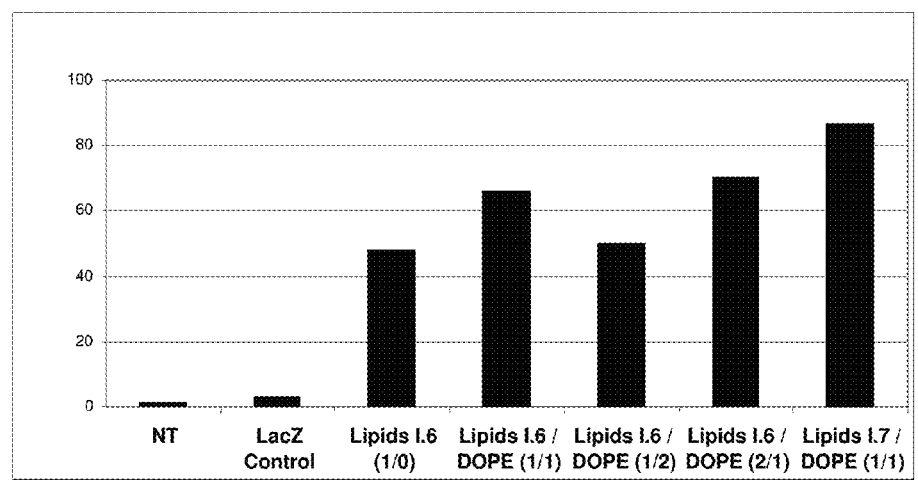

FIG. 6: Histogram representing the in vitro transfer activity of the lipid formulation 181GSCO (compound of formula I.6) formulated or not formulated with different ratios of DOPE into Hela-GFP cells for transporting siRNA (anti-GFP) (% of inhibition of the expression of GFP).

Figure 7:
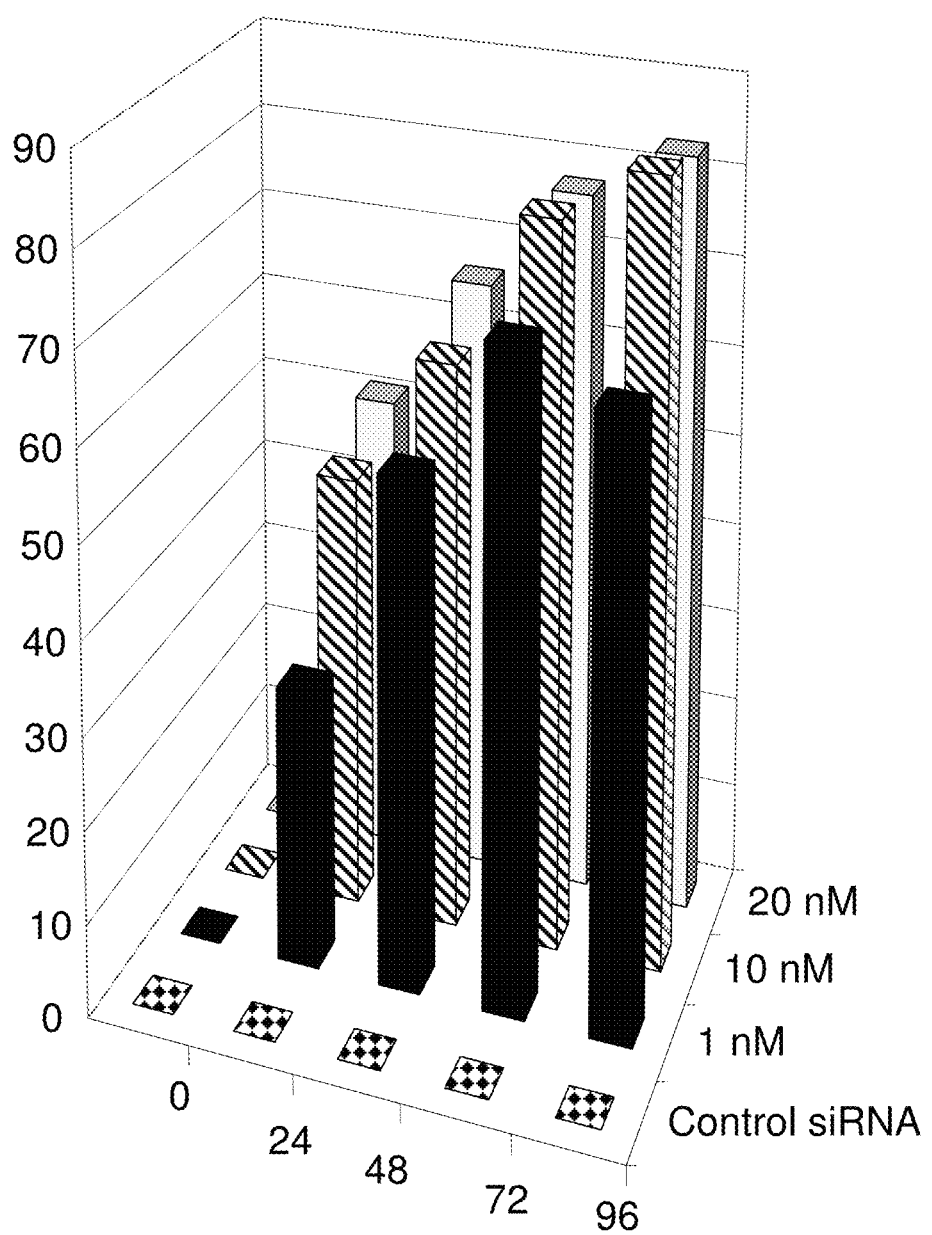

FIG. 7. Histogram representing the in vitro transfer activity of the lipid formulation 181 GSCR (compound of formula I.7)/DOPE into Hela-GFP cells for transporting siRNA (anti-GFP) (% of inhibition of the expression of GFP), as a function of the siRNA concentration (in nM) and of the incubation time expressed in hours.

FIG. 8A, 8B, 8C: Photos representing the in vitro transfer activity of the formulations:
181GSCO (compound of formula I.6)/DOPE, for the transport
  of fluorescein-labelled goat IgG into NiH3-T3 cells (FIG. 8A)
  of R-Phycoerythrin into Vero cells (FIG. 8B)
  of β-Galactosidase into Hela cells, (FIG. 8C)
181CSCR (compound of formula I.7)/DOPE, for the transport
  of fluorescein-labelled goat IgG into NiH3-T3 cells (FIG. 8D) and
181GluO2 (compound of formula I.11)/DOPE for the transport
  of R-Phycoerythrin into Hela cells (FIG. 8E)

FIGS. 9A and 9B Curves representing the in vitro transfer activity of the formulation 181GSCO (compound of formula I.6)/DOPE into NiH3-T3 cells for transporting a fluorescein-labelled goat IgG antibody. The transfer activity is determined as a % of fluorescent cells (FIG. 9A) and quantity of proteins internalized in the cells (FIG. 9B) as a function of the incubation time.

FIGS. 10A and 10B Histograms representing the in vitro transfer activity of the lipid formulation 181GluO2 (compound of formula I.11)/DOPE into Jurkat cells in suspension for transporting DNA (pCMV-EGFP), as a function of the quantity of lipid formulated (μl). The transfer activity is determined as a quantity of GFP expressed in the cells (FIG. 10A), and as a % of fluorescent cells (FIG. 10B).

Figure 11:
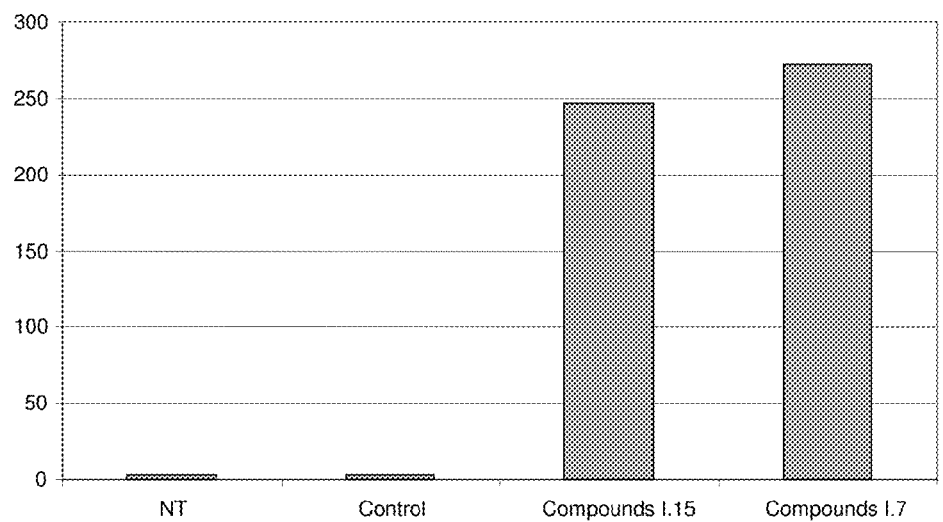

FIG. 11: Histogram representing the in vitro transfer activity (fluorescence intensity) of the lipids 181GSCR (compound of formula I.7) and 181GSGlu(CO)$_2$ (compound of formula I.15) formulated with DOPE into Jurkat cells in suspension for the intracellular delivery of a fluorescent siRNA.

Figure 12:
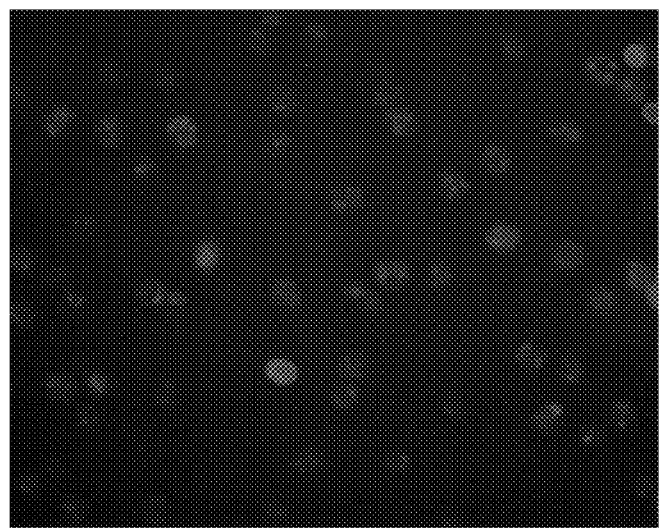

FIG. 12: Photo representing the in vitro transfer activity of the formulation 181GSCO (compound of formula I.6)/DOPE into Jurkat cells in suspension for transporting a TRITC-labelled protein (BSA).

Figure 13:
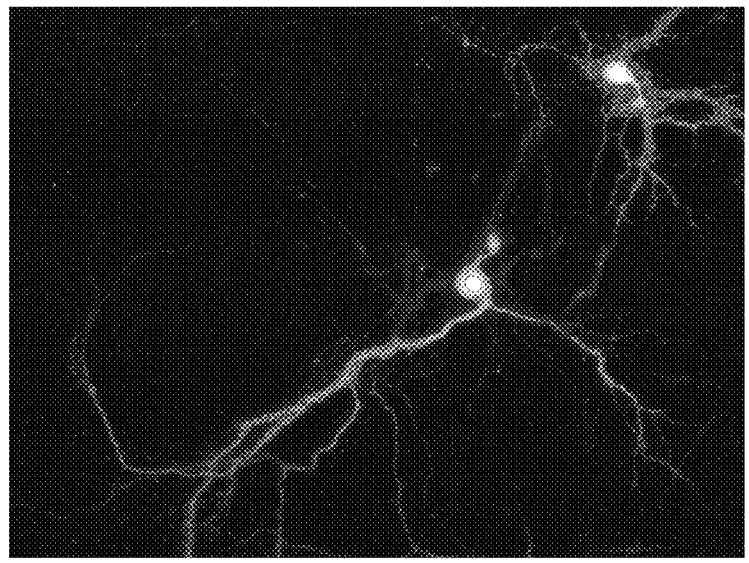

FIG. 13: Photo representing the in vitro transfer activity of the formulation 181GluO2 (compound of formula I.11)/DOPE into the primary neurones for transporting DNA (pCMV-EGFP).

Figure 14:
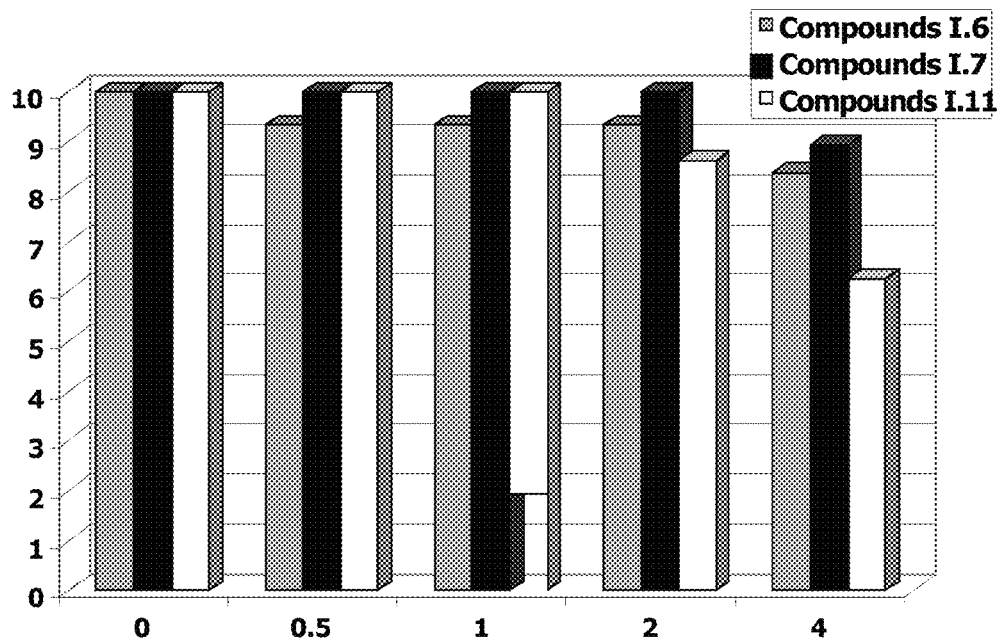

FIG. 14: Histogram representing the total quantity of proteins (μg) expressed by Hela cells as a function of the quantity of lipids I.6, I.7 and I.11 formulated with DOPE (μM). The cells were incubated for 48 hours with or without lipids in a 96-well plate and the quantity of proteins per well was determined by a Bradford test.

EXAMPLES

A. Syntheses of Transfer Agents According to the Invention a) Material

The majority of the reagents and solvents are obtained from Merck (Darmstadt, Germany), VWR Prolabo (Briare, France), Sigma-Aldrich SARL (Saint Quentin Fallavier, France) and Fluka (Division of Sigma-Aldrich, Saint Quentin Fallavier, France). The glycerolipid derivatives (DOGS, DPGS, DMGS, DLGS) are obtained from Avanti Polar Lipids (Alabaster, Ala., USA). The protected amino acids (Boc-Orn (Boc)-OH, Boc-Lys(Boc)-OH, Boc-Arg(Boc)$_2$-OH, H-Glu (OtBu)-OtBu.HCl) are obtained from Bachem Biochimie SARL (Voisin-le-Bretonneux, France). All the anhydrous solvents are obtained from Sigma-Aldrich and Fluka and used as they are.

b) Methods

Chromatography Techniques

Thin layer chromatographies (TLC) are carried out on 5×7.5 cm aluminium covered with silica gel 60 $F_{254}$ (Merck). The compounds are developed under UV light (λ=254 nm), with iodine, by immersion in a ninhydrin developer (0.2% in butanol) followed by a stage of heating at 150° C. in the case of the compounds possessing a primary amine function, or by immersion in a cerium/concentrated molybdate ($H_2O$/$H_2SO4$/$(NH_4)_6Mo_7O_{24}$.$4H_2O$/$Ce(SO_4)_2$.$3H_2O$ developer: 90/10/15/1) followed by a stage of heating at 110° C. in the case of the sulphur-containing compounds.

The synthesis products are purified on chromatography columns on silica. The flash chromatography separations are carried out on silica gel 60 (230-400 mesh ASTM) (Merck).

Mass Spectrometry:

Preparation of the Samples:

The products to be analyzed are dissolved (0.01 mg·mL$^{-1}$) in a methanol/water mixture 50/50 (v/v) or acetonitrile/water mixture 50/50 (v/v) and the solutions are introduced directly (5 μL·min$^{-1}$) into the electrospray source by means of a syringe pump (Harvard Apparatus, Les Ulis, France).

Apparatus:

The mass spectra are produced on a Waters-Micromass Q-TOF device (Manchester, U.K.) equipped with a pneumatically assisted electrospray ion source (Z-Spray). Nitrogen is used as desolvation and nebulization gas with a flow rate of 250 and 50 L/h, respectively. The temperatures of the source and of the desolvation gas are fixed at 80 and 150° C. respectively. The capillary pressure is ±180 V (±QD). For collision induced dissociation (CID) experiments, argon is used as a collision gas, at an analyzer pressure set at 5×10$^{-5}$ Torr and a collision energy adjusted to 90 V.

The exact mass measurements are carried out on a Waters-Micromass LCT device (Manchester, U.K.), equipped with a pneumatically assisted electrospray source (Z-spray), and provided with an additional nebulizer (Lockspray) for the reference compound (NaI). Nitrogen is used as desolvation and nebulization gas at a flow rate of 500 and 20 L/h, respectively. The temperatures of the source and the desolvation gas are fixed at 80 and 120° C. respectively. The capillary pressure is ±3.0 kV and the cone pressure ±100 V (±QD).

The spectra are accumulated at a speed of 3 seconds per scan for a mass range comprised between 100 and 3500 uma.

The resolution used is 9000 FWHM for the Q-TOF and 3000 FWHM for the LCT. The data acquisition and processing are carried out with the program MassLynx V3.5.

LC/MS Coupling

Certain compounds are analyzed by High Performance Liquid Chromatography coupled with Mass Spectrometry (LC/MS). The HPLC is carried out with a Waters Alliance 2695 device, provided with an Alltech Prevail™ C18 analytical column (Lexington, Ky., USA). The detection is carried out at the outlet of the HPLC column by a Waters-Micromass Q-TOF mass spectrometer.

c) Syntheses

Example 1

Preparation of DiOleoyl-Glycero-Succinyl-Cystamido-Ornithine (Compound 1d: (181GSCO)

181GSCO, or compound 1d, of formula:

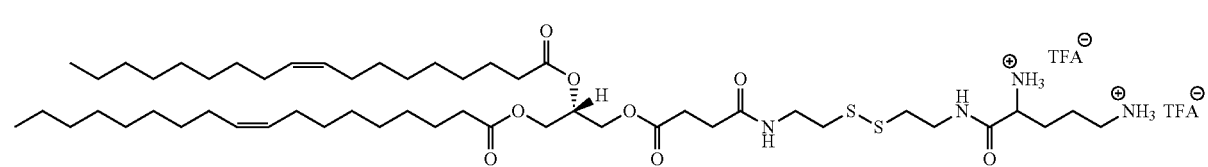

1d is obtained in three stages from $N_\alpha,N_\epsilon$-di-Boc-ornithine 1a (FIG. 1)

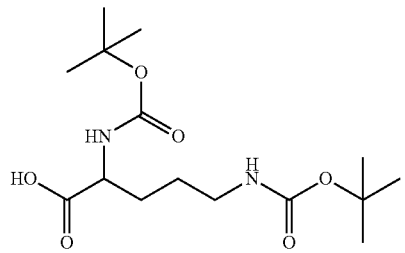

1a 2.1 Stage 1: Preparation of Cystamido-di-Boc-Ornithine (1b)

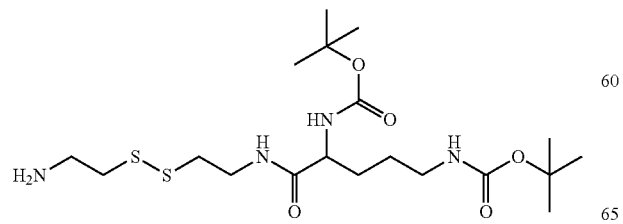

1b

N$_\alpha$,N$_\epsilon$-di-Boc-ornithine 1a (1.22 mmol; 406 mg) is placed beforehand in a dry 100 mL flask under an inert atmosphere then dissolved in 20 mL of anhydrous CH$_2$Cl$_2$ under stirring. N,N'-dicyclohexylcarbodiimide (DCC) (1.83 mmol; 378 mg) which is freshly recrystallized and in solution in 5 mL of anhydrous CH$_2$Cl$_2$, then N-Hydroxysuccinimide (NHS) (1.83 mmol; 211 mg) in solution in 5 mL of anhydrous DMF, are successively added to the reaction medium. The reaction is then maintained for 2 hours under stirring and under an inert atmosphere at ambient temperature. Cystamine dichloride (6.1 mmol; 1.37 g) is dissolved in 1 mL of water in a 25 mL flask. Triethylamine (12.2 mmol; 1.7 mL) then 10 mL of DMF are added to this solution under stirring. This solution is stirred for 10 minutes at 50° C. then immediately added to the reaction medium. After stirring for 24 hours at ambient temperature, a significant precipitate has formed in the reaction medium. The mixture is then filtered, the cake is washed with CH$_2$Cl$_2$ (2×20 mL), and the filtrates thus obtained are combined and evaporated under a rough vacuum. The coupling product is then purified by flash chromatography on silica gel (elution: CH$_2$Cl$_2$/MeOH 95/5 then 8/2 (v/v)). In this way 260 mg of compound 1b is isolated, i.e. a yield of 46%.

TLC: R$_f$ 1b=0.6 (CH$_2$Cl$_2$/MeOH 8/2 (v/v))

ESI-MS+: m/z measured at 467.1 [M+H]$^+$, calculated at 467.2 for C$_{19}$H$_{39}$N$_4$O$_5$S$_2$.

2.2 Stage 2: Preparation of DiOleoyl-Glycero-Succinyl-Cystamido-di-Boc-Ornithine (1c)

1,2-Dioleoyl-sn-Glycero-3-Succinate (DOGS) (0.485 mmol; 350 mg) is placed beforehand in a dry 100 mL flask under an inert atmosphere then dissolved in 20 mL of anhydrous CH$_2$Cl$_2$ under stirring. Freshly crystallized DCC (0.727 mmol; 150 mg) in solution in 5 mL of anhydrous CH$_2$Cl$_2$, then NHS (0.727 mmol; 84 mg) in solution in 5 mL of anhydrous DMF, are successively added to the reaction medium. The reaction is then maintained for 2 hours under stirring and under an inert atmosphere at ambient temperature. Compound 1b (0.535 mmol; 250 mg) is placed beforehand in a dry 10 mL flask under an inert atmosphere, then dissolved in 10 mL of anhydrous CH$_2$Cl$_2$. Triethylamine (0.535 mmol; 75 μL) is added to this solution under stirring. The solution is stirred for 10 min at ambient temperature then added to the reaction medium. After stirring at ambient temperature under an inert atmosphere for 24 hours, the reaction is stopped and the reaction medium is evaporated to dryness under a rough vacuum. The coupling product is then purified by flash chromatography on silica gel (elution gradient from 0 to 5% MeOH in CH$_2$Cl$_2$). In this way 414 mg of compound 1c is isolated, i.e. a yield of 73%.

TLC: R$_f$ 1c=0.8 (CH$_2$Cl$_2$/MeOH 9/1 (v/v))

ESI-MS+: m/z measured at 1169.6 [M+H]$^+$, calculated at 1169.8 for C$_{62}$H$_{113}$N$_4$O$_{12}$S$_2$, m/z measured at 569.4 [M+H+Na]$^{2+}$, calculated at 569.4 for C$_{62}$H$_{113}$N$_4$O$_{12}$S$_2$Na.

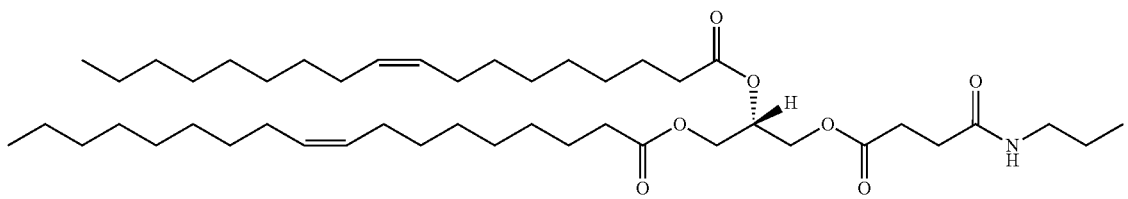

1c

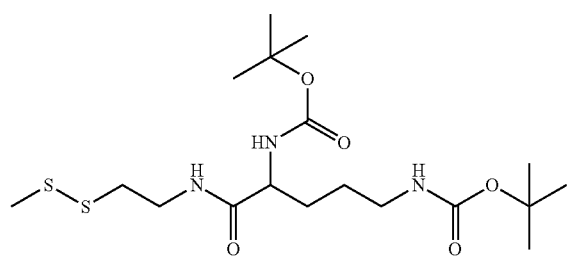

2.3 Stage 3: Preparation of 181 GSCO (1d)

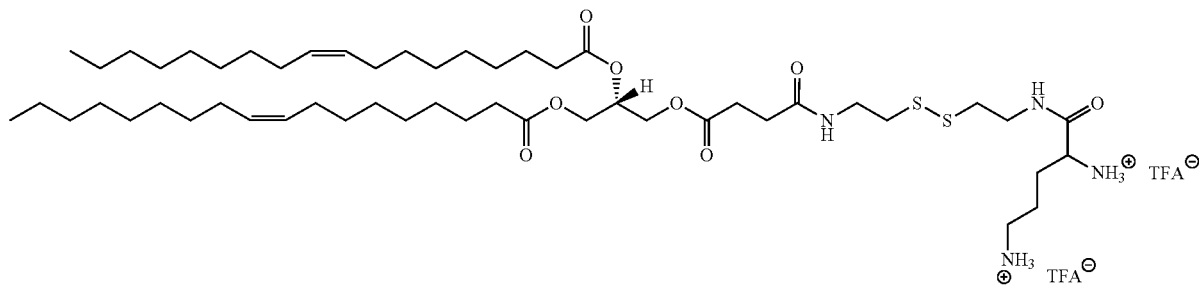

1d

Compound 1c (0.342 mmol; 400 mg) is dissolved in 8 mL of $CH_2Cl_2$ in a 50 mL flask, then 2 mL of trifluoroacetic acid are added to the reaction medium. The reaction is then maintained under stirring at ambient temperature for 1 hour. The reaction medium is evaporated to dryness under a rough vacuum. In order to drive off the traces of excess trifluoroacetic acid, the final residue is taken up 3 times in succession in 5 mL of dichloromethane then evaporated to dryness. In this way 410 mg of compound 1d is isolated in the form of a trifluoroacetate salt. The reaction is quantitative.

The total synthesis yield (3 stages) is 34%.
TLC: $R_f$ 1d=0.1 ($CH_2Cl_2$/MeOH 9/1 (v/v))
HPLC: Rt=39.73 min
(ternary gradient $H_2O$/$CH_3CN$/$CH_3CN$+10% $CH_3COOH$, Flow rate=1 mL/min).
ESI-HRMS (high resolution with detection in positive mode): m/z measured at 969.6739 [M+H]$^+$, calculated at 969.6748 for $C_{52}H_{97}N_4O_8S_2$ (deviation: 0.9 ppm).

Example 2

Preparation of
DiOleoyl-Glycero-Succinyl-Cystamido-Arginine 2d
(181GSCR)

181 GSCR, or compound 2d, of formula:

is obtained in three stages from $N_\alpha,N_\omega,N_{\omega'}$-tris-Boc-L-Arginine 2a.

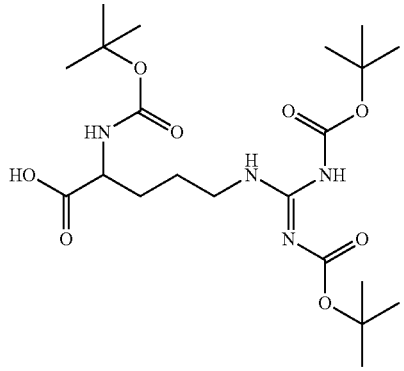

2a

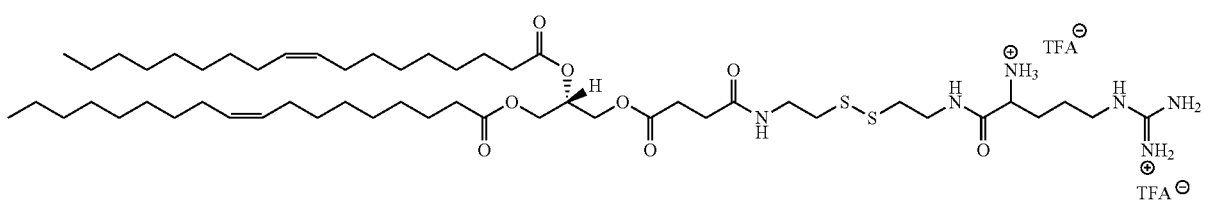

2d

2.1 Stage 1: Preparation of Cystamido-tris-Boc-L-Arginine (2b)

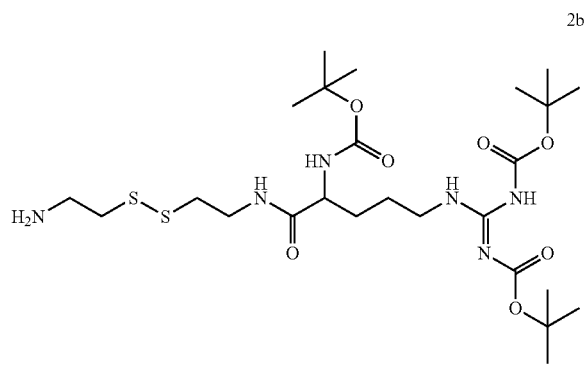 [SMILES: CC(C)(C)OC(=O)/N=C(/NCCCC(NC(=O)OC(C)(C)C)C(=O)NCCSSCCN)NC(=O)OC(C)(C)C]

2b $N_\alpha,N_\omega,N_{\omega'}$-tris-Boc-L-Arginine 2a (1.21 mmol; 875 mg) is placed beforehand in a dry 250 mL flask under an inert atmosphere then dissolved in 30 mL of anhydrous DMF under stirring. N,N'-diisopropylcarbodiimide (DIC) (1.82 mmol; 282 µL), then N-Hydroxysuccinimide (NHS) (1.82 mmol; 209 mg) in solution in 5 mL of anhydrous DMF, are successively added to the reaction medium. The reaction is then maintained under stirring and under an inert atmosphere at ambient temperature for 2 hours. Cystamine dichloride (6.1 mmol; 1.37 g) is dissolved in 2 mL of water in a 50 mL flask. Triethylamine (12.2 mmol; 1.7 mL) is added to this solution under stirring, then 20 mL of DMF. This solution is stirred for 5 minutes at 50° C. then immediately added to the reaction medium. The reaction is then maintained under stirring at ambient temperature for 24 hours. The solvents are then evaporated off under a rough vacuum until an oily residue of 1 to 2 mL is obtained. This residue is taken up in 50 mL of $CH_2Cl_2$ under stirring. The precipitate which has formed is then filtered and washed with $CH_2Cl_2$ (2×10 mL). The filtrates are collected and evaporated under a rough vacuum. The coupling product is then purified by flash chromatography on silica gel (elution: $CH_2Cl_2$/MeOH 95/5 then 9/1 (v/v)). In this way 345 mg of compound 2b is isolated, i.e. a yield of 47%.

TLC: $R_f$ 2b=0.6 ($CH_2Cl_2$/MeOH 8/2 (v/v))

ESI-MS+: m/z measured at 609.2 $[M+H]^+$, calculated at 609.3 for $C_{25}H_{49}N_6O_7S_2$.

2.2 Stage 2: Preparation of DiOleoyl-Glycero-Succinyl-Cystamido-tris-Boc-L-Arginine (2c)

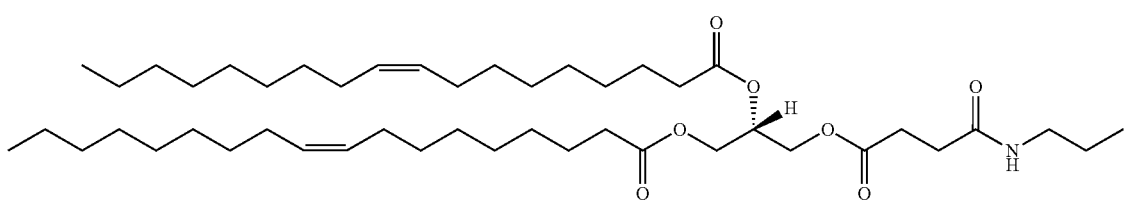

2c

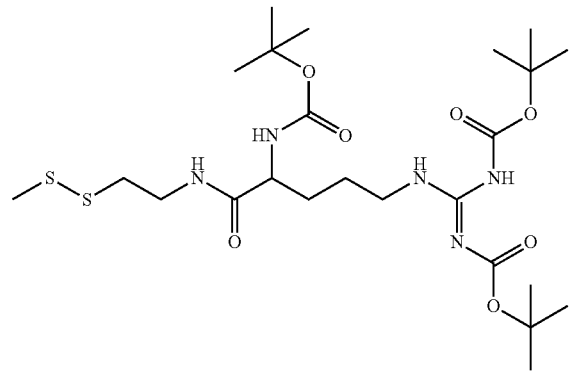

1,2-Dioleoyl-sn-Glycero-3-Succinate (DOGS) (0.33 mmol; 240 mg) is placed beforehand in a dry 250 mL flask under an inert atmosphere then dissolved in 20 mL of anhydrous $CH_2Cl_2$ under stirring. Freshly recrystallized DCC (0.50 mmol; 103 mg) in solution in 5 mL of anhydrous $CH_2Cl_2$, then NHS (0.50 mmol; 58 mg) in solution in 5 mL of anhydrous DMF, are successively added to the reaction medium. The reaction is then maintained under stirring and under an inert atmosphere at ambient temperature for 2 hours. Compound 2b (0.50 mmol; 305 mg) is placed beforehand in a dry 50 mL flask under an inert atmosphere, then dissolved in 15 mL of anhydrous $CH_2Cl_2$. Triethylamine (0.50 mmol; 70 µL) is added to this solution under stirring. The solution is stirred for 10 minutes at ambient temperature then added to the reaction medium. After stirring at ambient temperature under an inert atmosphere for 24 hours, the reaction is stopped and the reaction medium is evaporated to dryness under a rough vacuum. The coupling product is then purified by flash chromatography on silica gel (elution gradient from 0 to 2% MeOH in $CH_2Cl_2$). In this way 239 mg of compound 2c is isolated, i.e. a yield of 55%.

TLC: $R_f$ 2c=0.9 ($CH_2Cl_2$/MeOH 9/1 (v/v))

ESI-MS+: m/z measured at 1311.7 $[M+H]^+$, calculated at 1311.9 for $C_{68}H_{123}N_6O_{14}S_2$; m/z measured at 667.4 $[M+H+Na]^{2+}$, calculated at 667.4 for $C_{68}H_{123}N_6O_{14}S_2Na$.

2.3 Stage 3: Preparation of 181 GSCR (2d)

Compound 2c (0.17 mmol; 220 mg) is dissolved in 5 mL of $CH_2Cl_2$ in a 50 mL flask, then 5 mL of trifluoroacetic acid is added to the reaction medium. The reaction is then maintained for 1 hour under stirring at ambient temperature. The reaction medium is evaporated to dryness under a rough vacuum. In order to drive off the traces of excess trifluoroacetic acid, the final residue is taken up 3 times in succession in 5 mL of dichloromethane then evaporated to dryness. In this way 210 mg of compound 2d is isolated in the form of a trifluoroacetate salt. The reaction is quantitative.

The total synthesis yield (3 stages) is 26%.

TLC: $R_f$ 2d=0.1 ($CH_2Cl_2$/MeOH 9/1 (v/v))

HPLC: Rt=39.46 min (ternary gradient $H_2O$/$CH_3CN$/$CH_3CN$+10% $CH_3COOH$, Flow rate=1 mL/min).

ESI-HRMS (high resolution with detection in positive mode): m/z measured at 1011.6984 $[M+H]^+$, calculated at 1011.6966 for $C_{53}H_{99}N_6O_8S_2$ (deviation: 1.8 ppm).

Example 3

Preparation of DiLauroyl-Glycero-Succinyl-Cystamido-Lysine (3) (12GSCL)

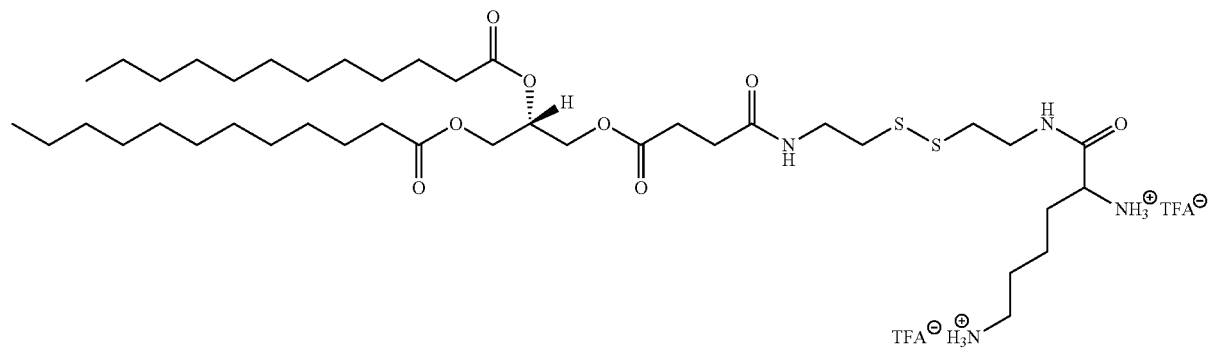

3

The synthesis procedure is identical to the synthesis of 181GSCO (Example 1) but using $N_\alpha,N_\delta$-di-Boc-L-Lysine instead of $N_\alpha,N_\epsilon$-di-Boc-L-Ornithine and 1,2-Dilauroyl-sn-Glycero-3-Succinate (DLGS) instead of 1,2-Dioleoyl-sn-Glycero-3-Succinate (DOGS). A total yield of 31% is obtained.

TLC: $R_f$ 3=0 ($CH_2Cl_2$/MeOH 9/1 (v/v))

ESI-HRMS (high resolution with detection in positive mode): m/z measured at 819.5356 $[M+H]^+$, calculated at 819.5339 for $C_{40}H_{77}N_4O_8S_2$ (deviation: 2.1 ppm).

Example 4

Preparation of DiOleoyl-Glycero-Succinyl-Glutamido-bis-(Cystamido-Ornithine): 181 GSGlu(CO)$_2$; (Compound 4e: FIG. 2

181GSGlu(CO)$_2$, or compound 4e, of formula:

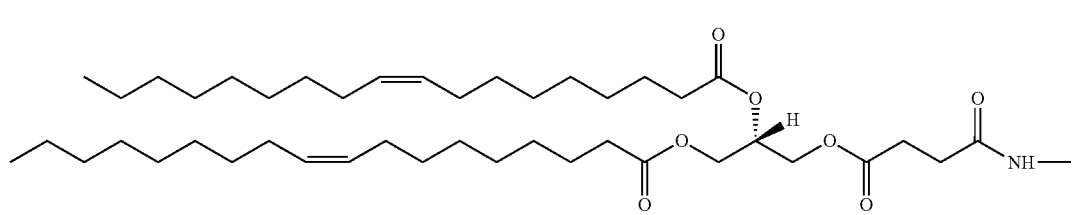

4e 1,2-Dioleoyl-sn-Glycero-3-Succinate (DOGS) 4a (0.031 mmol; 22.5 mg) is placed beforehand in a dry 10 mL flask under an inert atmosphere then dissolved in 3 mL of anhydrous CH$_2$Cl$_2$ under stirring. DIC (0.047 mmol; 7.3 μL), then HOBt (0.047 mmol; 6.4 mg) in solution in 500 μL of anhydrous DMF are successively added to the reaction medium. The reaction is then maintained under stirring and under an

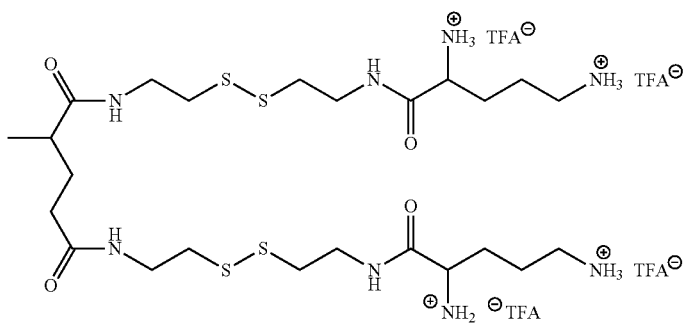

is obtained in four stages from 1,2-Dioleoyl-sn-Glycero-3-Succinate(DOGS) 4a (FIG. 2).

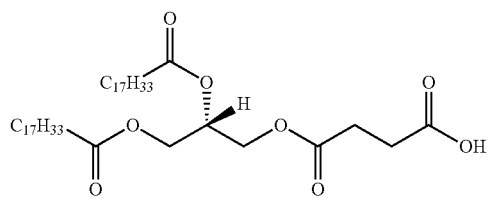

4a

4.1 Preparation of DiOleoyl-Glycero-Succinyl-di-OtBu-Glutamate (4b)

inert atmosphere at ambient temperature for 2 hours. H-Glu(OtBu)-OtBu.HCl (0.047 mmol; 14 mg) is placed beforehand in a second dry 5 mL flask under an inert atmosphere, then dissolved in 500 μL of anhydrous CH$_2$Cl$_2$. Triethylamine (0.047 mmol; 6.6 μL) is added to this solution under stirring. The solution is stirred at ambient temperature for 10 minutes then added to the reaction medium. After stirring at ambient temperature under an inert atmosphere for 24 hours, the reaction is stopped and the reaction medium is evaporated to dryness under a rough vacuum. The coupling product is then purified by flash chromatography on silica gel (elution gradient from 0 to 1% MeOH in CHCl$_3$). In this way 28.1 mg of compound 4b is isolated, i.e. a yield of 93%.

TLC: R$_f$ 4b=0.9 (CHCl$_3$/MeOH/AcOH 95/5/0.2 (v/v/v))

ESI-MS+: m/z measured at 984.8 [M+Na]$^+$, calculated at 984.7 for C$_{56}$H$_{99}$NO$_{11}$Na.

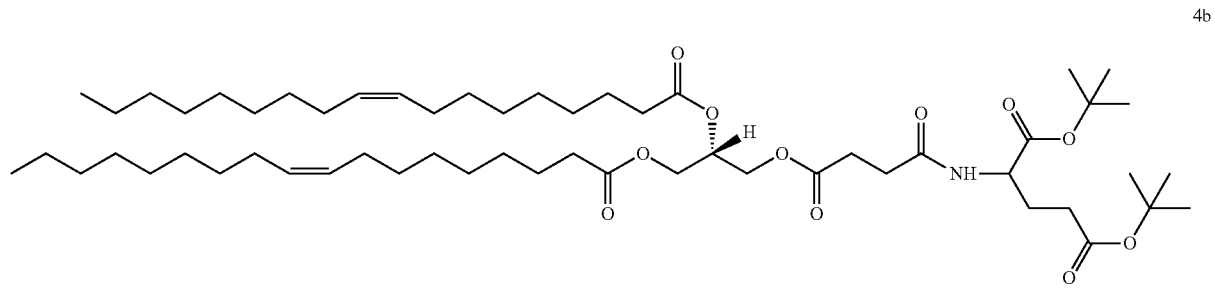 [SMILES: CCCCCCCC/C=C\CCCCCCCC(=O)OC[C@@H](COC(=O)CCC(=O)NC(CCC(=O)OC(C)(C)C)C(=O)OC(C)(C)C)OC(=O)CCCCCCC/C=C\CCCCCCCC]

4b

4.2 Preparation of DiOleoyl-Glycero-Succinyl-Glutamate (4c)

Compound 4c (0.015 mmol; 12.5 mg) is placed beforehand in a dry 10 mL flask under an inert atmosphere then dissolved in 3 mL of anhydrous $CH_2Cl_2$ under stirring. DIC (0.045

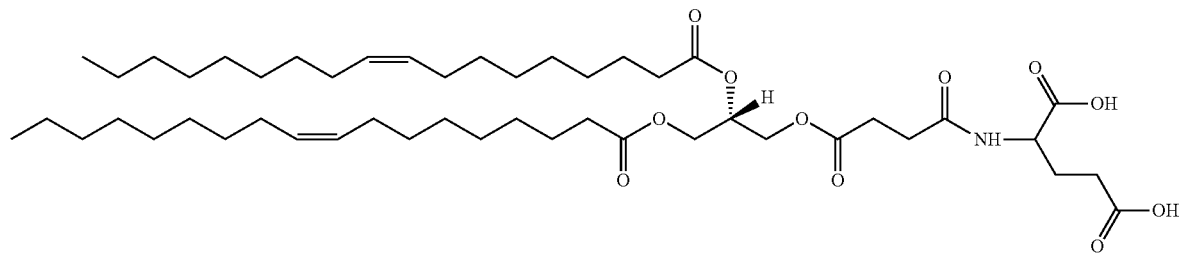

4c

Compound 4b (0.026 mmol; 25.5 mg) is dissolved in 1.6 mL of $CH_2Cl_2$ in a 10 mL flask, then 400 μL of trifluoroacetic acid are added to the reaction medium. The reaction is then maintained under stirring at ambient temperature for 1 hour. The reaction medium is evaporated to dryness under a rough vacuum. In order to drive off the traces of excess trifluoroacetic acid, the final residue is taken up 3 times in succession in 5 mL of dichloromethane then evaporated to dryness. In this way 24.4 mg of compound 4c is isolated. The reaction is quantitative.

TLC: $R_f$ 4c=0.1 ($CHCl_3$/MeOH/AcOH 95/5/0.2 (v/v/v); $R_f$ 4b=0.9)

ESI-MS+: m/z measured at 871.6 [M+Na]$^+$, calculated at 871.6 for $C_{48}H_{82}NO_{11}Na$.

4.3 Preparation of DiOleoyl-Glycero-Succinyl-Glutamido-di(Cystamido-di-Boc-Ornithine) (4d)

mmol; 7.0 μL) then HOBt (0.045 mmol; 6.1 mg) in solution in 0.5 mL of anhydrous DMF are successively added to the reaction medium. The reaction is then maintained under stirring and under an inert atmosphere at ambient temperature for 2 hours. Compound 1b (synthesis described previously in Example 1) (0.045 mmol; 21.0 mg) is placed beforehand in a second dry 10 mL flask under an inert atmosphere, then dissolved in 1.5 mL of anhydrous $CH_2Cl_2$. Triethylamine (0.045 mmol; 6.2 μL) is added to this solution under stirring. The solution is stirred at ambient temperature for 10 minutes then added to the reaction medium. After stirring at ambient temperature under an inert atmosphere for 24 hours, the reaction is stopped and the reaction medium is evaporated to dryness under a rough vacuum. The coupling product is then purified by flash chromatography on silica gel (elution gradient from 0 to 5% MeOH in $CH_2Cl_2$). In this way 20.6 mg of compound 4d is isolated, i.e. a yield of 80%.

TLC: $R_f$ 4d=0.35 ($CH_2Cl_2$/MeOH 95/5 (v/v))

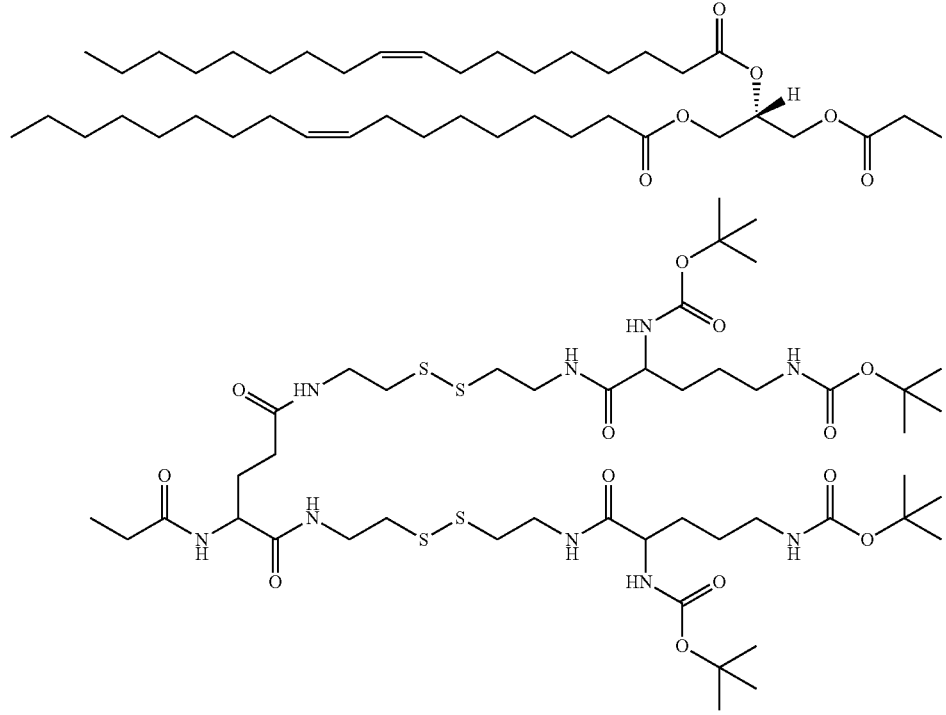

4d

ESI-MS+: m/z measured at 1769.2 [M+Na]+, calculated at 1769.0 for $C_{86}H_{155}N_9O_{19}S_4Na$.

4.4 Preparation of 181GSGlu(CO)$_2$ (4e)

Compound 4d (0.011 mmol; 20 mg) is dissolved in 1.6 mL of $CH_2Cl_2$ in a 10 mL flask, then 400 µL of trifluoroacetic acid are added to the reaction medium. The reaction is then maintained under stirring at ambient temperature for 1 hour. The reaction medium is evaporated to dryness under a rough vacuum. In order to drive off the traces of excess trifluoroacetic acid, the final residue is taken up 3 times in succession in 5 mL of dichloromethane then evaporated to dryness. In this way 19.5 mg of compound 4e is isolated in the form of a trifluoroacetate salt. The reaction is quantitative.

TLC: $R_f$4e=0 ($CH_2Cl_2$/MeOH 9/1 (v/v); $R_f$4d=0.9)

ESI-MS+: m/z measured at 1346.9 [M+H]+, calculated at 1346.8 for $C_{66}H_{124}N_9O_{11}S_4$; m/z measured at 1368.9 [M+Na]+, calculated at 1368.8 for $C_{66}H^{123}N_9O_{11}S_4Na$.

Example 5

Preparation of DiOleoyl-Glycero-Succinyl-Cystamido-bis-Lysine (5f) (181GSCL$_2$)

181 GSCL$_2$, or compound 5f, of formula:

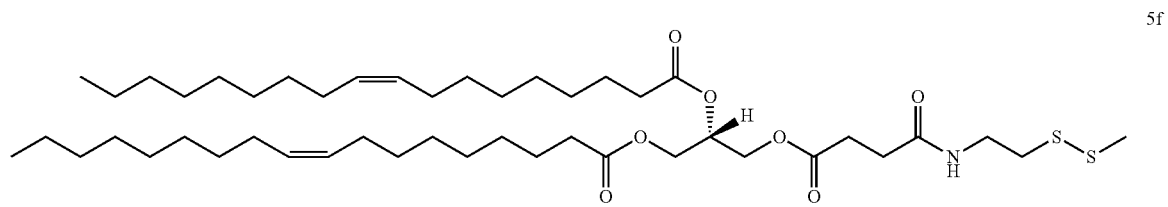

is obtained from the compound bis-lysine 5e the preparation of which is described below.

5.1 Preparation of a Branched Bis-Lysine as a Synthesis Precursor of the Transfer Agents: Synthesis of [Boc-Lys(Boc)-NH—(CH$_2$)$_2$]$_2$—N—(CH$_2$)$_2$—NH—CH$_2$—COOH (5e) by SPPS (FIG. 3)

Compound 5e, of formula:

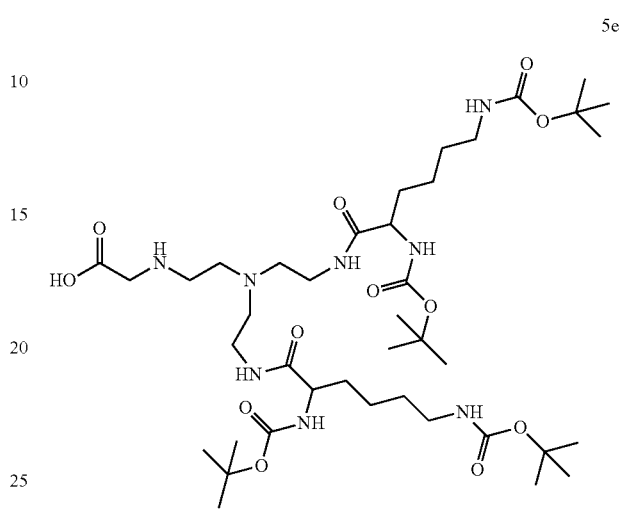

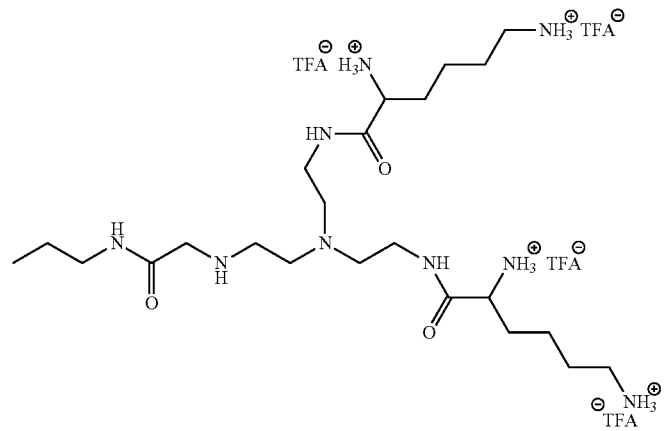

is obtained in four stages from the Chlorotrityl chloride resin 5a (FIG. 3)

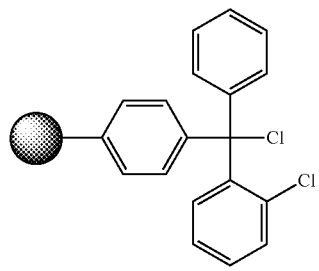

Stage 1: anchoring an acid function to a polymeric support 5a in order to obtain compound 5b

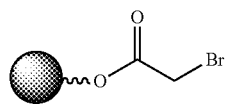

Chlorotrityl chloride resin 5a (1.4 mmol Cl/g resin; 5 g) is loaded into an SPPS reactor, 50 mL of $CH_2Cl_2$ are added and the mixture is stirred for 5 minutes. Bromoacetic acid (8.5 mmol; 1.2 g) is added, followed by DIPEA (9 mmol; 1.5 mL). The reactor is stirred at ambient temperature for 2 hours. The liquid is filtered and the resin is washed successively with $CH_2Cl_2$ and iPrOH (10×50 mL) then with MeOH (2×50 mL). Finally, the bromoacetyl-resin obtained (compound 5b, FIG. 3) is dried under a flow of nitrogen.

Stage 2: Coupling of tris-(2-aminoethyl)amine with bromoacetyl-resin 5b in order to obtain compound 5c Tris-(2-aminoethyl)amine (70 mmol; 10.2 g) is dissolved in 50 mL of $CH_2Cl_2$ and loaded into the reactor containing the bromoacetyl-resin 5b (stage 1). The reactor is stirred at ambient temperature for 2 hours. The solvent is filtered off and the resin washed successively with $CH_2Cl_2$ and iPrOH (10×50 mL). Finally, the bis-aminoethyl-resin obtained (compound 5c, FIG. 3) is dried under a flow of nitrogen. The Kaiser test is positive.

Stage 3: Coupling of $N_\alpha,N_\epsilon$-di-Boc-L-Lysine with bis-aminoethyl-resin 5c in order to obtain compound 5d

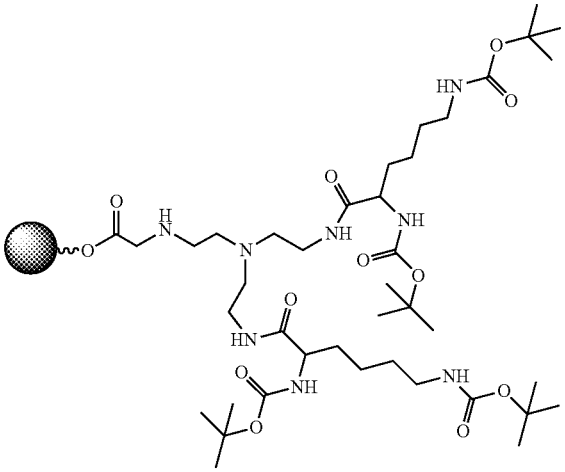

$N_\alpha,N_\epsilon$-di-BocL-Lysine (28 mmol; 9.70 g) and 1-Hydroxybenzotriazole (HOBt) (30 mmol; 4.05 g) are dissolved in 50 mL of $CH_2Cl_2$/DMF 4/1 (v/v). DIC (30 mmol; 5.1 mL) is added to the amino acid solution and the reaction medium is maintained under stirring and under an inert atmosphere for 30 min. The solution is then loaded into the reactor containing the bis-aminoethyl-resin 5c (stage 2). The reactor is stirred at ambient temperature for 18 hours. The solvent is filtered off and the resin washed successively with $CH_2Cl_2$ and iPrOH (10×50 mL) then with MeOH and ether (2×50 mL). Finally, the bis-(di-Boc-Lysine)-resin obtained (compound 5d, FIG. 3) is dried under a flow of nitrogen. The Kaiser test is negative.

Stage 4: Cleavage of bis-(di-Boc-Lysine)-resin 5d in order to obtain compound 5e

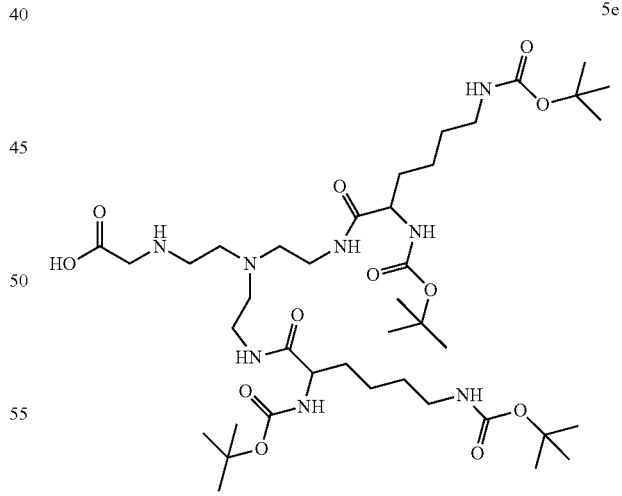

Bis-(di-Boc-Lysine)-resin 5d (stage 3) is loaded into a 250 mL flask equipped with a magnetic stirrer. A solution composed of 50 mL of $CH_2Cl_2$ and 25 mL of $CF_3CH_2OH$ is added and the mixture is stirred at ambient temperature for 2 hours. The solution is filtered, the resin is washed with $CH_2Cl_2$ (2×10 mL) and the organic phases thus obtained are combined and evaporated under a rough vacuum. The cleaved product is then purified by flash chromatography on silica gel with CH$_2$Cl$_2$/MeOH 9/1 (v/v) as eluent. In this way 1.98 g of compound 5e is isolated, i.e. a total yield of 34% from the Chlorotrityl chloride resin.

TLC: R$_f$ 5e=0.4 (CHCl$_3$/MeOH 9/1 (v/v))

ESI-MS+: m/z measured at 854.4 [M+Na]$^+$, calculated at 854.5 for C$_{38}$H$_{71}$N$_8$O$_{12}$Na.

5.2 Preparation of 181GSCL$_2$ (5f)

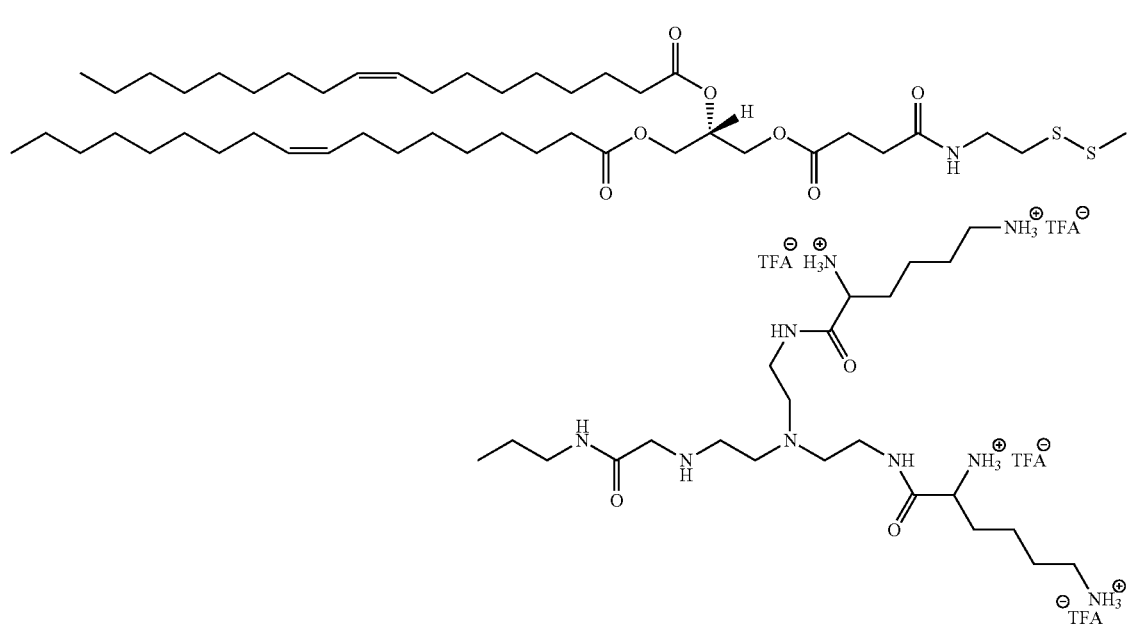

5f

The synthesis procedure is identical to the synthesis of 181GSCO (Example 1) but using compound 5e instead of N$_\alpha$,N$_\epsilon$-di-Boc-ornithine (1a). A total yield of 25% is obtained.

TLC: R$_f$ 5f=0 (CH$_2$Cl$_2$/MeOH 9/1 (v/v))

ESI-HRMS (high resolution with detection in positive mode): m/z measured at 1269.9072 [M+H]$^+$, calculated at 1269.9021 for C$_{65}$H$_{125}$N$_{10}$O$_{10}$S$_2$ (deviation: ppm

B. Preparation of Cytofectant Formulations from the Transfer Agents According to the Invention

Example 6

Formulation in the Form of Liposomes, Vesicles or Micelles in Water

One of the cationic lipids described in the previous examples is dissolved at a given concentration in chloroform. On the other hand, a co-lipid (dioleoylphosphatidylethanolamine, dioleoylphosphatidylcholine, cholesterol, cholesterolamine etc.) is also dissolved at a given concentration in chloroform. By combining different quantities of these two solutions in a pill box, different compositions of a mixture of cationic lipid and co-lipid are obtained. The chloroform is then evaporated off under a rough vacuum in order to obtain a lipid film along the walls of the pill box. This film is then rehydrated with a given quantity of sterile deionized water. After complete rehydration of the film, the dispersion is subjected to sonication in order to form small unilamellar liposomes.

For example, 600 μL (6 mg; 5 μmol) of a 10 mg·mL$^{-1}$ solution of 181GSCO (Example 1) in chloroform and 372 μL (3.72 mg; 5 μmol) of a 10 mg·mL$^{-1}$ solution of dioleoylphosphatidylethanolamine (DOPE) in chloroform are mixed in a pill box. The chloroform is evaporated to dryness under a rough vacuum and the lipid film obtained is resuspended in 5 mL of sterile deionized water. After rehydration overnight at 4° C., the dispersion is subjected to sonication for 15 minutes.

Example 7

Formulation in the Form of Liposomes, Vesicles or Micelles by Ethanolic Injection in Water One of the cationic lipids described in the previous examples is dissolved at a given concentration in chloroform. On the other hand, a co-lipid (dioleoylphosphatidylethanolamine, dioleoylphosphatidylcholine, cholesterol, cholesterolamine etc.) is also dissolved to a given concentration in chloroform. By combining different quantities of these two solutions in a pill box, different compositions of a mixture of cationic lipid and co-lipid are obtained. The chloroform is then evaporated off under a rough vacuum in order to obtain a lipid film along the walls of the pill box. This film is then re-dissolved in a small quantity of ethanol (between 3 and 5% of the final volume of the formulation). This ethanolic solution is then injected rapidly using a Hamilton syringe in a given volume of deionized water under stirring.

For example, 600 μL (6 mg; 5 μmol) of a 10 mg·mL$^{-1}$ solution of 181GSCO (Example 1) in chloroform and 372 μL (3.72 mg; 5 μmol) of a 10 mg·mL$^{-1}$ solution of dioleoylphosphatidylethanolamine (DOPE) in chloroform are mixed in a pill box. The chloroform is evaporated to dryness under a rough vacuum and the lipid film obtained is re-dissolved in 150 μL of ethanol. The ethanolic solution is then injected rapidly using a Hamilton syringe into a flask containing 5 mL of deionized water under vigorous stirring. The stirring is maintained for a few minutes.

Example 8

Formulation in an Ethanolic Solution

One of the cationic lipids described in the previous examples is dissolved at a given concentration in chloroform. On the other hand, a co-lipid (dioleoylphosphatidylethanolamine, dioleoylphosphatidylcholine, cholesterol, cholesterolamine etc.) is also dissolved at a given concentration in chloroform. By combining different quantities of these two solutions in a pill box, different compositions of a mixture of cationic lipid and co-lipid are obtained. The chloroform is then evaporated off under a rough vacuum in order to obtain a lipid film along the walls of the pill box. This film is then re-dissolved in an ethanol/deionized water solution 80/20 (v/v) under vigorous stirring.

For example, 600 μL (6 mg; 5 μmol) of a 10 mg·mL$^{-1}$ solution of 181GSCO (Example 1) in chloroform and 372 μL (3.72 mg; 5 μmol) of a 10 mg·mL$^{-1}$ solution of dioleoylphosphatidylethanolamine (DOPE) in chloroform are mixed in a pill box. The chloroform is evaporated to dryness under a rough vacuum and the lipid film obtained is re-dissolved in 5 mL of an ethanol/water solution 80/20 (v/v).

C. Applications

Transport of Active Molecules into Living Cells

Example 9

Use of the Transfer Agents According to the Invention for Transporting DNA into Living Cells

9.1 Material

The plasmid with which it is desired to transfect the cells, is either a pCMV-LacZ, or a pCMV-EGFP. pCMV-LacZ comprises the gene coding for an enzyme, β-galactosidase, under the CMV gene promoter. The activity of the β-galactosidase produced in the cells can be easily measured using colorimetric tests. The pCMV-EGFP comprises the gene coding for a fluorescent protein, GFP, under control of the CMV gene promoter. The GFP produced in the cells is observed with a fluorescence microscope and quantified by FACS. The plasmids are prepared from bacterial cultures (*E. Coli*) and purified on an affinity column. The solutions of nucleic acids obtained are diluted at 1 mg·mL$^{-1}$ in water and stored at −20° C.

9.2 Transfection Protocol

1. Preparation of Cells

Adherent immortalized cells (Vero, NIH-3T3, HeLa) are cultured in a 96-well culture plate (15,000 cells per well in 100 μL of DMEM) one day before the transfection test and are transfected while they are in the exponential growth phase and at 80% confluence.

The immortalized cells in suspension (Jurkat, K562) are prepared the day before the transfection at a density of 2 to 5×10$^6$ cells per mL. On the day of transfection 0.5 to 1×10$^5$ cells are cultured in a 96-well culture plate.

The solutions of DNA and the lipid formulations obtained according to Example 6 are taken to ambient temperature, and are carefully stirred by pipetting the solutions several times, by aspiration and dispensing, before being used for transfection. Then the DNA/lipid formulation complexes are prepared with different DNA contents and in lipid formulation as follows.

2. Dilution of the Lipid Formulation:

The lipid formulation is diluted with culture medium (DMEM) in 1.5 mL Eppendorf tubes. Three solutions diluted at different lipid formulation concentrations are prepared (Table 1).

TABLE 1

Diluted solutions of the lipid formulation

| | Volume of lipid formulation (μL) | Volume of DMEM (μL) | Volume of lipid formulation/well (μL) |
|---|---|---|---|
| Solution A | 2 | 198 | 0.5 |
| Solution B | 4 | 196 | 1 |
| Solution C | 8 | 192 | 2 |

3. The DNA stock solution (1 mg·mL$^{-1}$) is diluted in culture medium (DMEM) in 1.5 mL Eppendorf tubes. Three solutions diluted at different concentrations of DNA (Table 2) are prepared.

2-E: Diluted solutions of DNA

| | Volume of DNA stock solution (μL) | Volume of DMEM (μL) | Quantity of DNA/well (μg) |
|---|---|---|---|
| Solution D | 1 | 199 | 0.25 |
| Solution E | 2 | 198 | 0.5 |
| Solution F | 4 | 196 | 1 |

4. The DNA/lipid formulation complexes are prepared in 1.5 mL Eppendorf tubes, by mixing 50 μL of each diluted solution of lipid formulation with 50 μL of each diluted DNA solution. The mixtures are stirred carefully by pipetting the solutions several times, by aspiration and dispensing, then incubated for 20 minutes at ambient temperature.

5. The 100 μL of complexes are added to the cells in culture in complete medium (transfection in the presence of serum), and the mixture is homogenized by stirring the cell culture plate in order to allow a uniform distribution over the cells.

6. The cells are incubated at 37° C. in a humid atmosphere containing 5% CO$_2$ until measurement of the transgene expression. As a function of the activity of the promoter, the efficacy of the transfection can be evaluated from 24 to 72 hours post-transfection. A change of medium can be carried out 24 hours post-transfection (FIGS. 4 and 9).

Example 10

Use of the Products According to the Invention for Transporting siRNA into Living Cells

10.1 Material

The plasmid with which it is desired to transfect the cells is an anti-EGFP siRNA (Ambion, Tex., USA), the sequence of which is

```
5'-GCAAGCUGACCCUGAAGUUCUU
(sense)
and

5'-GAACUUCAGGGUCAGCUUGCUU
(antisense).
```

The efficacy of the sequence in inhibiting the GFP produced in the cells is observed with a fluorescence microscope and measured by FACS. A control siRNA was used to measure non-specific inhibition. The RNA solutions are at 1 $\mu mol.L^{-1}$ in water and are stored at −20° C.

10.2 Transfection Protocol

1. Preparation of Cells

Hela-GFP cells are cultured in a 24-well cell culture plate (60,000 cells per well in 400 μL of DMEM) one day before the transfection test and transfected while they are in the exponential growth phase and at 80% confluence.

2. The siRNA solution and the lipid formulation obtained according to Example 6 are taken to ambient temperature, and carefully stirred by pipetting the solutions several times, by aspiration and dispensing, before being used for the transfection.

3. The siRNA stock solution (1 $\mu mol.L^{-1}$) is diluted in a total volume of 50 μL with culture medium (DMEM) in a 1.5 mL Eppendorf tube. A series of several diluted solutions are prepared (Table 3) in order to test the efficacy of inhibition of the plasmid at several final concentrations (1 nM, 10 nM and 20 nM).

TABLE 3

Diluted siRNA solutions

| Final siRNA solution (nmol·$L^{-1}$) | Quantity of siRNA (ng) | Volume of siRNA at 1 μmol·$L^{-1}$ (μL) | Volume of DMEM (μL) |
|---|---|---|---|
| 1 | 6.75 | 0.5 | 49.5 |
| 10 | 67.5 | 5 | 45 |
| 20 | 135 | 10 | 40 |

4. The lipid formulation is diluted in a total volume of 50 μL with culture medium (DMEM) in a 1.5 mL Eppendorf tube. A series of several diluted solutions are prepared for each final concentration of siRNA (Table 4).

TABLE 4

Diluted solutions of the lipid formulation

| Final concentration of siRNA (nmol·$L^{-1}$) | Volume of lipid formulation (μL) | Volume of DMEM (μL) |
|---|---|---|
| 1 | 1 | 49 |
| 10 | 2 | 48 |
| 20 | 3 | 47 |

5. The siRNA/lipid formulation complexes are prepared by adding 50 μL of the diluted plasmid solution to 50 μL of the diluted lipid formulation solution. The mixture is stirred carefully by pipetting the solution several times, by aspiration and dispensing, then incubated for 20 minutes at ambient temperature.

6. 100 μL of complexes are added to the cells in culture in complete medium (transfection in the presence of serum), and the mixture is homogenized by stirring the cell culture plate in order to allow a uniform distribution over the cells.

7. The cells are incubated at 37° C. in a humid atmosphere containing 5% $CO_2$ for 72 hours. The cells are then trypsinized and the inhibition efficacy is observed by electron microscopy and/or analyzed quantitatively by FACS (FIGS. 5 and 6).

Example 11

Use of the Products According to the Invention for Transporting Proteins into Living Cells

11.1 Material

The polypeptides that it is desired to deliver into the cells are a purified goat IgG (Sigma-Aldrich SARL, Saint Quentin Fallavier, France), previously labelled with fluorescein, an R-Phycoerythrin (Invitrogen, San Diego, Calif., USA) and a β-galactosidase (Merck KGaA, Darmstadt, Germany). The polypeptides are used in solution at 100 $\mu g.mL^{-1}$ in PBS. The efficacy of transport of the labelled polypeptides into the cells is observed with a fluorescence microscope and is quantified by FACS. The activity of the β-galactosidase produced in the cells is easily measured using colorimetric tests.

11.2 Procedure

1. Preparation of Cells

Adherent immortalized cells (Vero, NIH-3T3, HeLa) are cultured in a 24-well cell culture plate (75,000 cells per well in 400 μL of DMEM) one day before the polypeptides, proteins or antibodies delivery test so that they are in the exponential growth phase and at 80% confluence during the experiment.

The immortalized cells in suspension (Jurkat, K562) are prepared the day before the transfection at a density of 2 to $5\times10^6$ cells per mL. On the day of the transfection 1.5 to $5\times10^5$ cells are cultured in a 96-well culture plate.

2. The polypeptide solution and the lipid formulation obtained according to Example 8 are taken to ambient temperature, and are carefully stirred by pipetting the solutions several times, by aspiration and dispensing, before being used for the delivery test.

3. 2 μL of the lipid formulation is added to the bottom of a 1.5 mL Eppendorf tube.

4. 1 μg of polypeptide is then added to the tube containing the lipid formulation. The mixture is stirred carefully by pipetting the solution several times, by aspiration and dispensing, then incubated for 10 minutes at ambient temperature.

5. Then 100 μL of culture medium (DMEM) are added to the polypeptide/lipid formulation mixture and the solution is stirred carefully by pipetting several times, by aspiration and dispensing.

6. The complexes are then immediately added to the cells in culture in complete medium (transfection in the presence of serum), and the mixture is homogenized by stirring of the cell culture plate in order to allow a uniform distribution over the cells.

7. The cells are incubated at 37° C. in a humid atmosphere containing 5% $CO_2$ under standard conditions. The efficacy of intracellular delivery of the polypeptides or proteins or antibodies is analyzed after incubation for 3 to 48 hours (FIGS. 7, 8 and 10).

The invention claimed is:

1. A cationic amphipathic compound of formula (I):

(I)

in which:
R corresponds to formula (II):

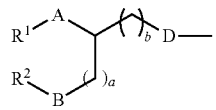
(II)

in which:
R¹ and R², identical or different, represent a linear, branched and/or cyclic, saturated or unsaturated hydrocarbon group comprising from 6 to 24 carbon atoms;
A and B, identical, represent -O—C(O)—; —CO—NH—; —NH—CO—; —NH— or —O— group; or
A and B, different, represent a —C(O)—O—; —O—C(O)—; —CO—NH—; —NH—CO—; —NH— or —O— group;
a is an integer comprised between 1 and 6;
b is an integer comprised between 0 and 6; and
D represents an —NH—, —CO—, —O— or —S— group;
E represents a linear or branched hydrocarbon group which can comprise from 1 to 15 carbon atoms, and which can optionally comprise one or more heteroatoms;
m is 1;
AA represents an amino acid radical;
n is an integer equal to 0 or 1;
$W_1$ and $W_2$, identical or different, represent a linear or branched hydrocarbon group which can comprise from 1 to 15 carbon atoms, which can optionally comprise one or more heteroatoms;
L represents an ester (CO—O—), disulfide (—S—S—), vinyl ether (—O—C=C—), acylhydrazone (CO—NR—N=CR'R") group;
p is an integer equal to 0 or 1;
Y is a branched hydrocarbon group which can comprise from 1 to 20 carbon atoms, and/or one or more heteroatoms, and which can optionally be covalently coupled with the $W_2$ or AA or E or R group on the one hand, and to at least two Y and/or Z groups on the other hand;
q is an integer comprised between 0 and 8;
Z represents a basic amino acid;
r is an integer comprised between 1 and 16, it being understood that if q is equal to 1 then r is at least equal to 2 and that if r is greater than 1, then the Z groups can be identical or different; and
s is an integer equal to 1 or 2;
and physiologically acceptable addition salts thereof.

2. Compound according to claim 1, wherein R corresponds to formula (IV):

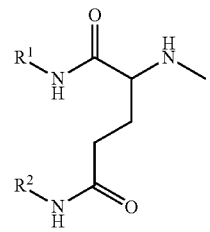
(IV)

in which $R^2$ and $R^2$ have the same meaning as previously.

3. The compound according to claim 1, wherein E then corresponds to formula (V): $-G_1-X1-x-G1$ in which
$X_1$ represents a bridging alkylene group comprising from 1 to 8 carbon atoms, and
$G_1$ represents a —CO— or —NH— group.

4. The compound according to claim 3, wherein E corresponds to the formula CO—$X_1$—CO in which $X_1$ has the same meaning as described in claim 3.

5. The compound according to claim 1, wherein $W_1$ corresponds to the formula: $-G_2-X_2-$ and $W_2$ corresponds to formula (VII): —$X_3$-$G_3$- in which $X_2$ and $X_3$, identical or different, represents a bridging alkylene group comprising from 1 to 8 carbon atoms, whilst $G_2$ and $G_3$, identical or different, represent a —CO—, —NH— or —O— group.

6. The compound according to claim 1, wherein Y corresponds to formula (VIII): —CO—$X_4$—NH—$X_5$—N—[$X_6$—NH]$_2$- or (IX): —NH—$X_5$—N—[$X_6$—NH]$_2$—, in which $X_4$, $X_5$ and $X_6$, identical or different, represent a bridging alkylene group comprising from 1 to 8 carbon atoms.

7. The compound according to claim 6, wherein $X_4$ represents a methylene.

8. The compound according to claim 6, wherein $X_5$ and $X_6$ represent a bridging alkylene group comprising from 1 to 4 carbon atoms.

9. The compound according to claim 1, wherein the counter-ion of the physiologically acceptable addition salts is chosen from organic anions or inorganic anions.

10. A compound chosen from the compounds of formula:

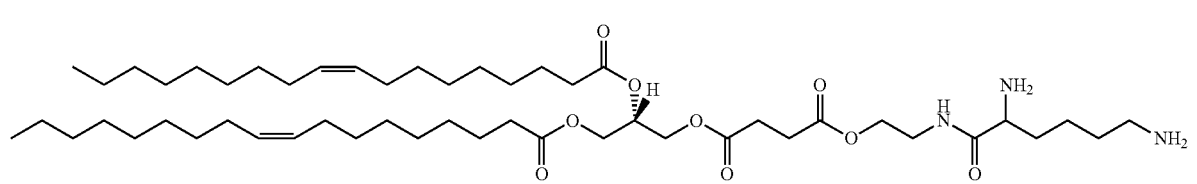
I.1

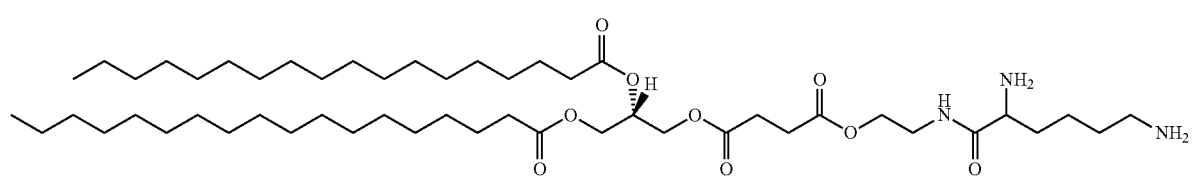
I.2

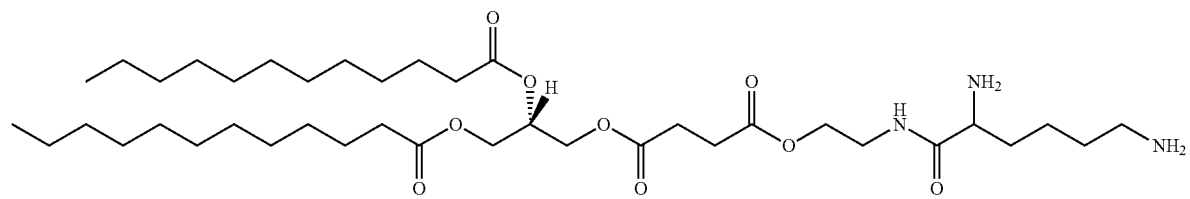
I.3
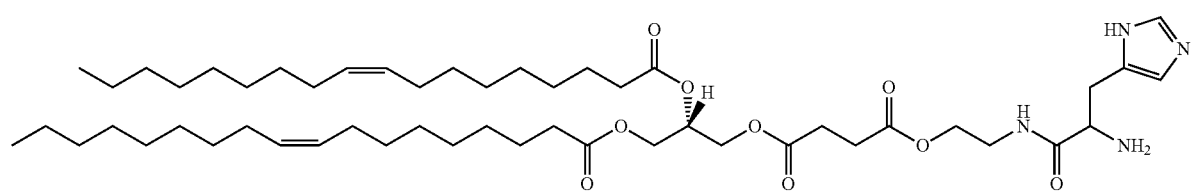
I.4
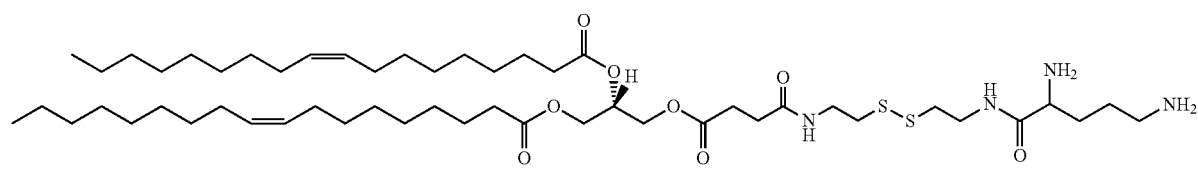
I.6
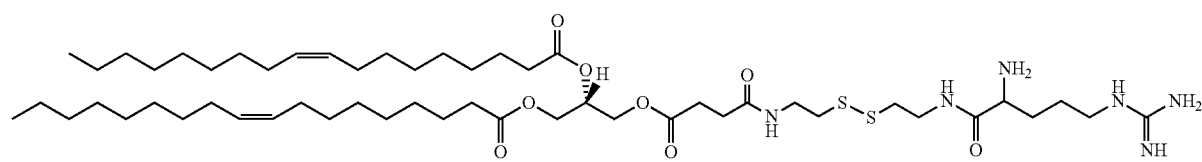
I.7
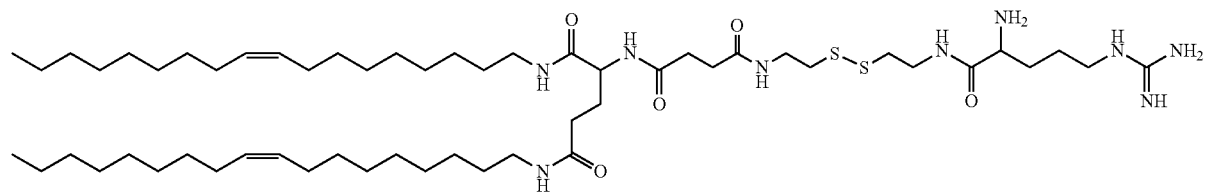
I.8
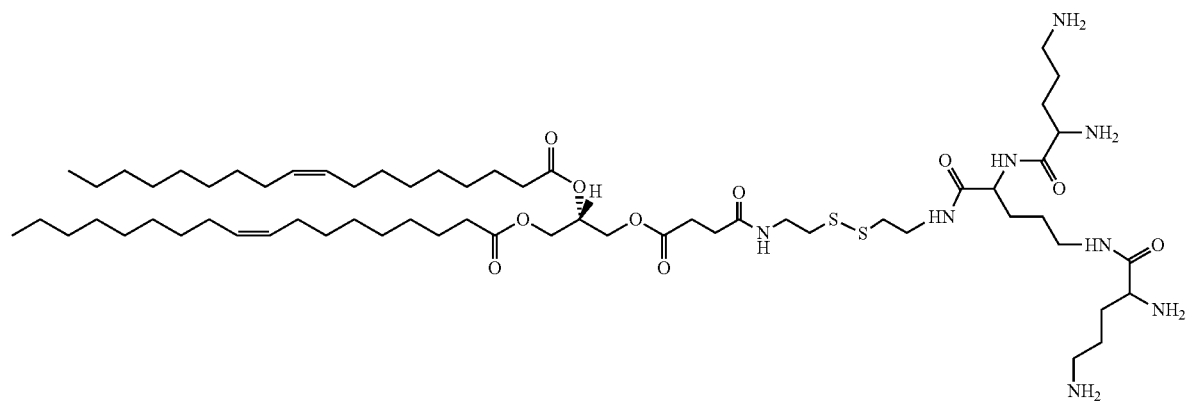
I.9

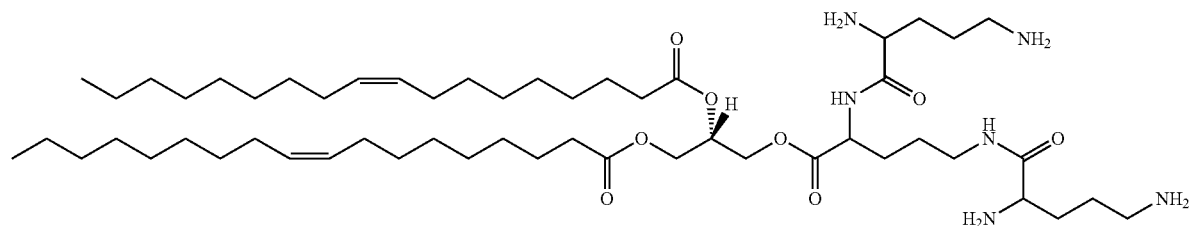
I.10
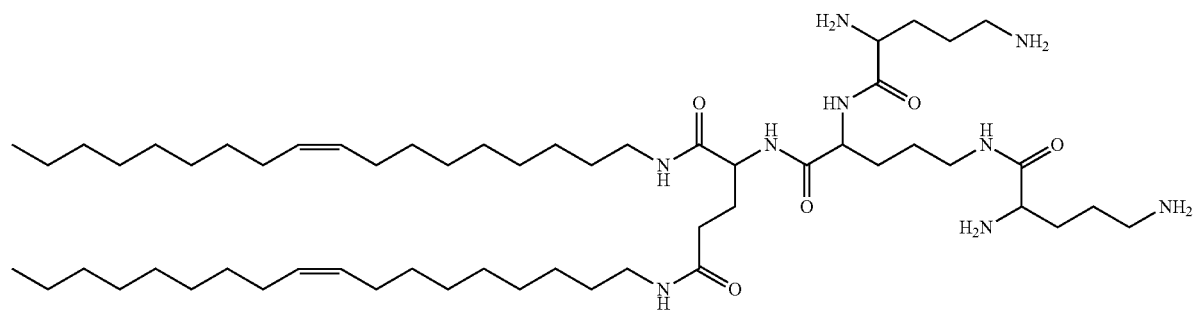
I.11
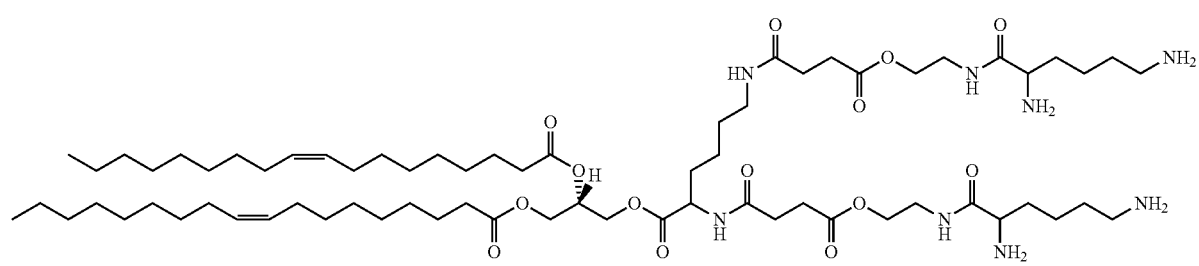
I.12
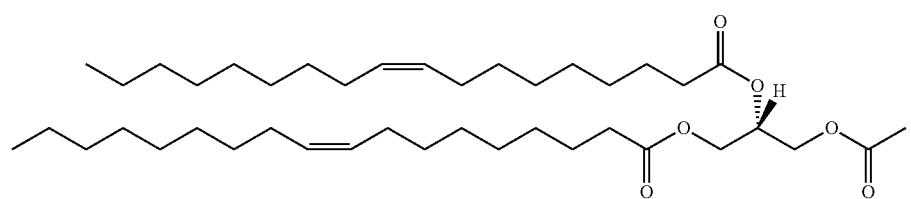
I.13

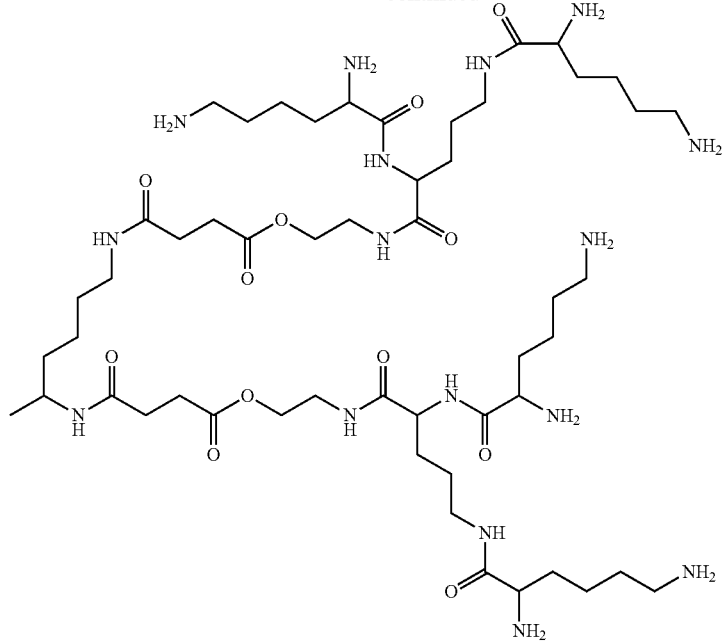
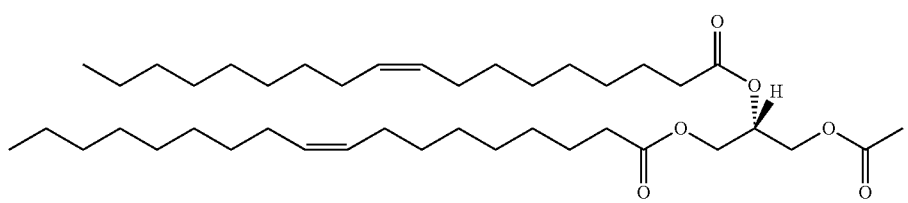
I.14
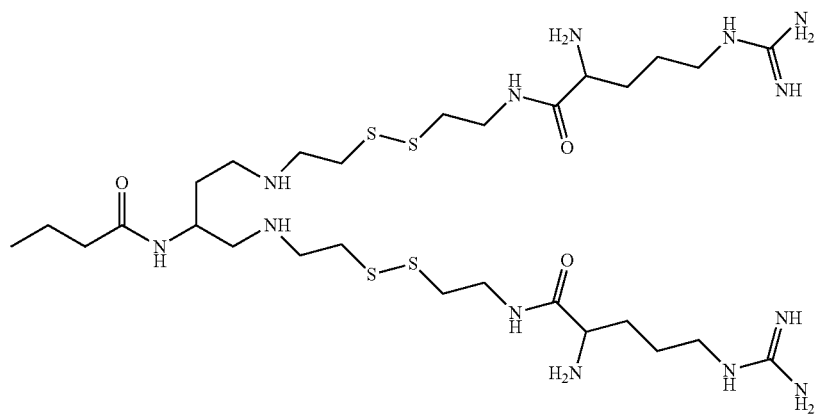
I.15
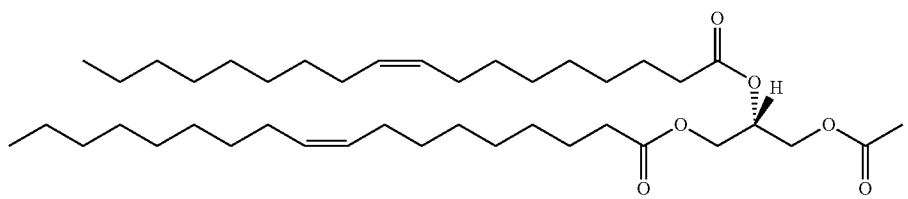

-continued
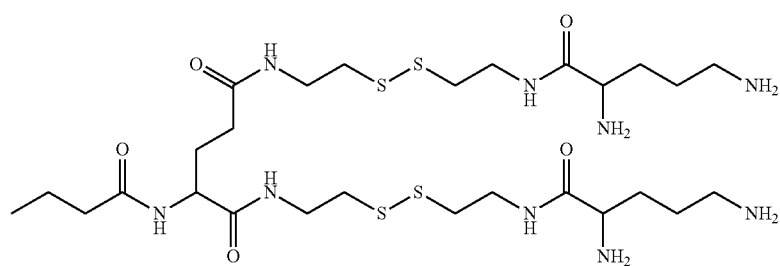
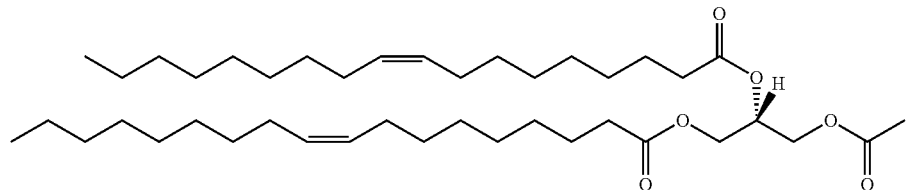
I.16
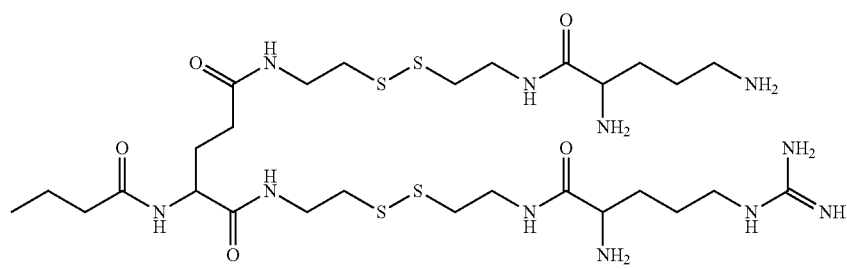
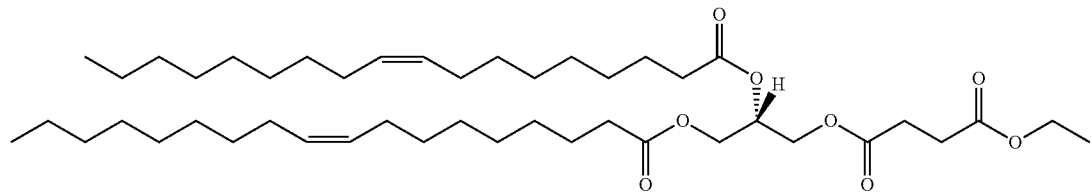
I.17
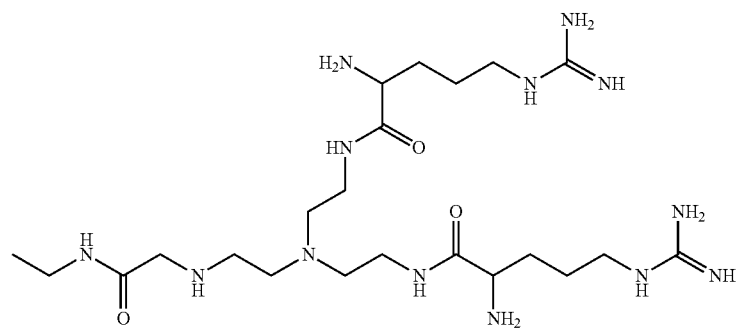
I.18
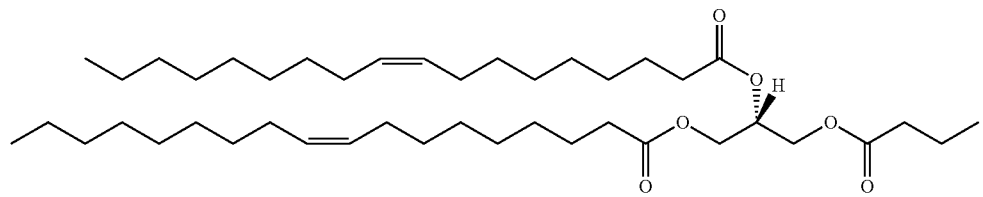

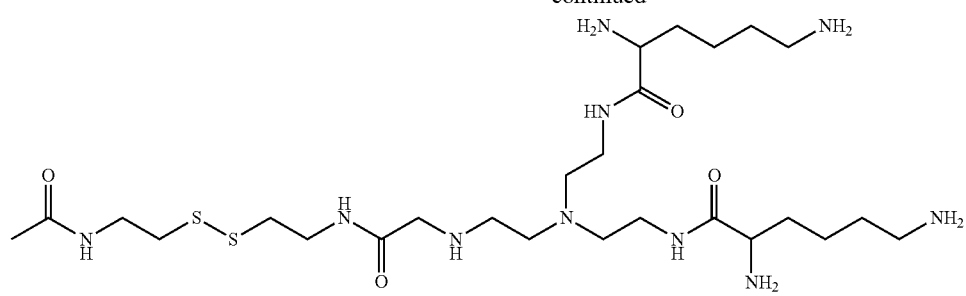
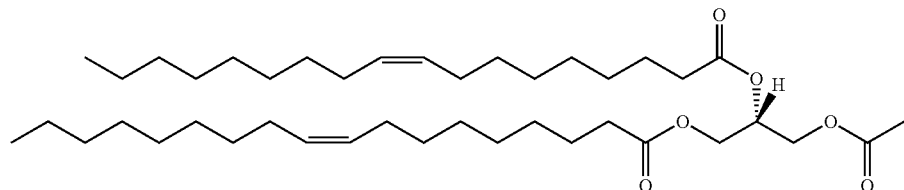
I.19
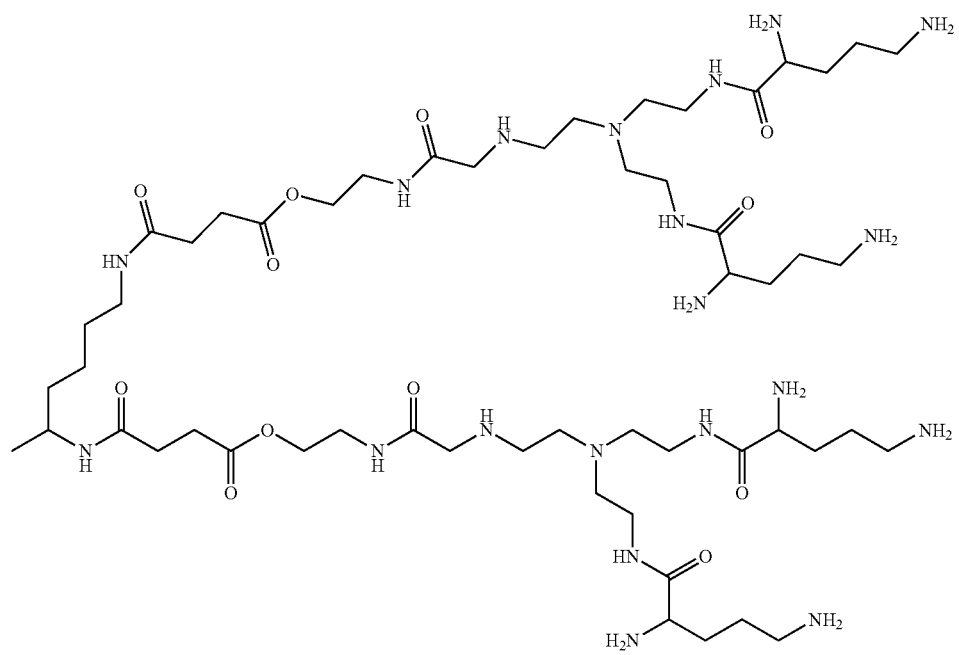
I.20
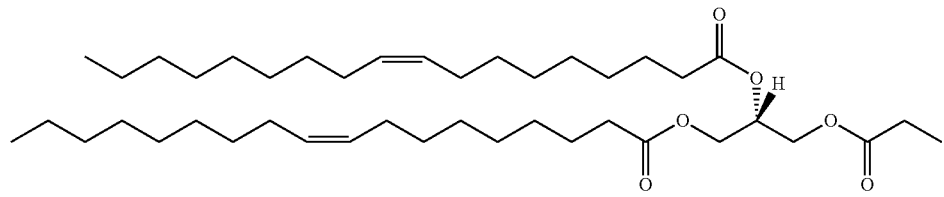

-continued

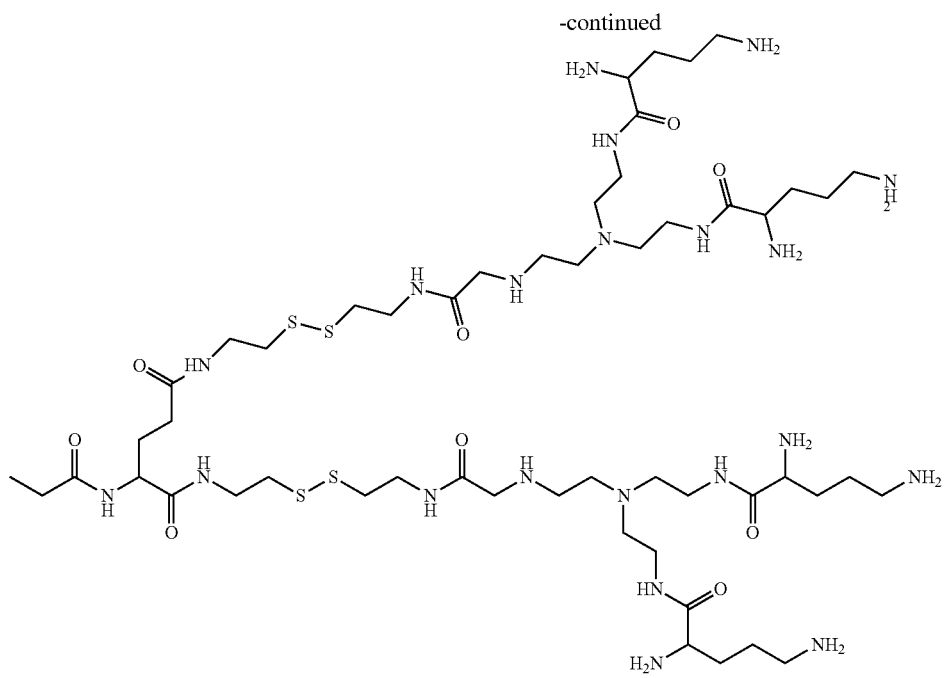

11. A composition, comprising a compound of claim 1.

12. Composition according to claim 11, characterized in that it also comprises at least one nucleic acid or a polynucleotide.

13. Composition according to claim 12, characterized in that the compound of formula (I) and the nucleic acid are present in quantities such that the ratio of positive charges of the compound of formula (I) to the negative charges of the nucleic acid is comprised between 0.1 and 50, preferentially between 0.5 and 20.

14. Composition according to claim 12, characterized in that the quantity of compound of formula (I) is comprised between 1 and 12 nanomoles per μg of nucleic acid, and preferably between 1 and 9 nanomoles per μg of nucleic acid.

15. Composition according to claim 3, characterized in that it also comprises at least one polypeptide or a protein.

16. Composition according to claim 15, characterized in that the compound of formula (I) and the polypeptide or the protein are present in quantities such that the quantity of compound of formula (I) is comprised between 1 and 10 nanomoles of compound per μg of polypeptide, and preferably between 1 and 3 nanomoles per μg of polypeptide.

17. Composition according to claim 11, characterized in that it also comprises at least one biologically active molecule other than a nucleic acid or a polypeptide such as for example an active ingredient, a polysaccharide, a lipid, a peptoid.

18. Composition according to claim 11, characterized in that it also comprises at least one adjuvant such as:
one or more neutral (zwitterionic or free of ionic charges), anionic or cationic lipids, such as for example neutral lipids with two fatty chains, cholesterol or cholesterol derivatives, more particularly chosen from dioleoylphosphatidylethanolamine (DOPE), oleoylpalmitoylphosphatidylethanolamine (POPE), distearoyl-, dipalmitoyl-, dimyristoyl-, dilauroylphosphatidylethanolamines (DSPE, DPPE, DMPE, DLPE), as well as their once to three times N-methylated derivatives (DOPC, DPPC, DMPC), the phosphatidylglycerols, the glycosyldiacylglycerols, the cerebrosides (such as in particular the galactocerebrosides), the sphingolipids (such as in particular the sphingomyelines), the asialogangliosides (such as in particular asialoGM1 and GM2), or also such as lipid ethers, or also lipids comprising a single fatty chain, including the lysophosphatides, lysophosphatidylcholines, lysophosphatidylethanolamines, lysophosphatidylglycerols, lysophosphatidylserines or also such as the lysophosphatidic acids, whether natural or synthetic or also such as one or more polymers, natural or synthetic, co-polymers and/or dendrimers, cationic such as the polyamines, including polyethylenimine, polylysine, polyornithine, or also polybrene and chitosan, or anionic such as polyglutamic acid, polypropylacrylic acid, hyaluronic acid and polylactic-co-glycolic acid (PGLA), or neutral such as polyethylene glycol (PEG) or also certain polysaccharides such as the galactomannans, or also such as nanoparticles, in particular magnetic particles, particles based on organic or inorganic compounds or also such as polypeptides, proteins, monosaccharides, glycerol, cyclodextrins, histones, deoxycholic acid and any other "activator" ("enhancer") which improves the efficacy of delivery and the pharmacology or also such as adjuvants capable of specifically targeting a determinant at the surface and/or inside the cells, optionally covalently or non-covalently attached to the compound corresponding to formula (I) or to any other molecules contained in the composition comprising the compound of formula (I), for example ligands of receptors expressed at the surface of the target cells, for example a sugar, a folate, transferrin, insulin, a hormone, a peptide, an antibody, a metabolite, vitamins or any other molecule which can recognize an extracellular receptor, or an element of intracellular vectorization for targeting specific compartments such as the mitochondria, nucleus or cytoplasm, such as for example a nuclear or mitochondrial localization signal such as for example a sugar, a peptide, a protein, an antibody, an antibody fragment, a ligand or a ligand fragment or also a fluorophore such as rhodamine, fluorescein or biotin or also viruses, for example lentiviruses, retroviruses, adenoviruses, the herpes virus, baculoviruses, and/or unicellular organisms, for example bacteria, yeasts, fungi or parasites.

19. Kit for the transfer of biological material, comprising at least one compound of claim 1.

20. Kit for the transfer of biological material, comprising the composition of claim 11.

21. The compound according to claim 1, wherein R is one or more alkyl chains comprising between 10 and 18 carbon atoms.

22. The compound according to claim 1, wherein r is an integer comprised between 1 and 8.

23. The compound according to claim 1, wherein R1 and R2, identical or different, represent a linear, branched and/or cyclic, saturated or unsaturated hydrocarbon group comprising from 10 to 18 carbon atoms.

24. The compound according to claim 1, wherein Z is selected from the group consisting of lysine, ornithine, arginine, and histidine.

25. A method for transferring a molecule of biological interest into cells, comprising:
bringing the molecule of biological interest into contact with a compound of claim 1 to form an active molecule/transfer agent complex; and
bringing the cells into contact with the formed complex.

26. The method of claim 25, wherein the molecule of biological interest is a nucleic acid, a polypeptide or a biologically active molecule.

27. The method of claim 25, wherein the molecule of biological interest is comprised in a composition.

28. The method of claim 25, wherein the cells are previously isolated cells.

29. The method of claim 25, which is carried out in cells in vitro or in vivo or ex vivo.

30. The method of claim 25, further comprising one or more stages of bringing the compound into contact with one or more other transfection agent(s) and/or one or more adjuvants.

31. The method of claim 25, wherein the step of bringing the molecule of biological interest into contact with the compound is preceded by first bringing the compound into contact with one or more other transfection agents and/or first bringing the compound into contact with the adjuvant or adjuvants.

32. Transfer kit for the implementation of the method as described in claim 25, characterized in that it comprises at least one compound corresponding to formula (I):

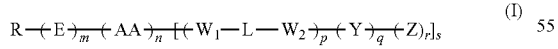

in which:
R represents a lipophilic region which can comprise one or more groups chosen from
one or more alkyl chains, comprising 6 to 24 carbon atoms, preferentially between 10 and 18 carbon atoms, branched or linear, unsaturated or saturated, optionally fluorinated; or
one or more cyclic or polycyclic groups known to be lipophilic such as a steroid group (for example a cholesterol derivative), a polyaromatic group (for example a naphthalene, dansyl, or anthracene derivative), or an alkaloid derivative group; or a natural or synthetic lipid;

E represents a linear or branched hydrocarbon group which can comprise from 1 to 15 carbon atoms, preferentially from 1 to 8, and which can optionally comprise one or more heteroatoms;

m is an integer equal to 0 or 1;

AA represents an amino acid radical;

n is an integer equal to 0 or 1;

$W_1$ and $W_2$, identical or different, represent a linear or branched hydrocarbon group which can comprise from 1 to 15 carbon atoms, preferentially from 1 to 6, which can optionally comprise one or more heteroatoms;

L represents a functional group which can incorporate at least one bond which is sensitive to its environment, which is stable in extracellular medium and rapidly cleaved in the intracellular medium as it is sensitive
to stimuli such as pH reduction (for example vinyl ether or acylhydrazone groups sensitive to acid medium) or a change in the oxidation-reduction potential (for example a disulphide bond, cleaved in reducing medium),
to enzymes (for example an ester bond, cleaved by endogenous esterases); or also
to light radiation (bearing photosensitive groups for example);

p is an integer equal to 0 or 1;

Y is a branched hydrocarbon group which can comprise from 1 to 20 carbon atoms, preferentially from 1 to 12, and/or one or more heteroatoms, and which can optionally be covalently coupled with the $W_2$ or AA or E or R group on the one hand, and to at least two Y and/or Z groups on the other hand;

q is an integer comprised between 0 and 8, preferably between 0 and 3;

Z represents a basic amino acid or serine;

r is an integer comprised between 1 and 16, preferably between 1 and 8, it being understood that if q is equal to 1 then r is at least equal to 2 and that if r is greater than 1, then the Z groups can be identical or different;

s is an integer equal to 1 or 2;

and its physiologically acceptable addition salts.

33. Transfer kit for the implementation of the method as described in claim 25, characterized in that it comprises a composition, preferentially cosmetic or pharmaceutical or laboratory reagent, comprising a compound of formula (I):

in which:
R represents a lipophilic region which can comprise one or more groups chosen from
one or more alkyl chains, comprising 6 to 24 carbon atoms, preferentially between 10 and 18 carbon atoms, branched or linear, unsaturated or saturated, optionally fluorinated; or
one or more cyclic or polycyclic groups known to be lipophilic such as a steroid group (for example a cholesterol derivative), a polyaromatic group (for example a naphthalene, dansyl, or anthracene derivative), or an alkaloid derivative group; or a natural or synthetic lipid;

E represents a linear or branched hydrocarbon group which can comprise from 1 to 15 carbon atoms, preferentially from 1 to 8, and which can optionally comprise one or more heteroatoms;

m is an integer equal to 0 or 1;

AA represents an amino acid radical;

n is an integer equal to 0 or 1;

$W_1$ and $W_2$, identical or different, represent a linear or branched hydrocarbon group which can comprise from 1 to 15 carbon atoms, preferentially from 1 to 6, which can optionally comprise one or more heteroatoms;

L represents a functional group which can incorporate at least one bond which is sensitive to its environment, which is stable in extracellular medium and rapidly cleaved in the intracellular medium as it is sensitive to stimuli such as pH reduction (for example vinyl ether or acylhydrazone groups sensitive to acid medium) or a change in the oxidation-reduction potential (for example a disulphide bond, cleaved in reducing medium), to enzymes (for example an ester bond, cleaved by endogenous esterases); or also to light radiation (bearing photosensitive groups for example);

p is an integer equal to 0 or 1;

Y is a branched hydrocarbon group which can comprise from 1 to 20 carbon atoms, preferentially from 1 to 12, and/or one or more heteroatoms, and which can optionally be covalently coupled with the $W_2$ or AA or E or R group on the one hand, and to at least two Y and/or Z groups on the other hand;

q is an integer comprised between 0 and 8, preferably between 0 and 3;

Z represents a basic amino acid or serine;

r is an integer comprised between 1 and 16, preferably between 1 and 8, it being understood that if q is equal to 1 then r is at least equal to 2 and that if r is greater than 1, then the Z groups can be identical or different;

s is an integer equal to 1 or 2;

and its physiologically acceptable addition salts.

* * * * *